United States Patent
Jackson et al.

(10) Patent No.: US 9,619,624 B2
(45) Date of Patent: *Apr. 11, 2017

(54) SYSTEMS AND METHODS FOR IDENTIFYING UNKNOWN DRUG TARGETS VIA ADVERSE EVENT DATA

(71) Applicant: MOLECULAR HEALTH GMBH, Heidelberg (DE)

(72) Inventors: David B. Jackson, Heidelberg (DE); Theodoros Soldatos, Heidelberg (DE); Guillaume Taglang, Heidelberg (DE); Alexander Zien, Heidelberg (DE); Stephan Brock, Weinheim (DE)

(73) Assignee: MOLECULAR HEALTH GMBH, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/849,211

(22) Filed: Sep. 9, 2015

(65) Prior Publication Data
US 2015/0379219 A1    Dec. 31, 2015

Related U.S. Application Data

(63) Continuation of application No. 13/446,871, filed on Apr. 13, 2012, now Pat. No. 9,218,457.
(Continued)

(51) Int. Cl.
*G06F 19/00* (2011.01)
*G06F 19/18* (2011.01)

(52) U.S. Cl.
CPC ............ *G06F 19/345* (2013.01); *G06F 19/18* (2013.01); *G06F 19/326* (2013.01); *G06F 19/3437* (2013.01)

(58) Field of Classification Search
None
See application file for complete search history.

(56) References Cited

U.S. PATENT DOCUMENTS 5,845,255 A    12/1998    Mayaud
2001/0020240 A1    9/2001    Classen
(Continued)

OTHER PUBLICATIONS

Monica Campillos, Michael Kuhn, Anne-Claude Gavin, Lars Juhl Jensen, Peer Bork. Drug Target Identification Using Side-Effect Similarity. Science Jul. 11, 2008 : 263-266.*
Keiser, Michael J., et al. "Predicting new molecular targets for known drugs." Nature 462.7270 (2009): 175-181.*
US Notice of Allowance in U.S. Appl. No. 13/446,871 DTD Oct. 23, 2015.
(Continued)

*Primary Examiner* — Stanley K Hill
*Assistant Examiner* — David H Kim
(74) *Attorney, Agent, or Firm* — Foley & Lardner LLP; Daniel E. Rose; Christopher J. McKenna

(57) ABSTRACT

The present disclosure is directed to systems and methods for identifying unknown drug targets via adverse event data. An analyzer receives an identification of a first drug having one or more unknown target proteins and identifies a second drug related to the first drug. The analyzer retrieves, from an adverse event database, a first side effect profile associated with the first drug, and a second side effect profile associated with the second drug. The analyzer generates a third side effect profile comprising a subset of the first side effect profile not shared by the second side effect profile, and identifies a third drug having a fourth side effect profile comprising the third side effect profile. The analyzer retrieves a list of one or more target proteins of the third drug not targeted by the second drug, and presents the retrieved list as potential target proteins of the first drug.

18 Claims, 56 Drawing Sheets

Related U.S. Application Data

(60) Provisional application No. 61/584,164, filed on Jan. 6, 2012, provisional application No. 61/605,625, filed on Mar. 1, 2012.

(56) References Cited

U.S. PATENT DOCUMENTS

| | | | |
|---|---|---|---|
| 2002/0002473 A1 | 1/2002 | Schrier et al. | |
| 2002/0165845 A1 | 11/2002 | Gogolak | |
| 2002/0173993 A1 | 11/2002 | Skulason et al. | |
| 2002/0187514 A1 | 12/2002 | Chen et al. | |
| 2003/0046110 A1 | 3/2003 | Gogolak | |
| 2003/0186244 A1 | 10/2003 | Margus et al. | |
| 2003/0204319 A1 | 10/2003 | Arouh et al. | |
| 2004/0172285 A1 | 9/2004 | Gibson | |
| 2006/0047538 A1 | 3/2006 | Condurso et al. | |
| 2007/0003931 A1 | 1/2007 | Mrazek et al. | |
| 2007/0212719 A1 | 9/2007 | Hlavacek et al. | |
| 2007/0219825 A1 | 9/2007 | Maetzold et al. | |
| 2007/0275060 A1 | 11/2007 | Befumo | |
| 2009/0094059 A1 | 4/2009 | Coleman et al. | |
| 2010/0145722 A1 | 6/2010 | Zalta | |
| 2011/0016427 A1 | 1/2011 | Douen | |
| 2011/0082867 A1 | 4/2011 | Bruns et al. | |
| 2012/0101847 A1 | 4/2012 | Johnson et al. | |
| 2013/0144584 A1* | 6/2013 | Chen | G06F 19/3456 703/11 |
| 2013/0282404 A1 | 10/2013 | Janevski et al. | |

OTHER PUBLICATIONS

US Notice of Allowance on U.S. Appl. No. 13/446,912 Dated Nov. 24, 2015.
Blinov, et at., "Graph Theory for Rule-Based Modeling of Biochemical Networks", Transactions on Computational Systems Biology VII: Lecture Notes in Computer Science (2006); vol. 4230; pp. 89-106.
Drugs.com, Prescription Drug Information, Interactions & Side Effects, Jan. 2011.
FDA, Adverse Event Reporting System (AERS) Jan. 2011.
US Notice of Allowance on U.S. Appl. No. 13/446,871 DTD Jun. 5, 2015.
US Office Action for U.S. Appl. No. 13/446,917 dated Sep. 9, 2014.
US Office Action for U.S. Appl. No. 13/446,871 dated Oct. 29, 2014.
US Office Action for U.S. Appl. No. 13/446,912 dated Oct. 31, 2014.
US Office Action for U.S. Appl. No. 13/446,912 dated Feb. 11, 2014.
US Office Action for U.S. Appl. No. 13/446,917 dated Jan. 30, 2014.
US Office Action on U.S. Appl. No. 13/446,917 DTD Aug. 7, 2013.
US Office Action on U.S. Appl. No. 13/446,820 DTD Mar. 5, 2013.
US Office Action on U.S. Appl. No. 13/446,820 DTD Aug. 21, 2013.
US Office Action on U.S. Appl. No. 13/446,912 DTD Jun. 18, 2015.
US Office Action on U.S. Appl. No. 13/446,917 dated May 14, 2015.
US Office Action on U.S. Appl. No. 13/446,820 dated Oct. 6, 2014.

\* cited by examiner

| | |
|---|---|
| Cytochrome c | 175 ATC Classes - Level 3 |
| STATISTICS | Page 1 of 9 |
| Cytochrome c | Name / AEs |
| Drugs (831) | Stomatological preparations / 2213 |
| ATC classes | Tetracyclines / 2213 |
| Level 1 | Anti-acne preparations for topical use / 472 |
| Level 2 | Drugs for peptic ulcer and gastro-oesophageal reflux disease (gord) / 468 |
| Level 3 | |
| Level 4 | Corticosteroids for systemic use, plain / 401 |
| Indications (762) | Corticosteroids, plain / 382 |
| Reactions (2759) | Other antineoplastic agents / 379 |
| Molecular targets (1474) | Decongestants and other nasal preparations for topical use / 363 |
| Molecular mechanisms (78 | |
| ADVERSE EVENTS | Intestinal antiinflammatory agents / 343 |
| Cytochrome c | Antidepressants / 338 |
| Drugs | Antiinfectives / 316 |
| ATC classes | Other analgesics and antipyretics / 309 |
| Level 1 | Antiinflammatory agents / 306 |
| Level 2 | Antithrombotic agents / 284 |
| Level 3 | Corticosteroids, other combinations / 277 |
| Level 4 | Agents for treatment of hemorrhoids and anal fissures for topical use / 267 |
| Indications | |
| Reactions | |
| Molecular targets | |
| Molecular mechanisms | |
| LITERATURE | Page 1 of 9    Displaying 1 - 20 of 175 |
| Cytochrome c | |
| Drugs | |
| Indications | |
| Reactions | |

SYSTEMS AND METHODS FOR IDENTIFYING UNKNOWN DRUG TARGETS VIA ADVERSE EVENT DATA

RELATED APPLICATIONS

The present application claims the benefit of and priority as a continuation to U.S. application Ser. No. 13/446,871, entitled "Systems and Methods for Identifying Unknown Drug Targets via Adverse Event Data," filed Apr. 13, 2012; which claims priority to and the benefit of U.S. Provisional Patent Application No. 61/584,164, entitled "Translating Clinico-Molecular Data Into Safer, More Effective Drug Choices," filed Jan. 6, 2012, and U.S. Provisional Patent Application No. 61/605,625, entitled "Systems and Methods for Analysis of Adverse Event Data," filed Mar. 1, 2012; each of which are hereby incorporated by reference in their entirety.

FIELD OF THE INVENTION

The present disclosure relates to systems and methods for bioinformatics and data processing. In particular, the present disclosure relates to methods and systems for identifying unknown drug targets via adverse event data.

BACKGROUND OF THE INVENTION

Adverse event data from adverse event reporting systems (AERS) such as those maintained by the U.S. Food and Drug Association may be useful in statistically identifying potential drug hazards. However, analysis of such data is typically limited to simple univariate analysis, such as rates of adverse events associated with a medication. Such analysis may fail to examine other factors and associations between medications or relationships between molecular entities associated with the medications, such as target (and off-target) proteins, enzymes, transporters, pathways, drug classes, or other information.

BRIEF SUMMARY OF THE INVENTION

In one aspect, the present disclosure is directed to systems and methods for analysis of adverse event data. Adverse event data may be integrated with data regarding drug targets, classes of drugs or therapeutic categories, indications, target proteins, metabolizing enzymes or pathways, and may be analyzed on a molecular basis. Deciphering the molecular basis of such adverse responses is not only paramount to the protection of patient well-being and the development of safer drugs, but it also presents a unique opportunity to dissect disease systems in search of novel predictive biomarkers, drug targets and efficacious combination therapies.

In another aspect, the present disclosure is directed to systems and methods for identifying treatment strategies based on integrating drug molecular data and patient genome sequencing data with critical clinical information about the patient. Disaggregated data may be combined and translated into evidence-based treatment strategies for marketed and clinical stage therapies.

In still another aspect, the present disclosure is directed to systems and methods for clinical trial design based on integrated molecular data regarding adverse events, drug targets, classes of drugs or therapeutic categories, indications, target proteins, metabolizing enzymes or pathways, and may be analyzed on a molecular basis. Through analysis of adverse events at the level of drug target proteins, pathways, or metabolizing enzymes, trials may be designed to focus on specific adverse events while reducing false positives or negatives through drug interaction at the protein, pathway, or enzyme level. In some embodiments, adverse events for new drugs in development may be predicted through analysis of adverse event data for drugs with similar molecular interactions or targets.

Accordingly, in some embodiments, the systems and methods discussed herein may allow:

Integration of all patient-specific clinical information and molecular testing results into a single decision support framework;

Automated patient genome analysis and functional prioritization of variants;

Conversion and visualizations of clinical data and patient-specific therapeutic system models;

Conversion of clinical data into an easy-to-view representation of a patient's treatment history;

Identification of off-target safety, resistance, or other clinical effects (e.g. improved response, lower death rate, etc.) via analysis of the molecular basis of adverse events;

Safety signal detection and analysis of potentially causative molecular mechanisms;

Analysis of adverse events data for drugs, drug classes, targets, or pathways;

Integration of adverse event reports with relevant clinical and molecular knowledge; and Capturing of proprietary outcomes data, permitting novel insights into clinical trial and adverse drug event management program results.

In one aspect, the present disclosure is directed to systems and methods for analysis of adverse event data. Adverse event data may be integrated with data regarding drug targets, classes of drugs or therapeutic categories, indications, target proteins, metabolizing enzymes or pathways, and may be analyzed on a molecular basis. Deciphering the molecular basis of such adverse responses is not only paramount to the protection of patient well-being and the development of safer drugs, but it also presents a unique opportunity to dissect disease systems in search of novel biomarkers, drug targets and efficacious combination therapies. Adverse event information may be combined with clinico-molecular knowledge about drug activity within a patient. A user, drug manufacturer, patient, or medical service provider may explore and analyze adverse event information from both statistical and molecular perspectives. In some embodiments, the system may comprise analytical and visualization tools supporting the expedited detection and validation of drug-related safety science.

In another aspect, the present disclosure is directed to systems and methods for identifying treatment strategies based on integrating drug molecular data and patient genome sequencing data with critical clinical information about the patient. Disaggregated data may be combined and translated into evidence-based treatment strategies for marketed and clinical stage therapies.

In still another aspect, the present disclosure is directed to systems and methods for clinical trial design based on integrated molecular data regarding adverse events, drug targets, classes of drugs or therapeutic categories, indications, target proteins, metabolizing enzymes or pathways, and may be analyzed on a molecular basis. Through analysis of adverse events at the level of drug target proteins, pathways, or metabolizing enzymes, trials may be designed to avoid specific adverse events while reducing false positives or negatives through drug interaction at the protein, pathway, or enzyme level. In some embodiments, adverse events for new drugs in development may be predicted through analysis of adverse event data for drugs with similar metabolic interactions or targets.

In one aspect, the present disclosure is directed to a method for identifying molecular entities potentially responsible for adverse event differences between similar indications. The method includes receiving, by an input module executed by a processor of a computing device from a user, an identification of a first indication and a second indication similar to the first indication, and an identification of an adverse event. The method also includes retrieving, by an analyzer executed by the processor of the computing device from an adverse event database, a first list of medications prescribed to patients with the first indication who experienced the identified adverse event, and a second list of medications associated with the second indication who experienced the identified adverse event, each of the first list and second list comprising percentages of adverse event-experiencing patients prescribed each medication. The method further includes identifying, by the analyzer, a medication included in the first list of medications and the second list of medications, the medication associated with a different percentage value in each list. The method also includes retrieving, by the analyzer from a medication information database, a third list of molecular entities associated with the identified medication, responsive to identifying the medication as associated with a different percentage value in each list. The method also includes presenting, by an output module executed by the processor of the computing device to the user, the third list as a list of molecular entities potentially affected by only one of the first indication and second indication.

In one embodiment of the method, receiving an identification of a first indication, a second indication, and an adverse event includes receiving, from a second computing device via a network, the identification of the first indication and the second indication similar to the first indication, and he identification of the adverse event. In another embodiment of the method, the second indication includes a second indication associated with an organ associated with the first indication. In some embodiments of the method, retrieving a first list of medications and a second list of medications includes, for each list: extracting, from the adverse event database, a subset of adverse event records comprising an identification of the indication for the list and an identification of the adverse event; for each medication identified in a record in the extracted subset of adverse event records, counting a number of records in the extracted subset of adverse event records comprising an identification of the medication; and generating a list of the medications identified in the extracted subset of adverse event records, the list comprising the count associated with each medication. In a further embodiment, the method includes, for each medication, identifying a percentage of records in the extracted subset of adverse event records including identification of the medication, the identified percentage corresponding to each medication included in each list. In a still further embodiment of the method, identifying a medication having a different percentage in each list includes identifying a medication listed in both the first list and second list; determining a difference between the identified percentage corresponding to the medication in the first list and the identified percentage corresponding to the medication in the second list exceeds a predetermined threshold; and responsive to the determination, identifying the medication as having a different percentage.

In some embodiments, the method includes identifying a second medication included in the first list and second list having a different percentage in each list. The method also includes retrieving a fourth list of molecular entities associated with the identified medication. The method further includes merging the third list and fourth list to generate a combined list of molecular entities potentially affected by only one of the first indication and second indication. In a further embodiment, the method includes scoring each molecular entity in the combined list with a candidate score; and increasing the score of a molecular entity, responsive to its presence in both the third list and fourth list. In a still further embodiment, the method includes presenting the combined list, ordered by candidate score, as a prioritized list of molecular entities potentially affected by only one of the first indication and second indication.

In another aspect, the present disclosure is direct to a system for identifying molecular entities potentially responsible for adverse event differences between similar indications. The system includes a computing device, comprising a processor configured to execute an input module, an analyzer, and an output module. The input module may be configured to receive, from a user, an identification of a first indication and a second indication similar to the first indication, and an identification of an adverse event. The analyzer may be configured to retrieve, from an adverse event database, a first list of medications prescribed to patients with the first indication who experienced the identified adverse event, and a second list of medications associated with the second indication who experienced the identified adverse event, each of the first list and second list comprising percentages of adverse event-experiencing patients prescribed each medication; identify a medication included in the first list of medications and the second list of medications, the medication associated with a different percentage value in each list; and retrieve, from a medication information database, a third list of molecular entities associated with the identified medication, responsive to identifying the medication as associated with a different percentage value in each list. The output module may be configured to present, to the user, the third list as a list of molecular entities potentially affected by only one of the first indication and second indication.

In some embodiments of the system, the input module is configured to receive, from a second computing device via a network, the identification of the first indication and the second indication similar to the first indication, and he identification of the adverse event. In other embodiments of the system, the second indication similar to the first indication comprises a second indication associated with an organ associated with the first indication.

In one embodiment of the system, the analyzer is further configured, for each list, to: extract, from the adverse event database, a subset of adverse event records comprising an identification of the indication for the list and an identification of the adverse event; for each medication identified in a record in the extracted subset of adverse event records, count a number of records in the extracted subset of adverse event records comprising an identification of the medication; and generate a list of the medications identified in the extracted subset of adverse event records, the list comprising the count associated with each medication. In a further embodiment, the analyzer is further configured to, for each medication, identify a percentage of records in the extracted subset of adverse event records including identification of the medication, the identified percentage corresponding to each medication included in each list. In a still further embodiment, the analyzer is further configured to: identify a medication listed in both the first list and second list; determine a difference between the identified percentage corresponding to the medication in the first list and the identified percentage corresponding to the medication in the second list exceeds a predetermined threshold; and responsive to the determination, identify the medication as having a different percentage.

In some embodiments, the analyzer is further configured to: identify a second medication included in the first list and second list having a different percentage in each list; retrieve a fourth list of molecular entities associated with the identified medication. In some such embodiments, presenting the third list includes merging the third list and fourth list to generate a combined list of molecular entities potentially affected by only one of the first indication and second indication. In a further embodiment, the analyzer is further configured to score each molecular entity in the combined list with a candidate score; and increase the score of a molecular entity, responsive to its presence in both the third list and fourth list. In a still further embodiment, presenting the third list further includes presenting the third list, ordered by candidate score, as a prioritized list of molecular entities potentially affected by only one of the first indication and second indication.

In another aspect, the present disclosure is directed to a method for identifying unknown drug targets via adverse event data. The method includes receiving, by an analyzer module executed by a processor of a computing device from a user, an identification of a first drug having one or more unknown target proteins. The method also includes identifying, by the analyzer module from a medication information database stored in a computer-readable storage medium, a second drug related to the first drug. The method further includes retrieving, by the analyzer module from an adverse event database stored in the computer-readable storage medium, a first side effect profile associated with the first drug, and a second side effect profile associated with the second drug. The method also includes generating, by the analyzer module, a third side effect profile comprising a subset of the first side effect profile not shared by the second side effect profile. The method also includes identifying, by the analyzer module from the adverse event database, a third drug having a fourth side effect profile comprising the third side effect profile. The method further includes retrieving, by the analyzer module from the medication information database, a list of one or more target proteins of the third drug not targeted by the second drug. The method also includes presenting, by the analyzer module via a display interface of the computing device to the user, the retrieved list of one or more target proteins as potential target proteins of the first drug.

In some embodiments of the method, the second drug is in the same class as the first drug. In other embodiments of the method, the first drug and second drug are identified as binding to the same target protein. In still other embodiments of the method, each of the first, second, and fourth side effect profiles comprise a statistical index of side effects experienced by consumers of the corresponding first, second, and third drugs.

In one embodiment, the method includes subtracting a frequency of occurrence of a side effect in the second side effect profile from a frequency of occurrence of the side effect in the first side effect profile. In another embodiment, the method includes identifying a side effect with a first frequency of occurrence in the first side effect profile and a second frequency of occurrence in the second side effect profile. In a further embodiment, the method includes excluding the identified side effect from the third side effect profile, responsive to the first frequency of occurrence being within a predetermined threshold from the second frequency of occurrence. In another further embodiment, the method includes including the identified side effect in the third side effect profile, responsive the first frequency of occurrence being outside a predetermined threshold from the second frequency of occurrence. In some embodiments, the method includes identifying a side effect with a first frequency of occurrence in the third side effect profile and a second frequency of occurrence in the fourth side effect profile, the first frequency of occurrence and second frequency of occurrence being within a predetermined threshold.

In yet another aspect, the present disclosure is directed to a system for identifying unknown drug targets via adverse event data. The system includes a computing device, in communication with a computer-readable storage medium comprising an adverse event database and a medication information database. The computing device includes a display interface and a processor executing an analyzer module. The analyzer module is configured for receiving, from a user, an identification of a first drug having one or more unknown target proteins; and identifying, from the medication information database, a second drug related to the first drug. The analyzer module is also configured for retrieving, from the adverse event database, a first side effect profile associated with the first drug, and a second side effect profile associated with the second drug; and generating a third side effect profile comprising a subset of the first side effect profile not shared by the second side effect profile. The analyzer module is further configured for identifying, from the adverse event database, a third drug having a fourth side effect profile comprising the third side effect profile; and retrieving, from the medication information database, a list of one or more target proteins of the third drug not targeted by the second drug. The computing device is configured for presenting, via the display interface to the user, the retrieved list of one or more target proteins as potential target proteins of the first drug.

In some embodiments of the system, the second drug is in the same class as the first drug. In other embodiments of the system, the first drug and second drug are identified as binding to the same target protein. In still other embodiments of the system, each of the first, second, and fourth side effect profiles comprise a statistical index of side effects experienced by consumers of the corresponding first, second, and third drugs.

In one embodiment, the analyzer module is further configured for subtracting a frequency of occurrence of a side effect in the second side effect profile from a frequency of occurrence of the side effect in the first side effect profile. In another embodiment, the analyzer module is further configured for identifying a side effect with a first frequency of occurrence in the first side effect profile and a second frequency of occurrence in the second side effect profile. In a further embodiment, the analyzer module is further configured for excluding the identified side effect from the third side effect profile, responsive to the first frequency of occurrence being within a predetermined threshold from the second frequency of occurrence. In another further embodiment, the analyzer module is further configured for including the identified side effect in the third side effect profile, responsive the first frequency of occurrence being outside a predetermined threshold from the second frequency of occurrence. In some embodiments, the analyzer module is further configured for identifying a side effect with a first frequency of occurrence in the third side effect profile and a second frequency of occurrence in the fourth side effect profile, the first frequency of occurrence and second frequency of occurrence being within a predetermined threshold.

The details of various embodiments of the invention are set forth in the accompanying drawings and the description below.

BRIEF DESCRIPTION OF THE FIGURES

The foregoing and other objects, aspects, features, and advantages of the disclosure will become more apparent and better understood by referring to the following description taken in conjunction with the accompanying drawings, in which.

Figure 1A:
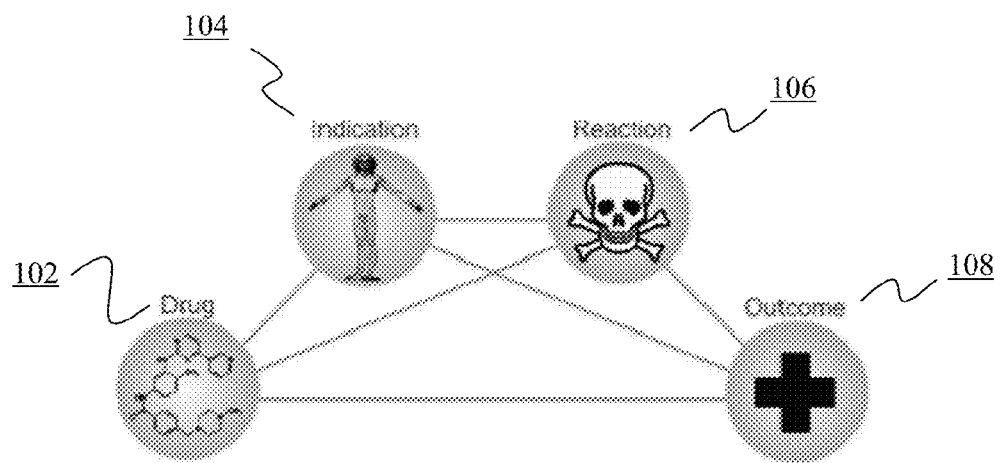
FIG. 1A is a block diagram depicting relationships between data provided by embodiments of an adverse event reporting system.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION OF THE INVENTION

Adverse events are a common and, for the most part, unavoidable consequence of therapeutic intervention. The identification of novel adverse events is critical to the protection of patient well-being and the healthcare system that supports them. From the induction of avoidable and sometimes fatal side effects to the billions of dollars in associated medical costs, adverse events (AE's) remain a critical issue for all stakeholders in the healthcare system.

Data about adverse events are provided by clinicians, researchers, and manufacturers to spontaneous reporting systems, such as the U.S. Food and Drug Administration's Adverse Event Reporting System (AERS). After a manual review of each submission the data are made publically available on quarterly basis via the online AERS data files. All reports contain information surrounding the treatment, side effects, and patient characteristics/demographics. Drug information is further qualified as to whether the drug is suspected as the primary or secondary cause of the adverse event or whether it was concomitant. However, there are a number of considerations that limit the usefulness of the AERS data for pharmacovigilance purposes. Traditional methods of Adverse Drug Reaction (ADR) detection have often relied on the manual review of drug-specific cases by clinical pharmacologists. However, the increasing size and complexity of SRS databases, and limitations in human resources have led to demands for more efficient methods of ADR detection. Additionally, AERS data is frequently difficult to use, with misspellings, abbreviations, and inconsistent synonyms used. Furthermore, as adverse event reporting systems focus on adverse events and drugs, detailed molecular information is absent. For example, referring briefly to FIG. 1A, adverse event data typically includes identifications of drugs prescribed to a patient 102; indications 104, or diseases or symptoms for which the drug or drugs was prescribed; reactions or side effects 106; and outcomes 108. For example, an outcome 108 may comprise prolonged hospitalization, short term hospitalization, or death. Accordingly, while the data may be useful for identifying drug-drug interactions, or performing univariate analysis, such as the statistical percentage of patients taking a drug that had a particular outcome when experiencing an adverse event, the data may be limited in utility on its own.

Figure 1B:
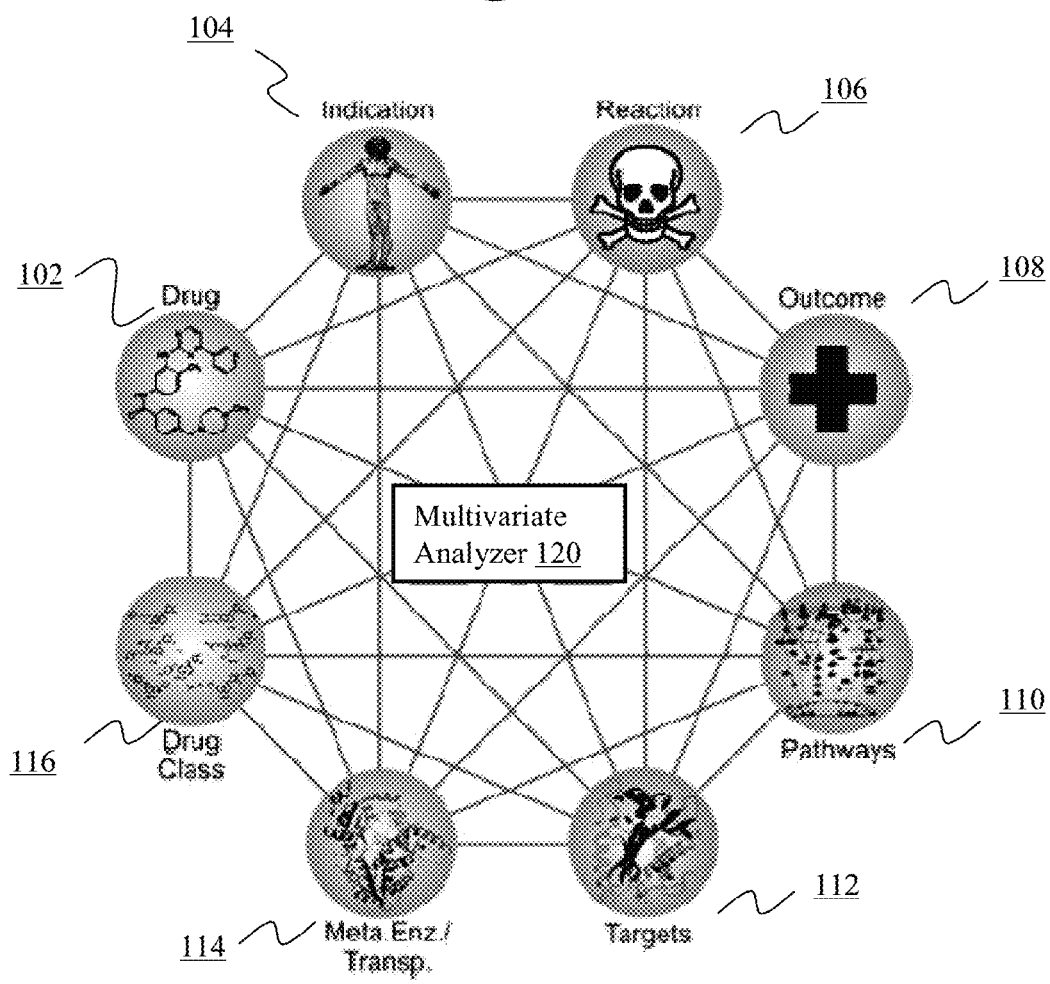
FIG. 1B is a block diagram depicting relationships between molecular entities in an embodiment of a multivariate analysis system.

The systems and methods discussed herein provide for multivariate analysis of molecular entities involved with adverse events. Referring briefly to FIG. 1B and in contradistinction from FIG. 1A, a multivariate analyzer 120 may utilize links between not just drugs 102, indications 104, reactions 106, and outcomes 108, but molecular entities such as pathways 110, protein targets 112, metabolizing enzymes or transporters 114. Drugs 102 may also be associated with a drug class 116. This enables investigation of the relationship between, say, a particular side effect or reaction 106 and a protein target 112, or other entity types such as protein domains, gene ontology terms for biological processes, and other biological, chemical, or clinical descriptors. Deciphering the molecular basis of such adverse responses is not only paramount to the protection of patient well-being and the development of safer drugs, but it also presents a unique opportunity to dissect disease systems in search of novel predictive biomarkers, drug targets and efficacious combination therapies.

Prior to discussing specifics of methods and systems utilizing multivariate analysis of adverse event data, it may be helpful to briefly define a few terms as used herein. The following definitions are not intended to be limiting, but may comprise alternate definitions commonly utilized by those of ordinary skill in the art. Accordingly, context may clarify whether, for example, the term indication refers to a symptom or disease, a flag in a database, or a selection by a user. Additionally, the following list of definitions is not intended to be exhaustive, but rather discuss a few key terms that may be helpful to those of skill in the art.

Adverse event: In pharmacology, an adverse event may refer to any unexpected or dangerous reaction to a drug. An unwanted effect caused by the administration of a drug. The onset of the adverse reaction may be sudden or develop over time. Also interchangeably called: adverse drug event (ADE), adverse drug reaction (ADR), adverse effect or adverse reaction.

Absorption, Distribution, Metabolism, Excretion (ADME): Refers to the standard pharmacokinetic mechanism of a drug (see Pharmacokinetics).

AERS—Adverse Event Reporting System: The Adverse Event Reporting System (AERS) is a computerized information database designed to support the FDA's post-marketing safety surveillance program for all approved drug and therapeutic biologic products. The FDA uses AERS to monitor for new adverse events and medication errors that might occur with these marketed products.

Bioavailability: Also referred to as availability, this is the amount of a drug that is absorbed into circulation after administration of a specific dosage.

Challenge-dechallenge-rechallenge (CDR): This is a medical testing protocol in which a medicine (or drug) is administered (challenge), withdrawn (dechallenge), then re-administered (rechallenge), while being monitored for adverse effects (reactions) at each stage.

Contingency table (or matrix): Also referred to as cross tabulation or cross tab. A contingency table is often used to record and analyze the relation between two or more categorical variables. It displays the (multivariate) frequency distribution of the variables in a matrix format.

Drug interaction: A drug interaction is a situation in which a substance affects the activity of a drug, i.e. the effects are increased or decreased, or they produce a new effect that neither produces on its own. However, interactions may also exist between drugs & foods (drug-food interactions), as well as drugs & herbs (drug-herb interactions). These may occur out of accidental misuse or due to lack of knowledge about the active ingredients involved in the relevant substances or the underlying molecular mechanisms.

Entity Coverage/Co-Entity Coverage: The Entity Coverage is an estimate that refers to the significance with which a first entity (E1) is related with a second entity (E2) in a data set. It is the calculated from the number of data entries containing E1 and E2 divided by the overall number of data entries containing E1. The Co-Entity Coverage is the calculated from the number of data entries containing E1 and E2 divided by the overall number of data entries containing E2. This method gives thus an indication for the significance of entity relations in subsets of data.

Gamma Poisson Shrinker: Advanced method for Pharmacovigilance Signal Detection. In contrast to simple methods that focus on a specific AE-drug-combination at a time (encoded in 2*2 contingency tables), it can directly use contingency tables that range over all drugs and AEs.

Idiosyncratic response: An abnormal response from a drug that is specific to the person having the response.

Indication (or 'drug use'): In medicine, an indication is a valid reason to use a certain test, medication, procedure, or surgery. An indication may thus refer to a disease, a symptom, or diagnosis. The opposite of indication is contraindication.

Metabolizing enzyme: A protein that metabolizes a medication; the enzyme may help transforming a pro-drug to its pharmacologically active chemical compound form or it may play a role in its degradation.

Molecular mechanism: The flow of events that take place in the molecular level when a drug is administered. The molecular mechanisms can be highly complex due to the variety of participating components (e.g., drugs, organs, cells, proteins, etc.), systems (e.g., pathways, disease networks, etc.), entity interrelations (e.g., drug-target, drug-metabolizing enzyme, carriers, transporters, overlapping systems and pathways, etc.), and molecular aberrations (e.g., mutations, radiation damage, etc.). Components of the molecular mechanism, such as protein targets, pathways, transporters, drugs, or drug classes may be referred to variously as molecular entities or biomolecular entities.

Side effect: Any unintended effect of a pharmaceutical product occurring at a dose normally used in man, which is related to the pharmacological properties of the drug. A side effect may frequently correspond to an indication. For example, nausea may be a side effect of a first drug, but may be an indication to be treated by a second drug. A negative side effect may also be referred to as an adverse event.

Figure 2A:
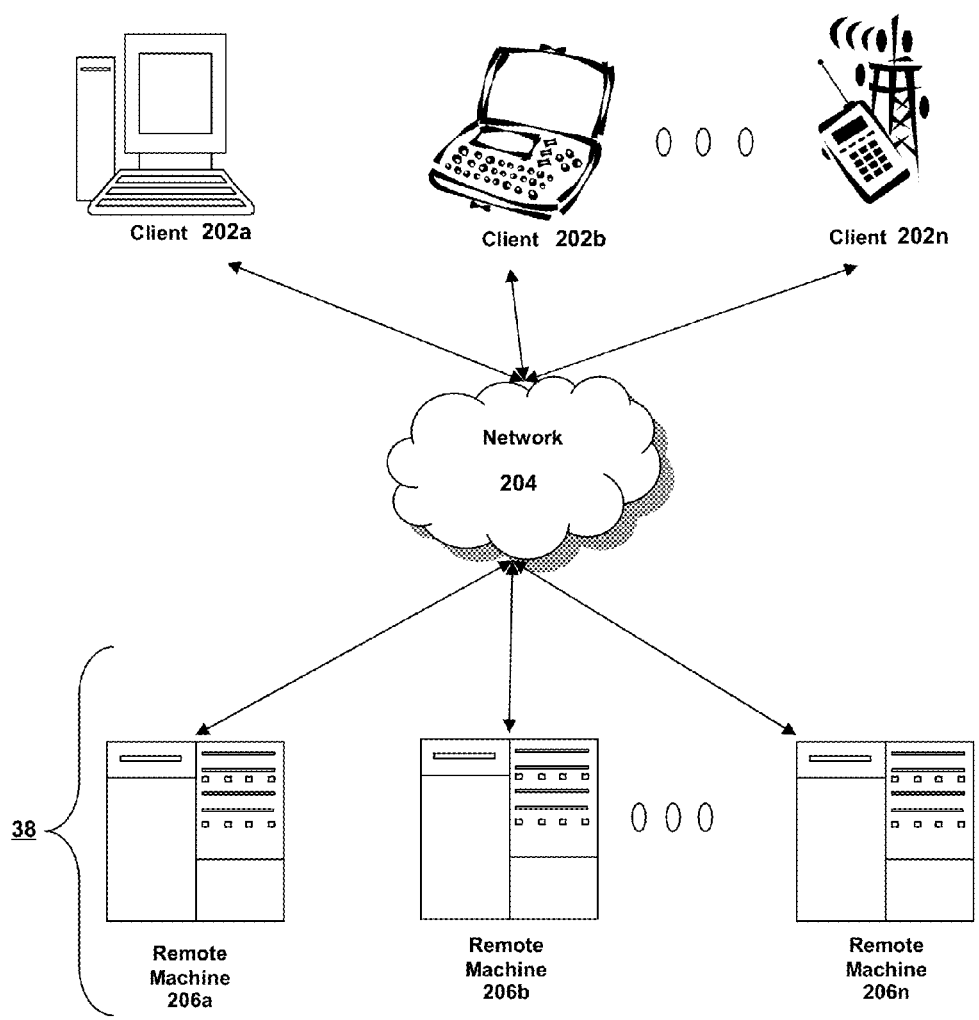
FIG. 2A is a block diagram depicting an embodiment of a network environment comprising local machines in communication with remote machines.

Prior to discussing specifics of methods and systems for multivariate analysis of adverse event data, it may be helpful to briefly discuss embodiments of networks and computing devices that may be utilized in various embodiments of these methods and systems. Referring now to FIG. 2A, an embodiment of a network environment is depicted. In brief overview, the network environment comprises one or more local machines 202a-202n (also generally referred to as local machine(s) 202, client(s) 202, client node(s) 202, client machine(s) 202, client computer(s) 202, client device(s) 202, endpoint(s) 202, or endpoint node(s) 202) in communication with one or more remote machines 206a-206n (also generally referred to as server(s) 206 or remote machine(s) 206) via one or more networks 204. In some embodiments, a local machine 202 has the capacity to function as both a client node seeking access to resources provided by a server and as a server providing access to hosted resources for other clients 202a-202n.

Although FIG. 2A shows a network 204 between the local machines 202 and the remote machines 206, the local machines 202 and the remote machines 206 may be on the same network 204. The network 204 can be a local-area network (LAN), such as a company Intranet, a metropolitan area network (MAN), or a wide area network (WAN), such as the Internet or the World Wide Web. In some embodiments, there are multiple networks 204 between the local machines 202 and the remote machines 206. In one of these embodiments, a network 204' (not shown) may be a private network and a network 204 may be a public network. In another of these embodiments, a network 204 may be a private network and a network 204' a public network. In still another embodiment, networks 204 and 204' may both be private networks. In yet another embodiment, networks 204 and 204' may both be public networks.

The network 204 may be any type and/or form of network and may include any of the following: a point to point network, a broadcast network, a wide area network, a local area network, a telecommunications network, a data communication network, a computer network, an ATM (Asynchronous Transfer Mode) network, a SONET (Synchronous Optical Network) network, a SDH (Synchronous Digital Hierarchy) network, a wireless network and a wireline network. In some embodiments, the network 204 may comprise a wireless link, such as an infrared channel or satellite band. The topology of the network 204 may be a bus, star, or ring network topology. The network 204 may be of any such network topology as known to those ordinarily skilled in the art capable of supporting the operations described herein. The network may comprise mobile telephone networks utilizing any protocol or protocols used to communicate among mobile devices, including AMPS, TDMA, CDMA, GSM, GPRS or UMTS. In some embodiments, different types of data may be transmitted via different protocols. In other embodiments, the same types of data may be transmitted via different protocols.

In some embodiments, the system may include multiple, logically-grouped remote machines 206. In one of these embodiments, the logical group of remote machines may be referred to as a server farm 38. In another of these embodiments, the remote machines 206 may be geographically dispersed. In other embodiments, a server farm 38 may be administered as a single entity. In still other embodiments, the server farm 38 comprises a plurality of server farms 38. The remote machines 206 within each server farm 38 can be heterogeneous—one or more of the remote machines 206 can operate according to one type of operating system platform (e.g., WINDOWS NT, WINDOWS 2003, WINDOWS 2008, WINDOWS 7 and WINDOWS Server 2008 R2, all of which are manufactured by Microsoft Corp. of Redmond, Wash.), while one or more of the other remote machines 206 can operate on according to another type of operating system platform (e.g., Unix or Linux).

The remote machines 206 of each server farm 38 do not need to be physically proximate to another remote machine 206 in the same server farm 38. Thus, the group of remote machines 206 logically grouped as a server farm 38 may be interconnected using a wide-area network (WAN) connection or a metropolitan-area network (MAN) connection. For example, a server farm 38 may include remote machines 206 physically located in different continents or different regions of a continent, country, state, city, campus, or room. Data transmission speeds between remote machines 206 in the server farm 38 can be increased if the remote machines 206 are connected using a local-area network (LAN) connection or some form of direct connection.

A remote machine 206 may be a file server, application server, web server, proxy server, appliance, network appliance, gateway, application gateway, gateway server, virtualization server, deployment server, SSL VPN server, or firewall. In some embodiments, a remote machine 206 provides a remote authentication dial-in user service, and is referred to as a RADIUS server. In other embodiments, a remote machine 206 may have the capacity to function as either an application server or as a master application server. In still other embodiments, a remote machine 206 is a blade server. In yet other embodiments, a remote machine 206 executes a virtual machine providing, to a user or client computer 202, access to a computing environment.

In one embodiment, a remote machine 206 may include an Active Directory. The remote machine 206 may be an application acceleration appliance. For embodiments in which the remote machine 206 is an application acceleration appliance, the remote machine 206 may provide functionality including firewall functionality, application firewall functionality, or load balancing functionality. In some embodiments, the remote machine 206 comprises an appliance such as one of the line of appliances manufactured by the Citrix Application Networking Group, of San Jose, Calif., or Silver Peak Systems, Inc., of Mountain View, Calif., or of Riverbed Technology, Inc., of San Francisco, Calif., or of F5 Networks, Inc., of Seattle, Wash., or of Juniper Networks, Inc., of Sunnyvale, Calif.

In some embodiments, a remote machine 206 executes an application on behalf of a user of a local machine 202. In other embodiments, a remote machine 206 executes a virtual machine, which provides an execution session within which applications execute on behalf of a user of a local machine 202. In one of these embodiments, the execution session is a hosted desktop session. In another of these embodiments, the execution session provides access to a computing environment, which may comprise one or more of: an application, a plurality of applications, a desktop application, and a desktop session in which one or more applications may execute.

In some embodiments, a local machine 202 communicates with a remote machine 206. In one embodiment, the local machine 202 communicates directly with one of the remote machines 206 in a server farm 38. In another embodiment, the local machine 202 executes a program neighborhood application to communicate with a remote machine 206 in a server farm 38. In still another embodiment, the remote machine 206 provides the functionality of a master node. In some embodiments, the local machine 202 communicates with the remote machine 206 in the server farm 38 through a network 204. Over the network 204, the local machine 202 can, for example, request execution of various applications hosted by the remote machines 206a-206n in the server farm 38 and receive output of the results of the application execution for display. In some embodiments, only a master node provides the functionality required to identify and provide address information associated with a remote machine 206b hosting a requested application.

In one embodiment, the remote machine 206 provides the functionality of a web server. In another embodiment, the remote machine 206a receives requests from the local machine 202, forwards the requests to a second remote machine 206b and responds to the request by the local machine 202 with a response to the request from the remote machine 206b. In still another embodiment, the remote machine 206a acquires an enumeration of applications available to the local machine 202 and address information associated with a remote machine 206b hosting an application identified by the enumeration of applications. In yet another embodiment, the remote machine 206 presents the response to the request to the local machine 202 using a web interface. In one embodiment, the local machine 202 communicates directly with the remote machine 206 to access the identified application. In another embodiment, the local machine 202 receives output data, such as display data, generated by an execution of the identified application on the remote machine 206.

In some embodiments, the remote machine 206 or a server farm 38 may be running one or more applications, such as an application providing a thin-client computing or remote display presentation application. In one embodiment, the remote machine 206 or server farm 38 executes as an application any portion of the CITRIX ACCESS SUITE by Citrix Systems, Inc., such as the METAFRAME or CITRIX PRESENTATION SERVER products, any of the following products manufactured by Citrix Systems, Inc.: CITRIX XENAPP, CITRIX XENDESKTOP, CITRIX ACCESS GATEWAY, and/or any of the MICROSOFT WINDOWS Terminal Services manufactured by the Microsoft Corporation. In another embodiment, the application is an ICA client, developed by Citrix Systems, Inc. of Fort Lauderdale, Fla. In still another embodiment, the remote machine 206 may run an application, which, for example, may be an application server providing email services such as MICROSOFT EXCHANGE manufactured by the Microsoft Corporation of Redmond, Wash., a web or Internet server, or a desktop sharing server, or a collaboration server. In yet another embodiment, any of the applications may comprise any type of hosted service or products, such as GOTOMEETING provided by Citrix Online Division, Inc. of Santa Barbara, Calif., WEBEX provided by WebEx, Inc. of Santa Clara, Calif., or Microsoft Office LIVE MEETING provided by Microsoft Corporation of Redmond, Wash.

A local machine 202 may execute, operate or otherwise provide an application, which can be any type and/or form of software, program, or executable instructions such as any type and/or form of web browser, web-based client, client-server application, a thin-client computing client, an ActiveX control, or a Java applet, or any other type and/or form of executable instructions capable of executing on local machine 202. In some embodiments, the application may be a server-based or a remote-based application executed on behalf of the local machine 202 on a remote machine 206. In other embodiments, the remote machine 206 may display output to the local machine 202 using any thin-client protocol, presentation layer protocol, or remote-display protocol, such as the Independent Computing Architecture (ICA) protocol manufactured by Citrix Systems, Inc. of Ft. Lauderdale, Fla.; the Remote Desktop Protocol (RDP) manufactured by the Microsoft Corporation of Redmond, Wash.; the X11 protocol; the Virtual Network Computing (VNC) protocol, manufactured by AT&T Bell Labs; the SPICE protocol, manufactured by Qumranet, Inc., of Sunnyvale, Calif., USA, and of Raanana, Israel; the Net2Display protocol, manufactured by VESA, of Milpitas, Calif.; the PC-over-IP protocol, manufactured by Teradici Corporation, of Burnaby, B.C.; the TCX protocol, manufactured by Wyse Technology, Inc., of San Jose, Calif.; the THINC protocol developed by Columbia University in the City of New York, of New York, N.Y.; or the Virtual-D protocols manufactured by Desktone, Inc., of Chelmsford, Mass. The application can use any type of protocol and it can be, for example, an HTTP client, an FTP client, an Oscar client, or a Telnet client. In still other embodiments, the application comprises any type of software related to voice over Internet protocol (VoIP) communications, such as a soft IP telephone. In further embodiments, the application comprises any application related to real-time data communications, such as applications for streaming video and/or audio.

Figure 2B:
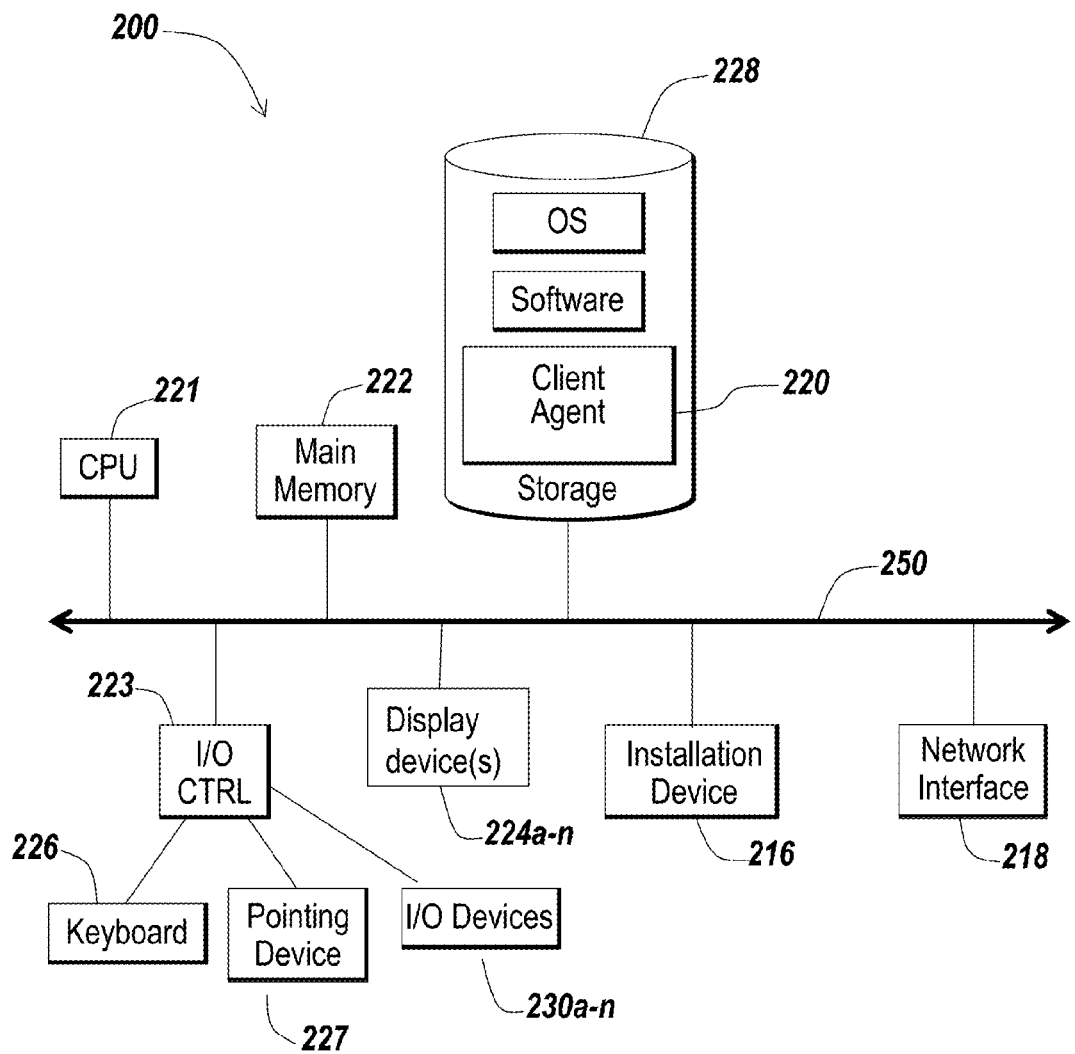
FIGS. 2B-2E are block diagrams depicting embodiments of computers useful in connection with the methods and systems described herein.
Figure 2C:
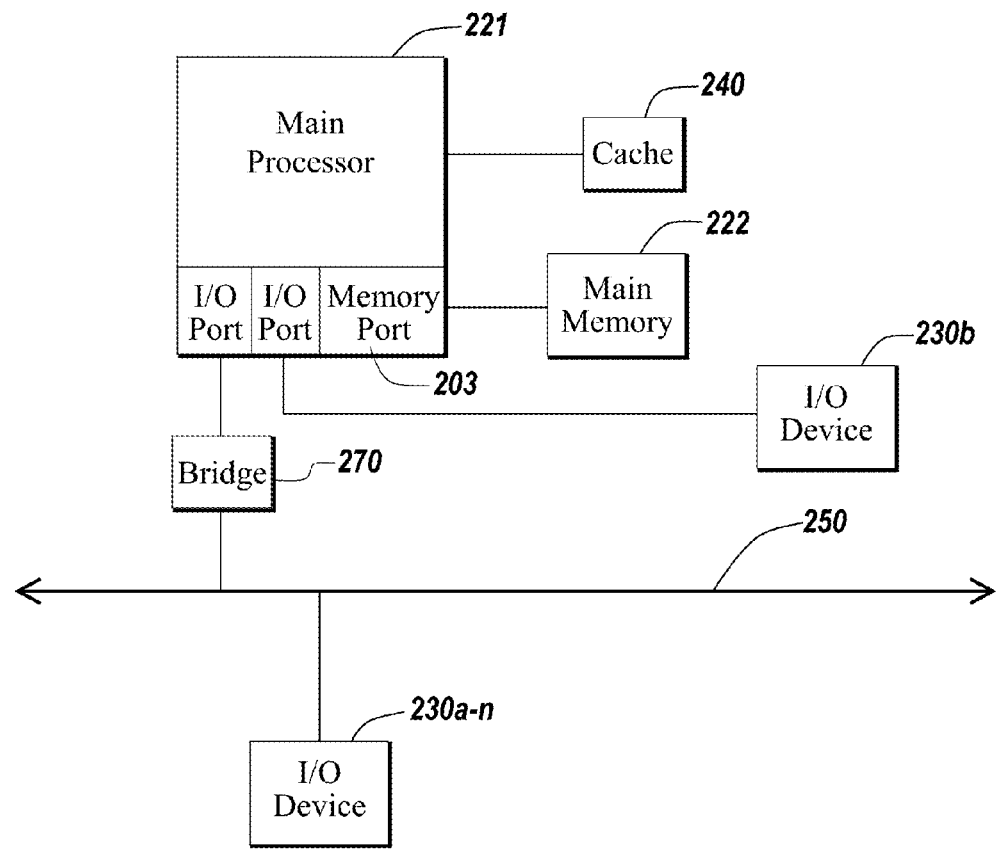

The local machine 202 and remote machine 206 may be deployed as and/or executed on any type and form of computing device, such as a computer, network device or appliance capable of communicating on any type and form of network and performing the operations described herein. FIGS. 2B and 2C depict block diagrams of a computing device 200 useful for practicing an embodiment of the local machine 202 or a remote machine 206. As shown in FIGS. 2B and 2C, each computing device 200 includes a central processing unit 221, and a main memory unit 222. As shown in FIG. 2B, a computing device 200 may include a storage device 228, an installation device 216, a network interface 218, an I/O controller 223, display devices 224a-n, a keyboard 226 and a pointing device 227, such as a mouse. The storage device 228 may include, without limitation, an operating system, software, and a client agent 220. As shown in FIG. 2C, each computing device 200 may also include additional optional elements, such as a memory port 203, a bridge 270, one or more input/output devices 230a-230n (generally referred to using reference numeral 230), and a cache memory 240 in communication with the central processing unit 221.

The central processing unit 221 is any logic circuitry that responds to and processes instructions fetched from the main memory unit 222. In many embodiments, the central processing unit 221 is provided by a microprocessor unit, such as: those manufactured by Intel Corporation of Mountain View, Calif.; those manufactured by Motorola Corporation of Schaumburg, Ill.; those manufactured by Transmeta Corporation of Santa Clara, Calif.; the RS/6000 processor, those manufactured by International Business Machines of White Plains, N.Y.; or those manufactured by Advanced Micro Devices of Sunnyvale, Calif. The computing device 200 may be based on any of these processors, or any other processor capable of operating as described herein.

Main memory unit 222 may be one or more memory chips capable of storing data and allowing any storage location to be directly accessed by the microprocessor 221, such as Static random access memory (SRAM), Burst SRAM or SynchBurst SRAM (BSRAM), Dynamic random access memory (DRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Enhanced DRAM (EDRAM), synchronous DRAM (SDRAM), JEDEC SRAM, PC100 SDRAM, Double Data Rate SDRAM (DDR SDRAM), Enhanced SDRAM (ESDRAM), SyncLink DRAM (SLDRAM), Direct Rambus DRAM (DRDRAM), or Ferroelectric RAM (FRAM). The main memory 222 may be based on any of the above described memory chips, or any other available memory chips capable of operating as described herein. In the embodiment shown in FIG. 2B, the processor 221 communicates with main memory 222 via a system bus 250 (described in more detail below). FIG. 2C depicts an embodiment of a computing device 200 in which the processor communicates directly with main memory 222 via a memory port 203. For example, in FIG. 2C the main memory 222 may be DRDRAM.

FIG. 2C depicts an embodiment in which the main processor 221 communicates directly with cache memory 240 via a secondary bus, sometimes referred to as a backside bus. In other embodiments, the main processor 221 communicates with cache memory 240 using the system bus 250. Cache memory 240 typically has a faster response time than main memory 222 and is typically provided by SRAM, BSRAM, or EDRAM. In the embodiment shown in FIG. 2B, the processor 221 communicates with various I/O devices 230 via a local system bus 250. Various buses may be used to connect the central processing unit 221 to any of the I/O devices 230, including a VESA VL bus, an ISA bus, an EISA bus, a MicroChannel Architecture (MCA) bus, a PCI bus, a PCI-X bus, a PCI-Express bus, or a NuBus. For embodiments in which the I/O device is a video display 224, the processor 221 may use an Advanced Graphics Port (AGP) to communicate with the display 224. FIG. 2C depicts an embodiment of a computer 200 in which the main processor 221 communicates directly with I/O device 230b via HYPERTRANSPORT, RAPIDIO, or INFINIBAND communications technology. FIG. 2C also depicts an embodiment in which local busses and direct communication are mixed: the processor 221 communicates with I/O device 230a using a local interconnect bus while communicating with I/O device 230b directly.

A wide variety of I/O devices 230a-230n may be present in the computing device 200. Input devices include keyboards, mice, trackpads, trackballs, microphones, and drawing tablets. Output devices include video displays, speakers, inkjet printers, laser printers, and dye-sublimation printers. An I/O controller 223, as shown in FIG. 2B, may control the I/O devices. The I/O controller may control one or more I/O devices such as a keyboard 226 and a pointing device 227, e.g., a mouse or optical pen. Furthermore, an I/O device may also provide storage and/or an installation medium 216 for the computing device 200. In still other embodiments, the computing device 200 may provide USB connections (not shown) to receive handheld USB storage devices such as the USB Flash Drive line of devices manufactured by Twintech Industry, Inc. of Los Alamitos, Calif.

Referring again to FIG. 2B, the computing device 200 may support any suitable installation device 216, such as a floppy disk drive for receiving floppy disks such as 3.5-inch, 5.25-inch disks or ZIP disks, a CD-ROM drive, a CD-R/RW drive, a DVD-ROM drive, tape drives of various formats, USB device, hard-drive or any other device suitable for installing software and programs. The computing device 200 may further comprise a storage device, such as one or more hard disk drives or redundant arrays of independent disks, for storing an operating system and other related software, and for storing application software programs such as any program related to the client agent 220. Optionally, any of the installation devices 216 could also be used as the storage device. Additionally, the operating system and the software can be run from a bootable medium, for example, a bootable CD, such as KNOPPIX, a bootable CD for GNU/Linux that is available as a GNU/Linux distribution from knoppix.net.

Furthermore, the computing device 200 may include a network interface 218 to interface to the network 204 through a variety of connections including, but not limited to, standard telephone lines, LAN or WAN links (e.g., 802.11, T1, T3, 56kb, X.25, SNA, DECNET), broadband connections (e.g., ISDN, Frame Relay, ATM, Gigabit Ethernet, Ethernet-over-SONET), wireless connections, or some combination of any or all of the above. Connections can be established using a variety of communication protocols (e.g., TCP/IP, IPX, SPX, NetBIOS, Ethernet, ARCNET, SONET, SDH, Fiber Distributed Data Interface (FDDI), RS232, IEEE 802.11, IEEE 802.11a, IEEE 802.11b, IEEE 802.11g, CDMA, GSM, WiMax and direct asynchronous connections). In one embodiment, the computing device 200 communicates with other computing devices 200' via any type and/or form of gateway or tunneling protocol such as Secure Socket Layer (SSL) or Transport Layer Security (TLS), or the Citrix Gateway Protocol manufactured by Citrix Systems, Inc. of Ft. Lauderdale, Fla. The network interface 218 may comprise a built-in network adapter, network interface card, PCMCIA network card, card bus network adapter, wireless network adapter, USB network adapter, modem or any other device suitable for interfacing the computing device 200 to any type of network capable of communication and performing the operations described herein.

In some embodiments, the computing device 200 may comprise or be connected to multiple display devices 224a-224n, which each may be of the same or different type and/or form. As such, any of the I/O devices 230a-230n and/or the I/O controller 223 may comprise any type and/or form of suitable hardware, software, or combination of hardware and software to support, enable or provide for the connection and use of multiple display devices 224a-224n by the computing device 200. For example, the computing device 200 may include any type and/or form of video adapter, video card, driver, and/or library to interface, communicate, connect or otherwise use the display devices 224a-224n. In one embodiment, a video adapter may comprise multiple connectors to interface to multiple display devices 224a-224n. In other embodiments, the computing device 200 may include multiple video adapters, with each video adapter connected to one or more of the display devices 224a-224n. In some embodiments, any portion of the operating system of the computing device 200 may be configured for using multiple displays 224a-224n. In other embodiments, one or more of the display devices 224a-224n may be provided by one or more other computing devices, such as computing devices 200a and 200b connected to the computing device 200, for example, via a network. These embodiments may include any type of software designed and constructed to use another computer's display device as a second display device 224a for the computing device 200. One ordinarily skilled in the art will recognize and appreciate the various ways and embodiments that a computing device 200 may be configured to have multiple display devices 224a-224n.

In further embodiments, an I/O device 230 may be a bridge between the system bus 250 and an external communication bus, such as a USB bus, an Apple Desktop Bus, an RS-232 serial connection, a SCSI bus, a FireWire bus, a FireWire 800 bus, an Ethernet bus, an AppleTalk bus, a Gigabit Ethernet bus, an Asynchronous Transfer Mode bus, a HIPPI bus, a Super HIPPI bus, a SerialPlus bus, a SCI/LAMP bus, a FibreChannel bus, or a Serial Attached small computer system interface bus, or any other type and form of communication bus.

A computing device 200 of the sort depicted in FIGS. 2B and 2C typically operates under the control of operating systems, which control scheduling of tasks and access to system resources. The computing device 200 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 3.x, WINDOWS 95, WINDOWS 98, WINDOWS 2000, WINDOWS NT 3.51, WINDOWS NT 4.0, WINDOWS 7, WINDOWS CE, WINDOWS XP, and WINDOWS VISTA, all of which are manufactured by Microsoft Corporation of Redmond, Wash.; MAC OS, manufactured by Apple Inc., of Cupertino, Calif.; OS/2, manufactured by International Business Machines of Armonk, N.Y.; and Linux, a freely-available operating system distributed by Caldera Corp. of Salt Lake City, Utah, or any type and/or form of a Unix operating system, among others.

The computing device 200 can be any workstation, desktop computer, laptop or notebook computer, server, handheld computer, mobile telephone or other portable telecommunication device, media playing device, a gaming system, mobile computing device, or any other type and/or form of computing, telecommunications or media device that is capable of communication and that has sufficient processor power and memory capacity to perform the operations described herein. In some embodiments, the computing device 200 may have different processors, operating systems, and input devices consistent with the device. For example, in one embodiment, the computing device 200 is a TREO 180, 270, 600, 650, 680, 700p, 700w/wx, 750, 755p, 800w, Centro, or Pro smart phone manufactured by Palm, Inc. In some of these embodiments, the TREO smart phone is operated under the control of the PalmOS operating system and includes a stylus input device as well as a five-way navigator device.

In other embodiments the computing device 200 is a mobile device, such as a JAVA-enabled cellular telephone or personal digital assistant (PDA), such as the i55sr, i58sr, i85s, i88s, i90c, i95cl, i335, i365, i570, 1576, i580, i615, i760, i836, i850, i870, i880, i920, i930, ic502, ic602, ic902, i776 or the im1100, all of which are manufactured by Motorola Corp. of Schaumburg, Ill., the 6035 or the 7135, manufactured by Kyocera of Kyoto, Japan, or the i300 or i330, manufactured by Samsung Electronics Co., Ltd., of Seoul, Korea. In some embodiments, the computing device 200 is a mobile device manufactured by Nokia of Finland, or by Sony Ericsson Mobile Communications AB of Lund, Sweden.

In still other embodiments, the computing device 200 is a Blackberry handheld or smart phone, such as the devices manufactured by Research In Motion Limited, including the Blackberry 7100 series, 8700 series, 7700 series, 7200 series, the Blackberry 7520, the Blackberry PEARL 8100, the 8700 series, the 8800 series, the Blackberry Storm, Blackberry Bold, Blackberry Curve 8900, and the Blackberry Pearl Flip. In yet other embodiments, the computing device 200 is a smart phone, Pocket PC, Pocket PC Phone, or other handheld mobile device supporting Microsoft Windows Mobile Software. Moreover, the computing device 200 can be any workstation, desktop computer, laptop or notebook computer, server, handheld computer, mobile telephone, any other computer, or other form of computing or telecommunications device that is capable of communication and that has sufficient processor power and memory capacity to perform the operations described herein.

In some embodiments, the computing device 200 comprises a combination of devices, such as a mobile phone combined with a digital audio player or portable media player. In one of these embodiments, the computing device 200 is a Motorola RAZR or Motorola ROKR line of combination digital audio players and mobile phones. In another of these embodiments, the computing device 200 is a device in the iPhone line of smartphones, manufactured by Apple Inc., of Cupertino, Calif. In still other embodiments, the computing device 200 may comprise a tablet computer, such as an iPad tablet computer manufactured by Apple, Inc., or any other type and form of tablet computer.

In one embodiment, a computing device 202a may request resources from a remote machine 206, while providing the functionality of a remote machine 206 to a client 202b. In such an embodiment, the computing device 202a may be referred to as a client with respect to data received from the remote machine 206 (which may be referred to as a server) and the computing device 202a may be referred to as a server with respect to the second client 202b. In another embodiment, the client 202 may request resources from the remote machine 206 on behalf of a user of the client 202.

Figure 2D:
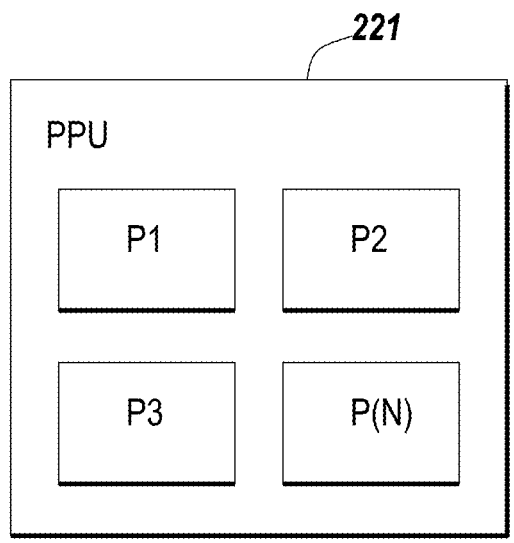

As shown in FIG. 2D, the computing device 200 may comprise multiple processors and may provide functionality for simultaneous execution of instructions or for simultaneous execution of one instruction on more than one piece of data. In some embodiments, the computing device 200 may comprise a parallel processor with one or more cores. In one of these embodiments, the computing device 200 is a shared memory parallel device, with multiple processors and/or multiple processor cores, accessing all available memory as a single global address space. In another of these embodiments, the computing device 200 is a distributed memory parallel device with multiple processors each accessing local memory only. In still another of these embodiments, the computing device 200 has both some memory which is shared and some memory which can only be accessed by particular processors or subsets of processors. In still even another of these embodiments, the computing device 200, such as a multicore microprocessor, combines two or more independent processors into a single package, often a single integrated circuit (IC). In yet another of these embodiments, the computing device 200 includes a chip having a CELL BROADBAND ENGINE architecture and including a Power processor element and a plurality of synergistic processing elements, the Power processor element and the plurality of synergistic processing elements linked together by an internal high speed bus, which may be referred to as an element interconnect bus.

In some embodiments, the processors provide functionality for execution of a single instruction simultaneously on multiple pieces of data (SIMD). In other embodiments, the processors provide functionality for execution of multiple instructions simultaneously on multiple pieces of data (MIMD). In still other embodiments, the processor may use any combination of SIMD and MIMD cores in a single device.

Figure 2E:
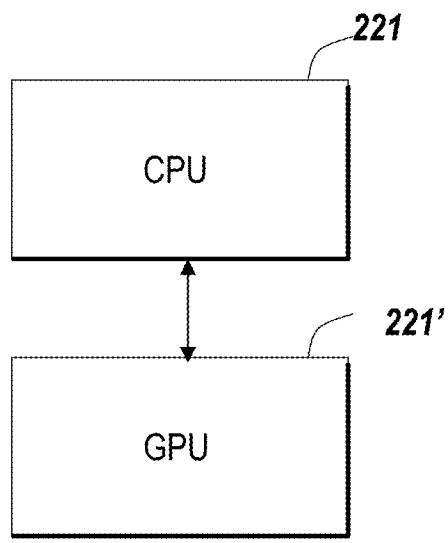

In some embodiments, the computing device 200 may comprise a graphics processing unit. In one of these embodiments, depicted in FIG. 2E, the computing device 200 includes at least one central processing unit 221 and at least one graphics processing unit. In another of these embodiments, the computing device 200 includes at least one parallel processing unit and at least one graphics processing unit. In still another of these embodiments, the computing device 200 includes a plurality of processing units of any type, one of the plurality of processing units comprising a graphics processing unit.

In one embodiment, a resource may be a program, an application, a document, a file, a plurality of applications, a plurality of files, an executable program file, a desktop environment, a computing environment, or other resource made available to a user of the local computing device 202. The resource may be delivered to the local computing device 202 via a plurality of access methods including, but not limited to, conventional installation directly on the local computing device 202, delivery to the local computing device 202 via a method for application streaming, delivery to the local computing device 202 of output data generated by an execution of the resource on a third computing device 206b and communicated to the local computing device 202 via a presentation layer protocol, delivery to the local computing device 202 of output data generated by an execution of the resource via a virtual machine executing on a remote computing device 206, or execution from a removable storage device connected to the local computing device 202, such as a USB device, or via a virtual machine executing on the local computing device 202 and generating output data. In some embodiments, the local computing device 202 transmits output data generated by the execution of the resource to another client computing device 202b.

In some embodiments, a user of a local computing device 202 connects to a remote computing device 206 and views a display on the local computing device 202 of a local version of a remote desktop environment, comprising a plurality of data objects, generated on the remote computing device 206. In one of these embodiments, at least one resource is provided to the user by the remote computing device 206 (or by a second remote computing device 206b) and displayed in the remote desktop environment. However, there may be resources that the user executes on the local computing device 202, either by choice, or due to a policy or technological requirement. In another of these embodiments, the user of the local computing device 202 would prefer an integrated desktop environment providing access to all of the resources available to the user, instead of separate desktop environments for resources provided by separate machines. For example, a user may find navigating between multiple graphical displays confusing and difficult to use productively. Or, a user may wish to use the data generated by one application provided by one machine in conjunction with another resource provided by a different machine. In still another of these embodiments, requests for execution of a resource, windowing moves, application minimize/maximize, resizing windows, and termination of executing resources may be controlled by interacting with a remote desktop environment that integrates the display of the remote resources and of the local resources. In yet another of these embodiments, an application or other resource accessible via an integrated desktop environment— including those resources executed on the local computing device 202 and those executed on the remote computing device 206—is shown in a single desktop environment.

In one embodiment, data objects from a remote computing device 206 are integrated into a desktop environment generated by the local computing device 202. In another embodiment, the remote computing device 206 maintains the integrated desktop. In still another embodiment, the local computing device 202 maintains the integrated desktop.

In some embodiments, a single remote desktop environment 204 is displayed. In one of these embodiments, the remote desktop environment 204 is displayed as a full-screen desktop. In other embodiments, a plurality of remote desktop environments 204 is displayed. In one of these embodiments, one or more of the remote desktop environments are displayed in non-full-screen mode on one or more display devices 224. In another of these embodiments, the remote desktop environments are displayed in full-screen mode on individual display devices. In still another of these embodiments, one or more of the remote desktop environments are displayed in full-screen mode on one or more display devices 224.

Figure 3A:
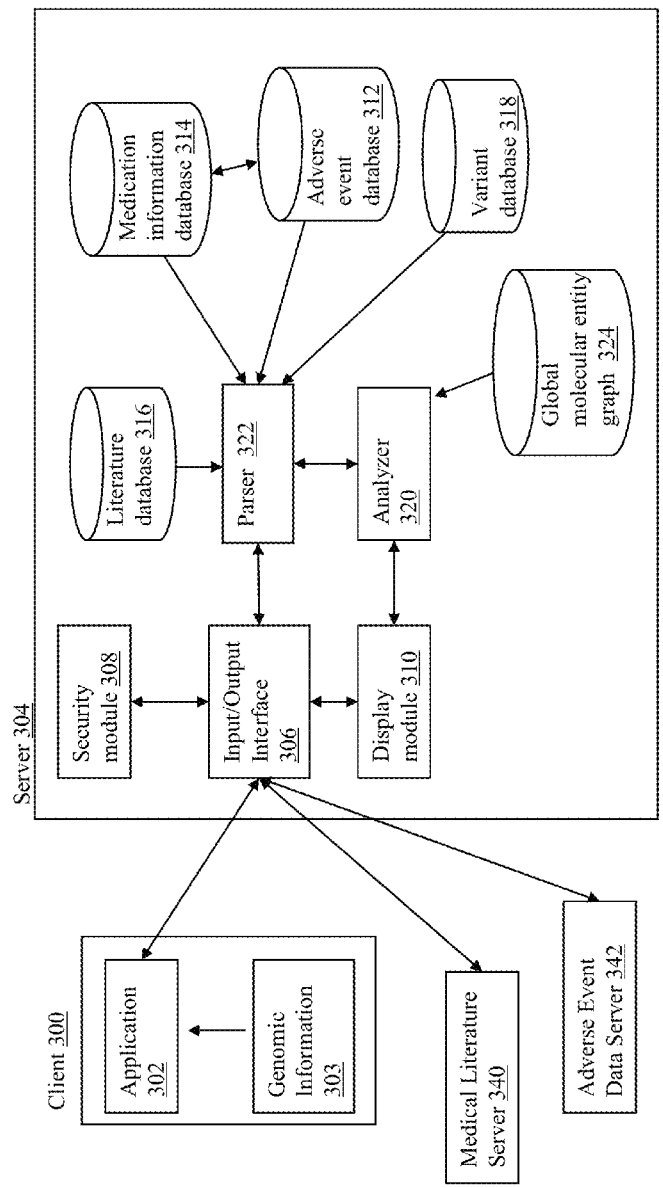
FIG. 3A is a block diagram of an embodiment of a system for multivariate analysis of adverse event data.

Referring now to FIG. 3A, illustrated is a block diagram of a system for multivariate analysis of adverse event data. In brief overview, a client 300 may comprise an application 302 and, in some embodiments, genomic information 303. In some embodiments, a client 300 may communicate with a server 304 via any type of network, such as those discussed herein. Although shown as a separate client-server system, in many embodiments, a client 300 and server 304 may be on the same physical machine. In other embodiments, server 304 may be executed by a virtual machine provided by a cloud computing environment. For example, server 304 may comprise a hosted service or cloud service, providing scalability and ease of management. In some embodiments, a medical literature server 340 and/or an adverse event data server 342 may also communicate with a server 304. In other embodiments not shown, a second client 300 may be used to gather data from a medical literature server 340 and/or an adverse event data server 342 and processed or transferred to server 304. In some embodiments, a server 304 may comprise an input/output interface 306, a security module 308, and/or a display module 310. Server 304 may also comprise one or more databases or data stores, including an adverse event database 312, a medication information database 314, a literature database 316, and a variant database 318. Server 304 may, in some embodiments, comprise an analyzer 320 and/or a parser 322. In some embodiments, server 304 may comprise a global molecular entity graph 324.

Still referring to FIG. 3A and in more detail, in some embodiments, a client 300 may comprise a computing device of any type, such as a desktop computer, portable computer, smart phone, tablet computer, or any other type of computing device. Client 300 may execute an application 302 for accessing server 304. In some embodiments, application 302 may comprise a web browser, while in other embodiments, application 302 may comprise a dedicated application for communicating with server 304.

In some embodiments, client 300 may store, include, or otherwise access genomic information 303. Genomic information 303 may comprise genetic data about a patient. For example, in some embodiments, genomic information 303 may comprise a list of genetic variants or mutations of the patient, a full or partial genetic sequence, or any similar information. In some embodiments, genomic information 303 may be utilized for generating personalized drug efficacy or risk information or identifying potential drug interactions. Although shown on client 300, in many embodiments, genomic information 303 may be stored externally to client 300, obtained from a third party or stored on a second server or network storage device, or otherwise be supplied to server 304.

Server 304 may comprise a computing device of any type, such as a desktop computer, portable computer, rackmount server, workstation, or any other type of computing device. In some embodiments, server 304 may comprise a virtual machine executed by a cloud service, a plurality of servers forming a grid or server farm 38 and acting as a single server 304, or any other type of server. Although shown with components 306-324 as part of server 304, in many embodiments, one or more of components 306-324 may be external to server 304, on a second server (not illustrated), on an external storage device, or otherwise accessible to server 304.

In some embodiments, server 304 may execute an input/output interface 306. Input/output interface 306 may comprise an application, service, daemon, routine, or other executable logic for communicating with one or more clients 300 or other servers, medical literature servers 340, and/or adverse event data servers 342. In some embodiments, input/output interface 306 may comprise a web server or web page executed by a web server. Input/output interface 306 may provide an interface allowing a user to provide queries, make selections or identifications of drugs, indications, targets, pathways, or other molecular entities, define cohorts for analysis, or perform other functions. In some embodiments, input/output interface 306 may provide data tables, graphics, or other output views to the user. In many embodiments, input/output interface 306 may communicate via a network with application 302, while in other embodiments in which client 300 and server 304 comprise the same computing device, application 302 may be executed on server 304 and may communicate with input/output interface 306 via an API.

In some embodiments, server 304 may execute a security module 308. Security module 308 may comprise an application, service, daemon, routine, or other executable logic for receiving user credentials or login information and/or computing device credentials, such as a network address, operating system version or other identification, and processing the credentials to allow or deny access to server 304. Security module 308 may, in some embodiments, comprise a user and password database or similar features to control access to functions of server 304.

In some embodiments, server 304 may execute a display module 310. Display module 310 may comprise an application, service, daemon, routine, or other executable logic for generating graphic displays for presentation by input/output interface 306 and/or application 302 to a user. In some embodiments, display module 310 may generate graphs, tables, radial graphs, charts, biological network diagrams, or other graphical entities. In some embodiments, input/output interface 306 and display module 310 may be provided as part of a web server or application, while in other embodiments, these services may comprise separate executable modules.

Server 304 may include an adverse event database 312 and/or a medication information database 314. In some embodiments, adverse event database 312 and/or medication information database 314 may be stored on server 304, while in other embodiments, adverse event database 312 and/or medication information database 314 may be stored on a data storage server, external storage device, within a cloud storage system, or otherwise accessible to parser 322 and/or analyzer 320. An adverse event database 312 may comprise a database, flat file, data array, or other data file for storing molecular data regarding adverse events. Similarly, a medication information database 314 may comprise a database, flat file, data array, or other data file for storing molecular entity information for one or more drugs. As discussed above in connection with FIG. 1B, stored data may comprise identifications of one or more drugs 102, indications 104, reactions 106, outcomes 108, pathways 110, targets 112, metabolizing enzymes or transporters 114, and drug classes 116. In many embodiments, adverse event data may comprise demographic information of a patient, trial participant, or other person that experienced the adverse event. In many embodiments, adverse event data 102-108 from adverse event reporting systems may be combined and linked with molecular entity data 110-116 in the adverse event database 312 and/or medication information database 314. In some embodiments, molecular entity data 110-116 for a drug may be retrieved from pharmaceutical manufacturer literature, research literature or white papers, or other literature from one or more medical literature servers 340. In many embodiments, adverse event database 312 and medication information database 314 may comprise a single database, while in other embodiments, databases 312-314 may be linked to allow associations between entities and adverse event data. In some embodiments, associations may be one-to-one, such as a single outcome for a single patient, while in other embodiments, associations may be one-to-many, such as a plurality of prescribed and co-prescribed drugs for the patient, or many-to-many, such as a plurality of indications associated with each of a plurality of drugs. Accordingly, a adverse event/molecular entity database comprising adverse event database 312 and medication information database 314 may comprise a multi-dimensional database allowing associations between adverse events and biological information. Such a database may be used for novel univariate analyses, such as generating an ordered list of metabolizing enzymes most frequently associated with a specified side effect (by numbers of adverse event reports for the side effect or reaction including a drug, the drug associated with the metabolizing enzyme in medical literature). Similarly, such a database may be used for multivariate analyses, such as comparing reported side effects of all drugs targeting a first protein with side effects of all drugs targeting a second protein.

In some embodiments, medication information database 314 may comprise or be associated with a literature database 316. Literature database 316 may comprise a database, data array, flat file, or other data comprising one or more items of literature about one or molecular entities. Literature database 316 may comprise white papers, research papers, theses, dissertations, abstracts of literature, publicly available literature, proprietary manufacturer literature, research data, or other literature. In some embodiments, literature database 316 may comprise medication information, which may be extracted to generate a medication information database 314. In some embodiments, a server 304 may retrieve or receive literature from one or more medical literature servers 340. For example, in one embodiment, server 304 may retrieve abstracts or full papers from the PubMed database provided by the National Institutes of Health of Bethesda, Md. Such papers or abstracts may be parsed to identify drug names, drug classes, protein targets, metabolizing enzymes, transporters, gene variants or wild types, or other molecular entities. Once identified, the entities and associations between identified entities may be added to literature database 316, medication information database 314, adverse event database 312, or a combined multi-dimensional molecular data database.

In some embodiments, adverse event database 312 may further comprise identification of patient genetic variants or mutations, or may be associated with a variant database 318.

A variant database may comprise a database, data file, flat file, data array, or other file comprising a full genetic sequence for one or more patients, clinical trial participants, or other persons, or may comprise a partial sequence, or may comprise an identification of one or more variants or mutated gene sequences for a patient, participant, or person. In some embodiments, a variant database may further comprise identifications of one or more proteins corresponding to a variant, in which expression or activation of the protein is affected by the mutation. For example, in one such embodiment, a database may comprise an identification of a variant and an identification of a protein activated by the wild type corresponding to the variant. By linking variant identifications, protein activation or deactivation, and drug target proteins, a user may identify potential decreased efficacy of a drug or high risk biological interactions.

In some embodiments, a server 304 may comprise an analyzer or analysis module 320. Analyzer 320 may comprise an application, service, daemon, routine, or other executable logic for performing univariate or multivariate analysis. In some embodiments, analyzer 320 may identify associated entities from a database, such as reactions associated with a target protein, or outcomes associated with a genetic variant. In many embodiments, analyzer 320 may generate one or more lists of associated entities based on an input or requested first entity. Such lists may be ordered, for example, by a percentage of total associations or by number of associations in the database. Accordingly, for a query of adverse reactions associated with a first drug, analyzer 320 may return an ordered list indicating that, for example, of all reported adverse reactions associated with the first drug, nausea occurs in 60% of cases, fatigue occurs in 50% of cases, and a rash occurs in 40% of cases. Due to the possibility of patients experiencing multiple adverse events, totals may exceed 100%. Similarly, for a query of targets associated with an adverse reaction such as fatigue, analyzer 320 may return a list of molecular targets ordered by proportional reporting ratio (PRR), such as dihydroorotase having a PRR of 32.91, DNA polymerase i having a PRR of 16.45, and cytochrome b having a PRR of 8.22. Such proportional reporting rations may be determined based on a proportion of reactions to the molecular entity compared to the same proportion for all such entities in the database. In some embodiments, analyzer 320 may further comprise functionality for performing multivariate analyses and comparisons. For example, analyzer 320 may comprise logic for extracting subsets of statistical data of adverse events associated experienced by an identified first cohort of patients or trial participants and an identified second cohort, and comparing the two subsets to identify adverse event differences between the cohorts. Phenotype or genotype distinctions between the cohorts may then be identified as the likely cause or mitigation of adverse events.

In some embodiments, server 304 may comprise a parser 322. Parser 322 may comprise an application, service, daemon, routine, or other executable logic for reading and interpreting medical literature obtained from a medical literature server 340 or stored in a literature database 316. Reading and interpreting medical literature may comprise scanning literature for identifications of one or more molecular entities. Inclusion of identifications of a plurality of entities within a single item of literature may indicate an association between those entities. Such associations may then be incorporated into a medication information database 314 and/or adverse event database 312. For example, parser 322 may scan medical literature and identify that the terms "headache" and "aspirin" frequently appear in the same items of literature. Accordingly, parser 322 may identify the indication "headache" as related to the drug "aspirin" in a medication information database 314. Similarly, in some embodiments, parser 322 may identify associations within literature between drugs, targets, transporters, metabolizing enzymes, drug classes, genetic variants, side effects, indications, reactions, outcomes, patient demographic information, or any other such information. Parser 322 may scan white papers, abstracts, articles, theses, research documents, manufacturer literature, or any other type of document for associations between molecular entities. In some embodiments, parser 322 may score the identified associations responsive to one or more factors, such as frequency, proximity, and secondary citations. For example, parser 322 may give a low association score to two molecular entities that appear in only a single item of literature once. However, parser 322 may give a higher association score to the two molecular entities, if they appear in close proximity to each other within the literature, such as in the same sentence or paragraph. In some embodiments, parser 322 may give a higher association score to associations between two entities that appear in a plurality of items of literature than an association between two entities that appears repeatedly in only a single item of literature. In such embodiments, parser 322 may thus identify associations that are commonly understood by researchers, rather than unconfirmed or proposed associations. In some embodiments, parser 322 may further identify secondary items of literature that cite a first item of literature, and give a higher score to associations identified within the first item of literature. Frequently cited literature thus may become more authoritative regarding associations.

Figure 3B:
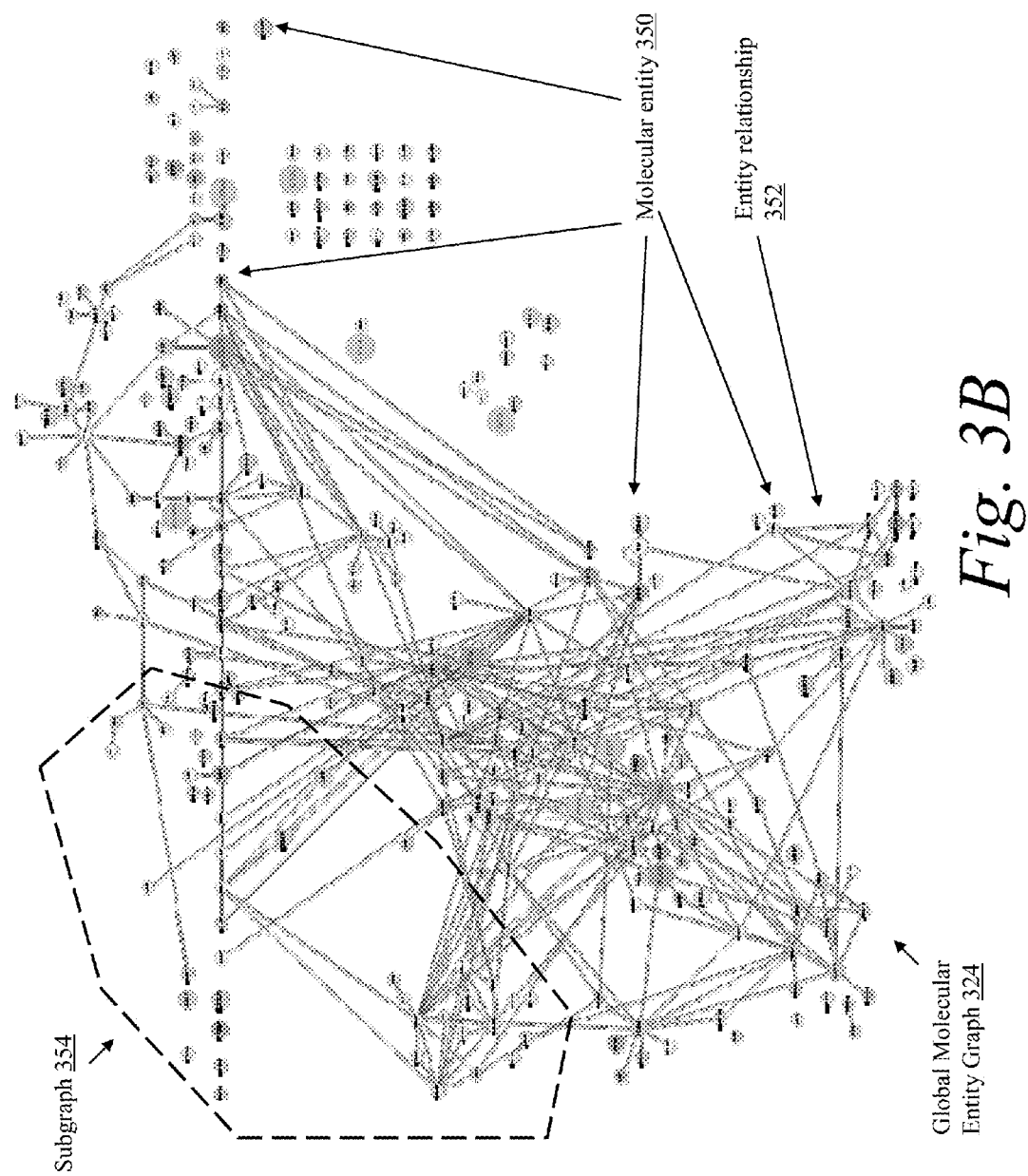
FIG. 3B is a diagram of an example embodiment of a global molecular entity graph.
Figure 3C:
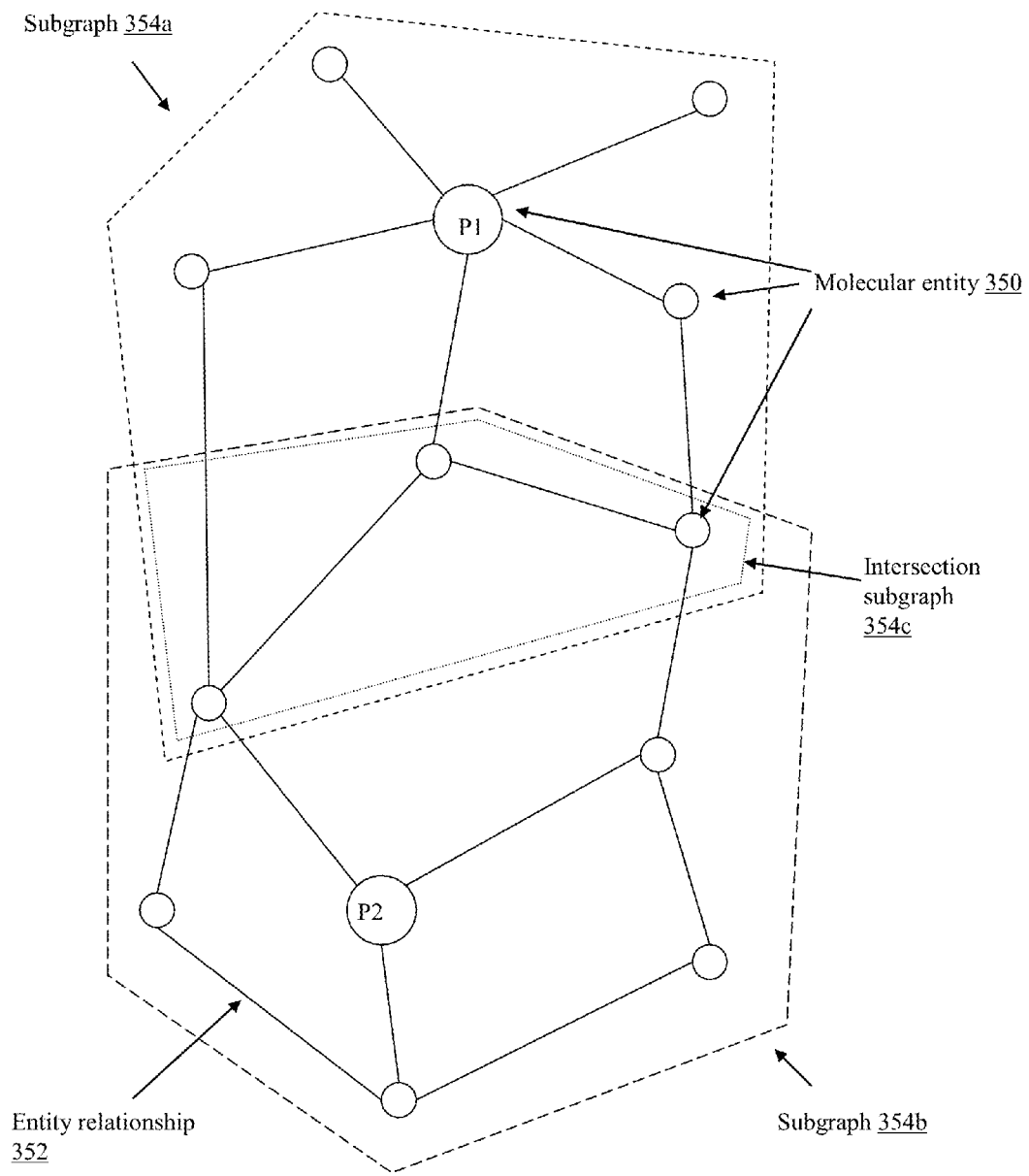
FIG. 3C is a diagram of an example embodiment of extracted subgraphs.

In some embodiments, server 304 may comprise a global molecular entity graph 324. Global molecular entity graph 324 may comprise a graph, database, or other data file for identifying a plurality of molecular entities and relationships between entities. Global molecular entity graph 324 may comprise a system-wide representation of some or all biological systems within the human body. For example, referring briefly to FIG. 3B, illustrated is a diagram of an example embodiment of a global molecular entity graph 324. The graph may comprise a plurality of molecular entities 350, such as proteins, enzymes, transporters, or other entities, and each entity 350 may be associated with one or more other entities 350 via a relationship 352. In some embodiments, a global molecular entity graph 324 may be used by an analyzer 320 to extract subgraphs 354, which may comprise portions of the molecular entity graph important to a particular entity. For example, a subgraph 354 may comprise all entities and relationships between entities associated with a first identified entity, such as a drug target. In some embodiments, multiple subgraphs 354 may be extracted and compared to identify common entities and/or relationships between the subgraphs. For example, referring briefly to FIG. 3C, illustrated is a diagram of an example embodiment of two extracted subgraphs, 354a and 354b, intersected to identify an intersection subgraph 354c. A first subgraph 354a may be extracted for a first drug target (P1), and a second subgraph 354b extracted for a second drug target (P2). The intersection subgraph 354c may identify one or more molecular entities 350 affected by each of P1 and P2. These dual-affected entities may be causes of adverse effects experienced when drugs targeting P1 and P2 are taken simultaneously, but not experienced when drugs targeting P1 and P2 are taken separately. By using multivariate analysis of adverse event data and extracting subgraphs for identified entities with disparate adverse event data, server 304 may be able to identify one or more molecular entities associated with a particular side effect, even when the association would be normally hidden in univariate analyses.

Returning to FIG. 3A, in some embodiments, server 304 may communicate with a medical literature server 340 and/or an adverse event data server 342. Medical literature server 340 may comprise any server, database, online storage system, cloud storage device, offline storage system, computing device, or other device for storing medical literature, including research documents, theses, white papers, manufacturer data, or other literature. In some embodiments, server 304 may access medical literature server 340 to retrieve documents to fill literature database 316, medication information database 314, variant database 318, or for parsing one or more items of literature via parser 322 as discussed above. Similarly, adverse event data server 342 may comprise any server, database, online storage system, cloud storage device, offline storage system, computing device, or other device for storing adverse event data, such as the Adverse Event Reporting System provided by the U.S. Food & Drug Administration. In some embodiments, server 304 may access an adverse event data server 342 to retrieve records to fill an adverse event database 312 or for parsing by parser 322 or analysis by analyzer 320, as discussed above.

In some embodiments, a safety profile, sometimes referred to as an adverse event profile or side effect profile, may comprise a list of all adverse event reports associated with a molecular entity, such as all adverse event reports for a prescribed or co-prescribed medication. In other embodiments, a safety profile may comprise a statistical table of adverse event reports associated with a molecular entity, such as a table identifying frequency of occurrence of one or more adverse events with patients or trial participants consuming a specified drug. A molecular entity multivariate analysis system may be used to compare the safety profiles of a plurality of molecular entities, allowing identification of entities responsible for adverse event differences between safety profiles. For example, in some embodiments, a safety profile for a first drug or medication may be compared to a safety profile for a second drug or medication. Similarly, safety profiles may be generated based on molecular entities associated with adverse event reports. For example, a patient that experienced an adverse event may have been prescribed a first drug. The first drug may be known to target a first protein. Accordingly, by correlating this information with the adverse event report, a safety profile for the protein may be generated. Thus, in some embodiments, a safety profile for a protein target may be compared to a safety profile for a second protein target.

Figure 4A:
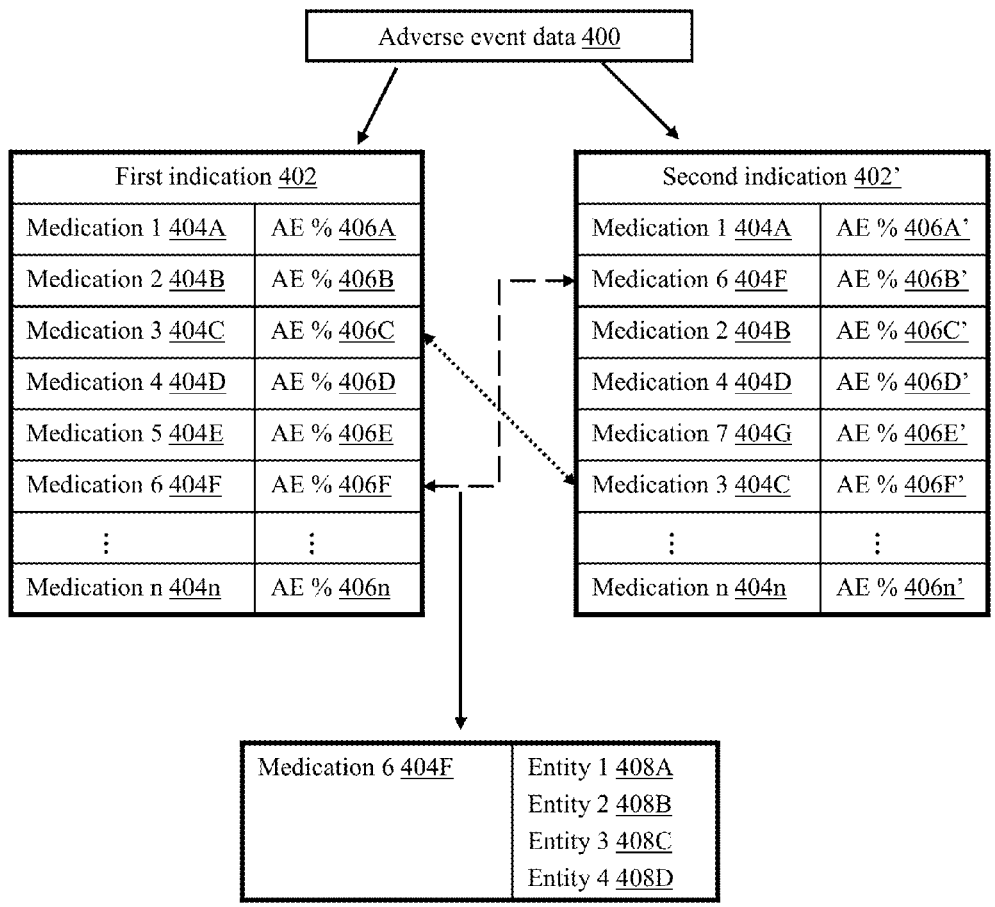
FIG. 4A is a diagram of an embodiment of method for identifying molecular entities responsible for adverse event differences between similar indications.

Similarly, safety profiles may be generated and compared for indications themselves. Such safety profiles may comprise a list of medications prescribed or co-prescribed to patients identified as being treated for the indication. In one embodiment, such a list may be ordered by percentage of patients prescribed or co-prescribed the medication, while in another embodiment, such a list may be ordered by percentage of patients prescribed or co-prescribed the medication who experienced an adverse event, or a particular outcome or outcomes. Accordingly, in some embodiments, a multivariate analysis system may be able to determine if two similar indications, such as depression and post-partum depression, have a different prioritization of drugs responsible for adverse events. Although discussed primarily in terms of similar indications, in many embodiments, any two or more indications may compared, allowing complex analysis of similarities between apparently diverse indications. For example, and referring briefly to FIG. 4A, illustrated is a block diagram of an embodiment of a method for identifying molecular entities responsible for adverse event differences between indications. A multivariate analysis system may retrieve a safety profile for a first indication 402 from adverse event data 400, and may generate a list of medications 404A-404$n$ ordered by percentage of medication-consumers experiencing an adverse event 406A-406$n$. In some embodiments, the list may be ordered by percentage of medication-consumers experiencing any adverse event, while in other embodiments, the list may be narrowed to include only percentages of medication-consumers experiencing a specific adverse event. Similarly, the multivariate analysis system may retrieve a second safety profile for a second indication 402', and may generate a list of medications 404A-404$n$ ordered by percentage of medication-consumers experiencing an adverse event 406A'-406$n$'. In some embodiments, safety profiles may include different medications 404A-404N, although in most embodiments, a medication 404A-404$n$ may appear in both safety profiles. Additionally, medications may appear in different priorities in each ordered list, such as medication 404C and medication 404F in the example lists of FIG. 4A. Differences in order may be due to physiological specificities of either indication and their differential effect on drug pharmacokinetics or dynamics. Accordingly, through analysis of the different molecular entities (e.g. entities 408A-408D) associated with a medication appearing in a first position in one safety profile for a first indication and in a second, different position in another safety profile for a second indication (e.g. medication 6 404F), molecular entities affected differently by each indication may be immediately identified. In many embodiments, such second indication may comprise an indication similar to the first. This may provide opportunities for more targeted therapies for one or both indications. Furthermore, when safety profiles for each of the indication are narrowed by a specific adverse event, differences between each safety profile may identify potentially unknown interactions between molecular entities associated with the indication and molecular entities associated with the adverse event. For example, if a large percentage of patients with a first indication taking a first medication experience a specific adverse event, but a small percentage of patents with a second indication taking the first medication experience the specific adverse event, this may indicate differences between each indications interaction with the molecular entities responsible for the adverse event. Although shown ordered by percentage in FIG. 4A, in many embodiments, each list may be in any order, with comparisons performed on percentage values associated with each medication as opposed to order.

Figure 4B:
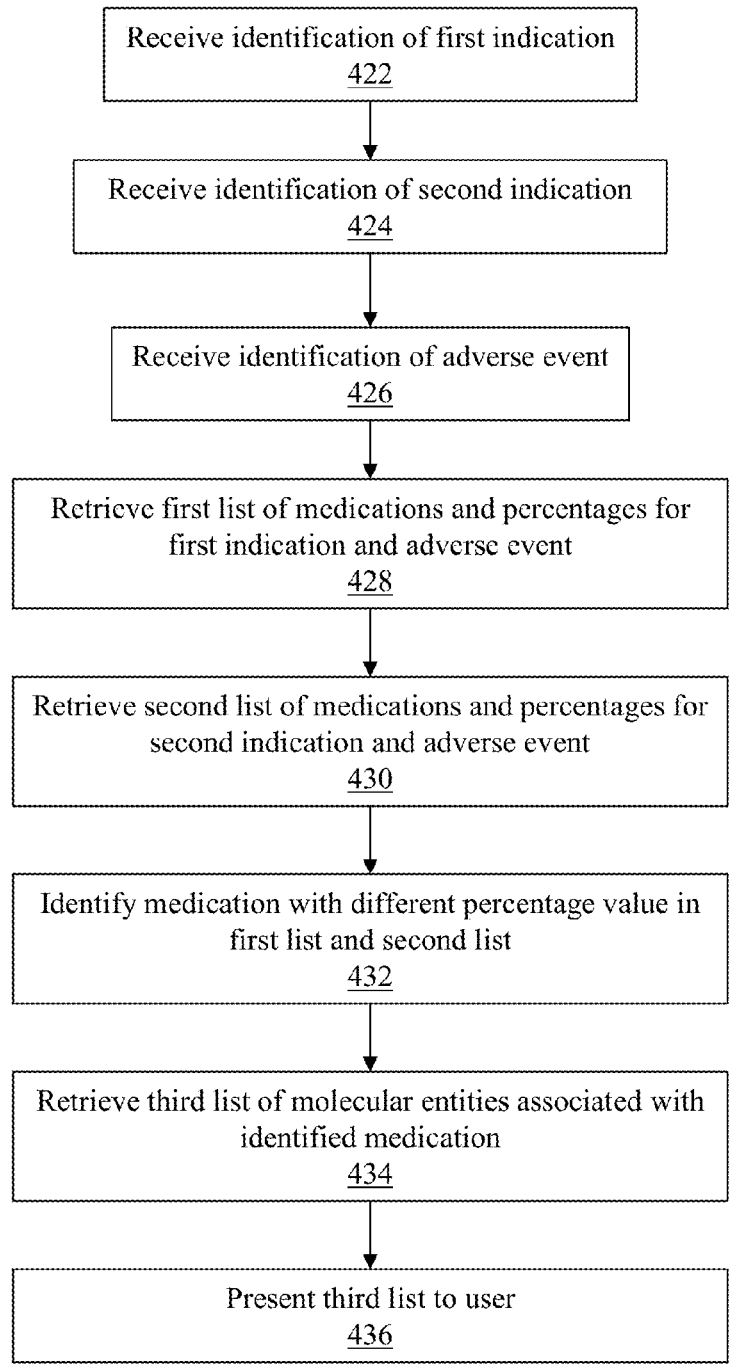
FIG. 4B is a flow chart of an embodiment of method for identifying molecular entities responsible for adverse event differences between similar indications.

Referring now to FIG. 4B, illustrated is a flow chart of an embodiment of a method for identifying molecular entities responsible for adverse event differences between indications. In brief overview, a multivariate analyzer such as analyzer 320 of a computing device 304 may receive an identification of a first indication at step 422. The analyzer may receive an identification of a second indication at step 424. In many embodiments, the second indication may be similar to the first indication. At step 426, in some embodiments as discussed above, the analyzer may receive an identification of an adverse event. At step 428, the analyzer may retrieve from an adverse event database a first list of medications prescribed to patients for the first indication, the list comprising percentages of patients prescribed each medication who experienced an adverse event. In some embodiments, the list may be limited to adverse event data for the identified adverse event, and accordingly, the list may comprise percentages of patients prescribed the medication who experienced the identified adverse event. At step 430, the analyzer may retrieve from the adverse event database a second list of medications prescribed to patients for the second indication, the list comprising percentages of patients prescribed each medication who experienced an adverse event. In some embodiments, the list may be limited to adverse event data for the identified adverse event, and accordingly, the list may comprise percentages of patients prescribed the medication who experienced the identified adverse event. At step 432, in some embodiments, the analyzer may compare the first list and second list to identify one or more medications with a different percentage value in each list. At step 434, the analyzer may retrieve one or more lists of molecular entities associated with a corresponding each of the identified one or more medications. At step 436, an output module of the computing device may present the retrieved one or more lists of molecular entities to the user as lists of molecular entities potentially affected by only one of the first indication and the second indication.

Still referring to FIG. 4B and in more detail, at step 422, an analyzer 320 may receive an identification of a first indication. As discussed above, an indication may comprise a disease, a symptom, an adverse effect, or any other such circumstance which indicates the advisability or necessity of a specific medical treatment or procedure. In some embodiments, analyzer 320 may receive the identification of a first indication from an input/output module, such as a web interface or application interface. In some embodiments, a user may select the first indication or input a name of the first indication into a text entry field, and an input module may pass the identification of the indication to the analyzer. In other embodiments, the user may select the first indication from a list of indications. In many embodiments, analyzer 320 may receive the identification of the indication from a second computing device operated by or on behalf of the user.

At step 424, the analyzer may receive an identification of a second indication. The second indication may be similar to the first indication, in some embodiments, while in other embodiments, the second indication may comprise any indication. Indications may be similar if they share symptoms; are subsets of a category of indication (e.g. different types of cancer); if they are commonly or functionally associated (e.g. nausea and vomiting); or via other similar associations. In some embodiments, indications may be similar if they are involve the same pathway, protein, or other molecular entity. In some embodiments, analyzer 320 may receive the identification of the second indication from an input/output module, such as a web interface or application interface. In some embodiments, a user may select the second indication or input a name of the second indication into a text entry field, and an input module may pass the identification of the indication to the analyzer. In other embodiments, the user may select the second indication from a list of indications. In many embodiments, the analyzer may receive the identification of the second indication from a second computing device operated by or on behalf of the user.

At step 426, in some embodiments, the analyzer may receive an identification of an adverse event. In some embodiments, the adverse event may comprise an adverse event distinct from the first indication and second indication. The adverse event may thus be suspected of being caused by one or more drugs prescribed or co-prescribed to patients with the first or second indication. For example, in one embodiment, the two similar indications may comprise depression and post-partum depression, and the adverse event may comprise a rash. As depression is not typically associated or functionally identified as causing a rash, clinicians may suspect that the adverse event is not caused by the indication, but by a medication. Thus, in many embodiments, the adverse event may not be an adverse event corresponding to one of the indications (e.g. an adverse event of fatigue for an indication of chronic fatigue syndrome).

Figure 4C:
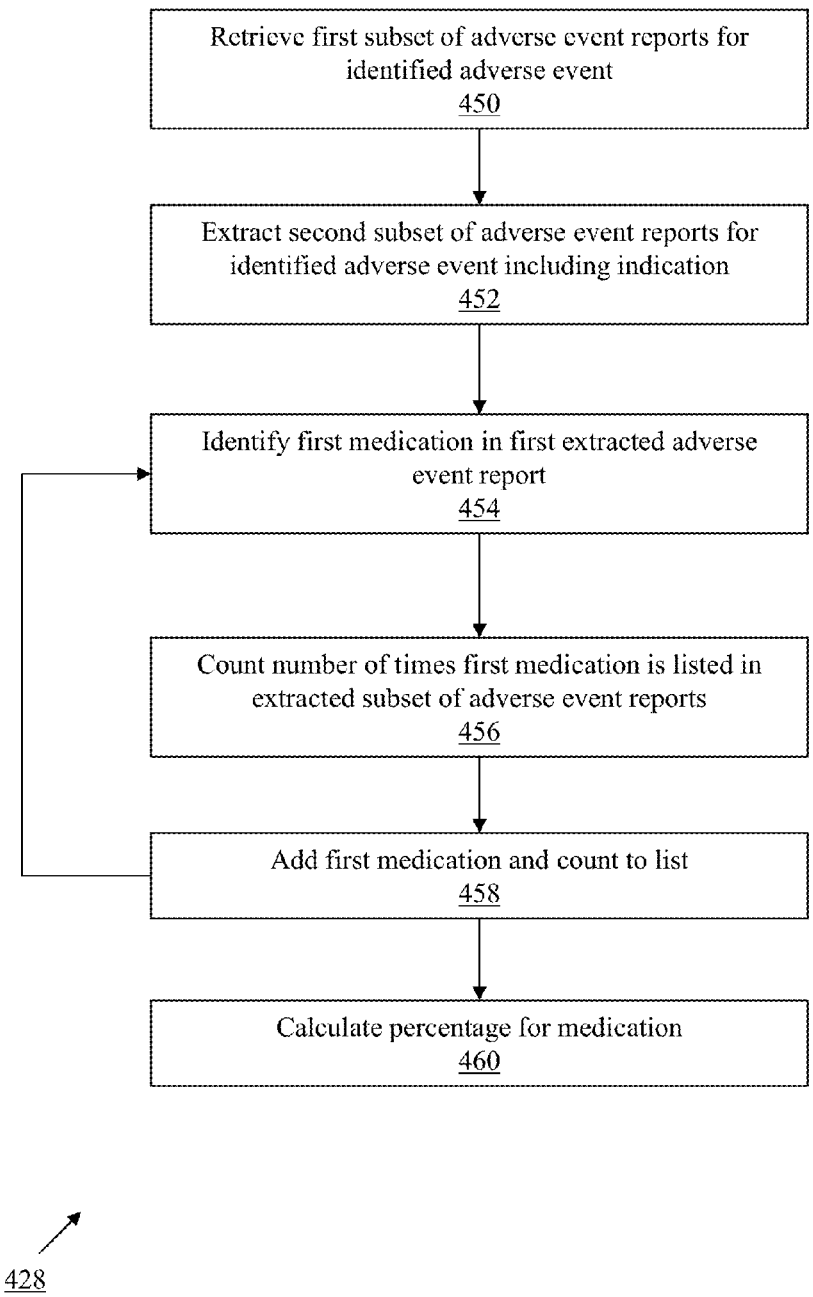
FIG. 4C is a flow chart of an embodiment of a method for retrieving an ordered list of medications for an indication and adverse event.

At step 428, the analyzer may retrieve a first list of medications prescribed to patients with the first indication who experienced the identified adverse event, and a second list of medications prescribed to patients with the second indication who experienced the identified adverse event. Retrieving the lists of medications may comprise searching an adverse event database for reports corresponding to the identified adverse event. Each report may comprise patient demographic information, an identification of the adverse event, an identification of an indication, an identification of an outcome, and an identification of one or more medications consumed by the patient. The adverse event database may comprise a collated index of adverse events, normalized to be searchable with standard terms and definitions (for example, replacing abbreviations with full titles, etc.). In some embodiments, the analyzer may retrieve a subset of adverse event reports that include the identification of the adverse event. The analyzer may then extract a second subset of adverse event reports that include the identification of the first indication, and extract a third subset of adverse event reports that include the identification of the second indication. The analyzer then, in some embodiments, may iteratively sort or count the extracted subsets of adverse event reports to generate a table of medications identified in the extracted subsets, sorted by count or percentage of listing in the extracted subsets. In other embodiments, the tables may be unsorted. For example, referring briefly to FIG. 4C, illustrated is a flow chart of an embodiment of a method 428 for retrieving a list of medications for an indication and adverse event. At step 450, as discussed above, the analyzer may retrieve the first subset of adverse event reports for the identified adverse event, and at step 452, the analyzer may extract a second subset of adverse event reports from the first subset including the indication. Although shown in this order, in many embodiments, these steps may be reversed. For example, the analyzer may extract a subset of adverse event reports for the indication, and may then extract a further subset of adverse event reports corresponding to the identified adverse event. Furthermore, in some embodiments, these steps may be performed simultaneously as part of a Boolean search.

At step 454 of FIG. 4C, the analyzer may identify a first medication in the extracted subset of adverse event reports for the indication and identified adverse event. At step 456, the analyzer may then search the extracted subset to identify the number and/or percentage of times that the first medication is listed in the adverse event reports. In some embodiments, the analyzer may search the extracted subsets for records in which the first medication is listed as the medication suspected of causing the identified adverse reaction as opposed to being a co-prescribed or concomitant medication, while in other embodiments, the analyzer may search the extracted subsets for all appearances of the first medication. At step 458, the analyzer may add the first medication and the count or percentage to a list. In some embodiments, a percentage of the reports in which the medication appears out of the total number of adverse event reports for the indication and adverse event may be more useful, while in other embodiments, a raw count may be preferred. The list may be similarly sorted by either number. In many embodiments, analyzer may iteratively repeat steps 454-458 for each additional medication identified in the extracted subset of adverse event reports. At step 460, in some embodiments utilizing raw counts, the analyzer may determine a percentage for each medication as discussed above. In some embodiments, the analyzer may sort the list by the identified count or percentage to generate an ordered list. Sorting may be done through any sort algorithm, such as a bubble sort, quick sort, merge sort, or any other type of sorting.

Returning to FIG. 4B, at step 430, the analyzer may retrieve a second list of medications for the second indication and the identified adverse event. Although shown for step 428 of FIG. 4B, embodiments of the method shown in FIG. 4C may also be applied to step 430 for retrieval of the second list of medications. In some embodiments, steps 428 and 430 may be performed in any order, or simultaneously, such as by a multi-threaded processor.

At step 432, the analyzer may compare the first list and second list to identify a medication with a different percentage value in each list. In some embodiments, if the medication appears in 90% of adverse event reports for the first indication, but only 20% of adverse event reports for the second indication, the difference in percentages may indicate an important distinction between the two indications. Accordingly, in many embodiments, the analyzer may identify a medication with a difference between the count or percentage in the first list and the count or percentage in the second list that is greater than a predetermined threshold amount. Such a threshold may be a percentage, such as 5%, 10%, 20% or any other value, or may be a number, such as 100 reports, 1000 reports, or any other value. As discussed above, in many embodiments, ordering by percentages may be useful for certain comparisons, such as where a first indication has a greater number of adverse event reports than a second indication. In such embodiments, percentages may be more easily compared than raw counts. In other embodiments, the analyzer may determine differences based on each medication's position in each list, the list being ordered by percentage or count. This may be useful in embodiments in which raw counts are used, for example. In similar embodiments, the list may comprise an index number for each entry, and the analyzer may compare index numbers of a medication in both lists.

At step 434, in some embodiments, the analyzer may retrieve a third list of molecular entities associated with the identified medication from a medication information database. As discussed above, in some embodiments, a medication information database may comprise part of or be joined with an adverse event database. The medication information database may identify a medication and known targets, pathways, enzymes, transporters, or other molecular entities associated with the medication.

At step 436, in some embodiments, the analyzer may present the retrieved third list to the user as a list of molecular entities potentially affected by only one of the first indication and the second indication. As discussed above, if a first indication causes activation of a particular protein and a second indication does not, and a medication's interaction with the activated protein causes the adverse effect, such adverse effect differences may be detected in the adverse event reports, indicating that the first indication and second indication interact with the molecular entities affected by the medication in different ways. This may be useful in identifying potential avenues for research for the two indications.

In some embodiments, the analyzer may repeat steps 432-434 for additional medications appearing in both the first list and second list. In one such embodiment, the analyzer may present a plurality of lists of molecular entities for each identified medication, while in other embodiments, the analyzer may merge the lists of molecular entities. In one embodiment, the analyzer may generate a combined list including all molecular entities in each retrieved list, while in other embodiments, the analyzer may generate an intersection list including only molecular entities in all retrieved lists. In still other embodiments, the analyzer may generate a combined list comprising a score for each molecular entity. In one embodiment, each score may comprise a default score. The analyzer may increase the default score for each molecular entity appearing in a plurality of lists and/or decrease the default score for each molecular entity appearing in one list. In some embodiments, each molecular entity may be scored responsive to the number of retrieved lists in which it appears. This may be used to generate a priority of which molecular entities are most likely associated with the adverse event rate differences. With a greater number of medications inducing or suppressing an adverse effect at a different rate in each indication, the analyzer may be able to generate more accurate priorities of molecular entities associated with the adverse event rate differences.

As discussed above, in some embodiments, a computing device may comprise global molecular entity graph. Such a graph may comprise a linked network of nodes representing molecular entities, such as proteins or enzymes, and functional interactions between the entities, such as a link between an enzyme and an organic compound catalyzed by the enzyme. In some embodiments, the graph may comprise a hypergraph with edges connecting to more than two nodes, while in other embodiments, the graph may comprise a two-dimensional graph with intermediate reaction nodes.

A global molecular entity graph may be used for identifying molecular entities associated with a side effect or indication and building an indication or side effect-specific model of molecular interactions. Although the global molecular entity graph is not indication or side effect specific, an analyzer may extract subgraphs or subnetworks from the global molecular entity graph to generate a model of entities related to a specified indication. Building an indication or side effect specific molecular entity model may allow for targeted pharmacological research regarding entities previously unassociated with the indication or side effect. In some embodiments, the analyzer may utilize an adverse event database to identify medications associated with the specified indication and/or adverse event. The analyzer may then use a medication information database to identify molecular entities, such as a proteins and enzymes, related to the identified medications. In other embodiments, as discussed above, medication information may be integrated into the adverse event database such that each adverse event record further includes or is linked to identifications of molecular entities associated with the prescribed or consumed medications of the patient that experienced the adverse event. Accordingly, in such embodiments, the analyzer may utilize the database to identify molecular entities associated with the specified indication and/or adverse event. In some embodiments, the analyzer may identify molecular entities or medications that are most highly associated with the selected indication or side effect. For example, as discussed above, in some embodiments, the analyzer may sort a retrieved list of medications or molecular entities associated with adverse event reports for the selected indication or side effect. In a further embodiment, the analyzer may discard medications or molecular entities with a count or percentage below a predetermined threshold. For example, in building a side effect-specific model, it may be advantageous to focus on molecular entities associated with the side effect in more than 50% of the adverse event reports for the side effect, and discard entities in fewer than 50% of the reports. The predetermined threshold may be any value, and, in some embodiments, may even include 0% or 100%, either allowing in all associated entities, or restricting to entities that appear in every adverse event record. Medications or entities may be sorted and ordered by various statistical techniques, including proportional reporting ratios (PRR), regularized PRR (normalized such that older medications do not outweigh newer medications in the adverse event reports merely due to amount of data collected, for example), logistic regression, or other algorithms.

Figure 5A:
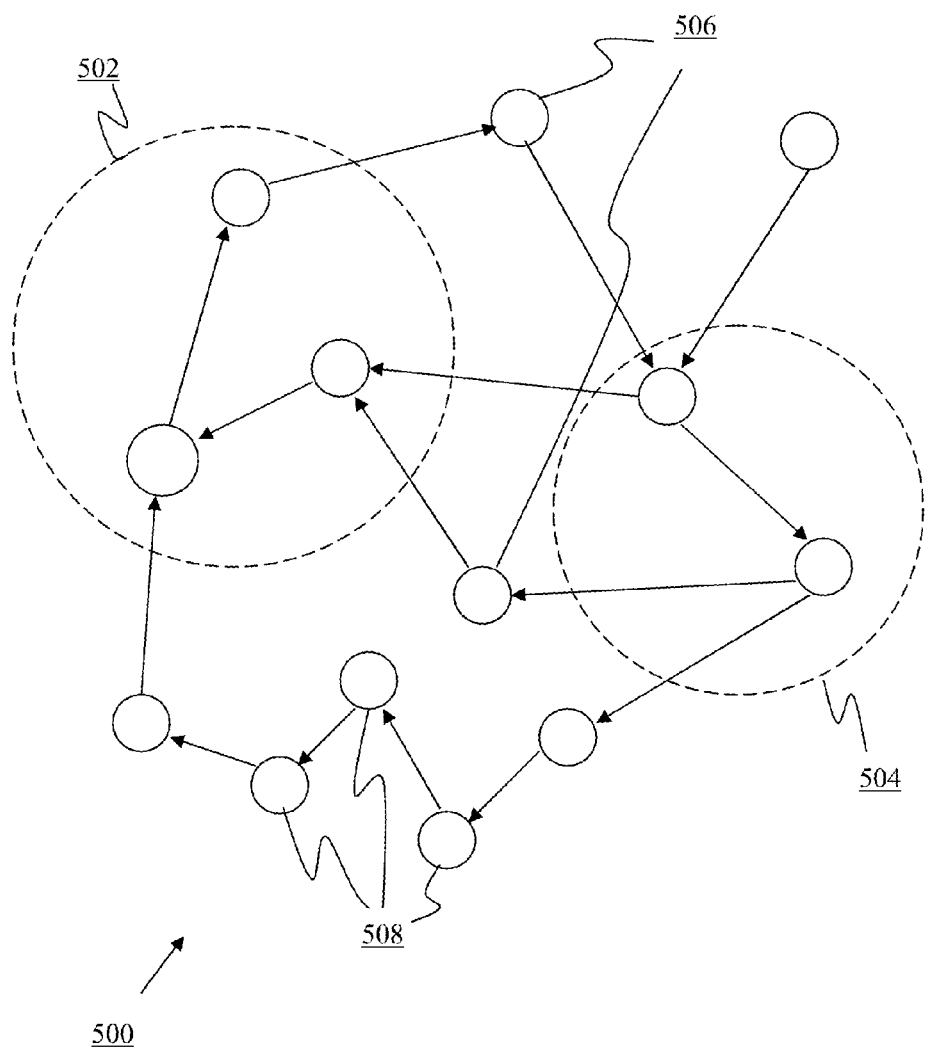
FIG. 5A is a diagram of another embodiment of a global molecular entity graph.

In many embodiments, the molecular entities identified at this stage may include only entities known to be associated with the identified medications. For example, the entities may include known target proteins, but may not include unknown off-target proteins or intermediate molecular entities involved in catalyzing or metabolizing the medication. Furthermore, as multiple medications may be associated with an indication or side effect, the identified entities may comprise disjoint regions of the global molecular entity graph. For example, referring briefly to FIG. 5A, illustrated is a chart diagram of an embodiment of a global molecular entity graph 500. Multiple molecular entities or nodes may be linked to show functional interaction. A first subset of entities 502 may be known to be associated with a first medication, and a second subset of entities 504 may be known to be associated with a second medication, the first medication and second medication associated with a selected indication or side effect. Including only the subsets 502 and 504 may comprise an incomplete list of the entities responsible for or associated with experiencing the selected indication or side effect.

Accordingly, the global molecular entity graph may be used to expand or augment the identified set of entities by identifying additional entities functionally related to known and identified entities, such as subsets 502 and 504. In one embodiment, the set of entities may be augmented by performing a shortest path analysis between disjoint pairs of known entities, such as a first entity identified as associated with a first medication (e.g. subset 502) and a second entity identified as associated with a second medication (e.g. subset 504). In some embodiments, edges between nodes may be weighted based on relationships to other entities. For example, edges to an intermediate node between two entities may be more heavily weighted if the intermediate node is further connected to a second intermediate node between both entities. In other embodiments, edges between nodes may be weighted responsive to identification of the node as related to an organ associated with the side effect or indication, such as aspartate transaminase (AST) being related to the liver with an indication of hepatitis. Accordingly, weights may vary depending on the identified indication or side effect. The analyzer may perform any type or form of shortest path analysis, including Dijkstra's algorithm, a Bellman-Ford algorithm, or any other type and form of routing algorithm. Such analysis may, for example, indicate to include entities 506 and not include entities 508 in the example embodiment of FIG. 5A.

In other embodiments, the set of entities may be augmented by scoring nodes in the global molecular entity graph with respect to their inclusion in a subnetwork with desired properties. In one embodiment, modifying scores may include increasing scores related to an organ associated with the indication or side effect and reducing scores of unrelated nodes. In another embodiment, scores may be modified by increasing scores of nodes well connected to other nodes within the subnetwork and decreasing scores of nodes well connected to other nodes external to the subnetwork. This may minimize connectivity to the remainder of the network, reducing the likelihood of false positives and, if incorporated with the above discussed embodiments, decreasing complexity of a shortest path analysis.

In still other embodiments, pre-defined pathways within the global molecular entity network (e.g. glycolysis, cAMP-dependent pathway, etc.) may be scored with respect to their coverage of the indication-relevant entities or entities known to be associated with identified medications associated with the indication or side effect. Merging high-scoring pathways may thus allow generating an indication-specific subnetwork.

Figure 5B:
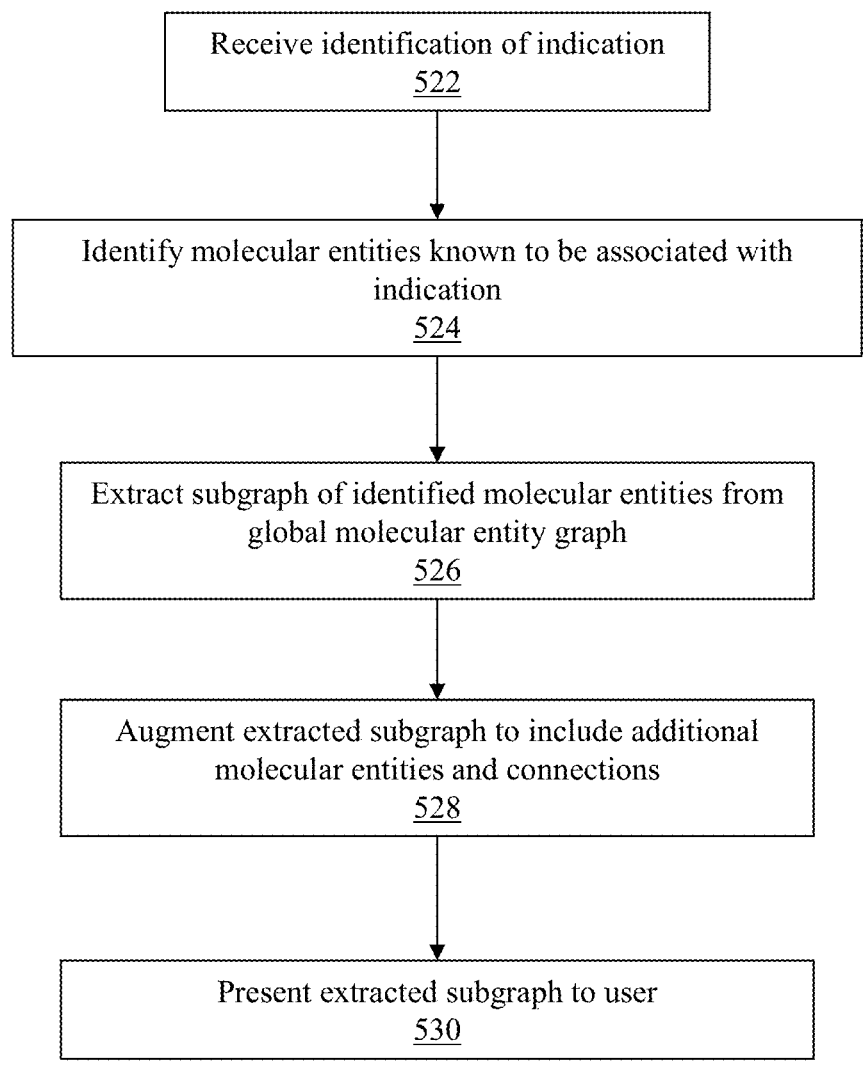
FIG. 5B is a flow diagram of an embodiment of a method for extracting an indication-specific model from a global molecular entity graph.

Referring now to FIG. 5B, illustrated is a flow diagram of an embodiment of a method for extracting an indication-specific model from a global molecular entity graph. In brief overview at step 522, an analyzer or an input/output module in communication with an analyzer may receive an identification of an indication or side effect. At step 524, the analyzer may identify molecular entities known to be associated with the indication or side effect. At step 526, the analyzer may extract a subgraph of the identified molecular entities from a global molecular entity graph. At step 528, the analyzer may augment the extracted subgraph to include additional molecular entities and inter-connections. At step 530, the analyzer may present the extracted subgraph to the user.

Still referring to FIG. 5B and in more detail, at step 522, an analyzer executed by a computing device may receive an identification of an indication or side effect. In some embodiments, the analyzer may receive the indication from an input/output module of the computing device. A user may select or enter the indication or side effect into an input interface, such as an application interface or web page interface. In many embodiments, the user may use an application on a second computing device to enter or select the indication, and the second computing device may transmit the entered indication to the input/output module of the computing device.

At step 524, in some embodiments, the analyzer may identify one or more molecular entities known to be associated with the selected or identified indication. Identifying a molecular entity known to be associated with the selected or identified indication may comprise, in some embodiments, retrieving adverse event data associated with the selected or identified indication. As discussed above, adverse event data associated with the indication may comprise one or more adverse event records including identification of consumed medications. In some embodiments, the medications in adverse event records may be identified in or linked to corresponding molecular entity information, such as via a medication information database. Accordingly, by identifying an indication, then medications associated with the indication, and then molecular entities such as protein targets associated with the medications, the analyzer may identify molecular entities associated with the indication. In some embodiments, such as where an adverse event database comprises medication information as discussed above, adverse event records may comprise molecular entity information, and thus, the analyzer may directly identify medications associated with the indication.

As discussed above, in some embodiments, the analyzer may generate a list of identified molecular entities. Such list may be ordered through various statistical techniques, including PRR, regularized PRR, logistic regression, or other means. In many embodiments, the analyzer may include in the list only entities appearing in adverse event records at a greater rate than a predetermined percentage or number threshold or corresponding to medications appearing in adverse event records at a greater rate than the predetermined percentage or number threshold. This may help reduce false positives and incidental, unrelated signals.

At step 526, the analyzer may extract a subgraph of the identified molecular entities from a global molecular entity graph. Extracting the subgraph may comprise identifying a network comprising each of the identified molecular entities and augmenting the network at step 528 with one or more additional entities and/or connections, using any of the techniques discussed above. For example, in some embodiments, extracting the subgraph may comprise selecting pairs of the identified molecular entities and performing a shortest path analysis to identify one or more intermediate entities to be included in the subgraph. In other embodiments, extracting the subgraph may comprise scoring additional nodes in the network and adding the nodes to the subgraph based on node scores being above a predetermined threshold. As discussed above, nodes may be scored based on their relationship to the indication, their relationship to an organ associated with the indication, their relationship to a pathway associated with the indication, their relationship to other nodes external to the subgraph or internal to the subgraph (for example, decreasing the score of a node with large numbers of connections to nodes not included in the subgraph or increasing the score of a node with large numbers of connections to nodes included in the subgraph), or other similar relationships. In some embodiments, extracting the subgraph may comprise scoring pre-defined pathways in the global molecular entity graph with respect to their coverage of the identified molecular entities and merging high scoring pre-defined pathways to generate the subgraph network. Accordingly, in many embodiments, steps 526 and 528 may be considered as combined steps of extracting a subgraph based on the identified molecular entities and augmenting the subgraph with additional nodes using the techniques discussed herein.

At step 530, in some embodiments, the analyzer or an output module connected to the analyzer may present the extracted and augmented subgraph to a user. In some embodiments, the subgraph may be presented as a visual graph. In many such embodiments, the visual graph may be generated by a display module, as discussed above. For example, the display module may generate a visual graph of the molecular entities and interconnections as an image, and may relocate entities as necessary to avoid intersecting connections. In some embodiments, the display module may generate an interactive image allowing entities to be selected for additional information, moved or highlighted, or otherwise manipulated. In some embodiments, the subgraph may be presented as an index or array of molecular entities and connected entities. In a further such embodiment, entities in the subgraph may be ordered based on number of connections to other entities in the subgraph, identifying entities that may be most important to the selected indication.

Figure 5C:
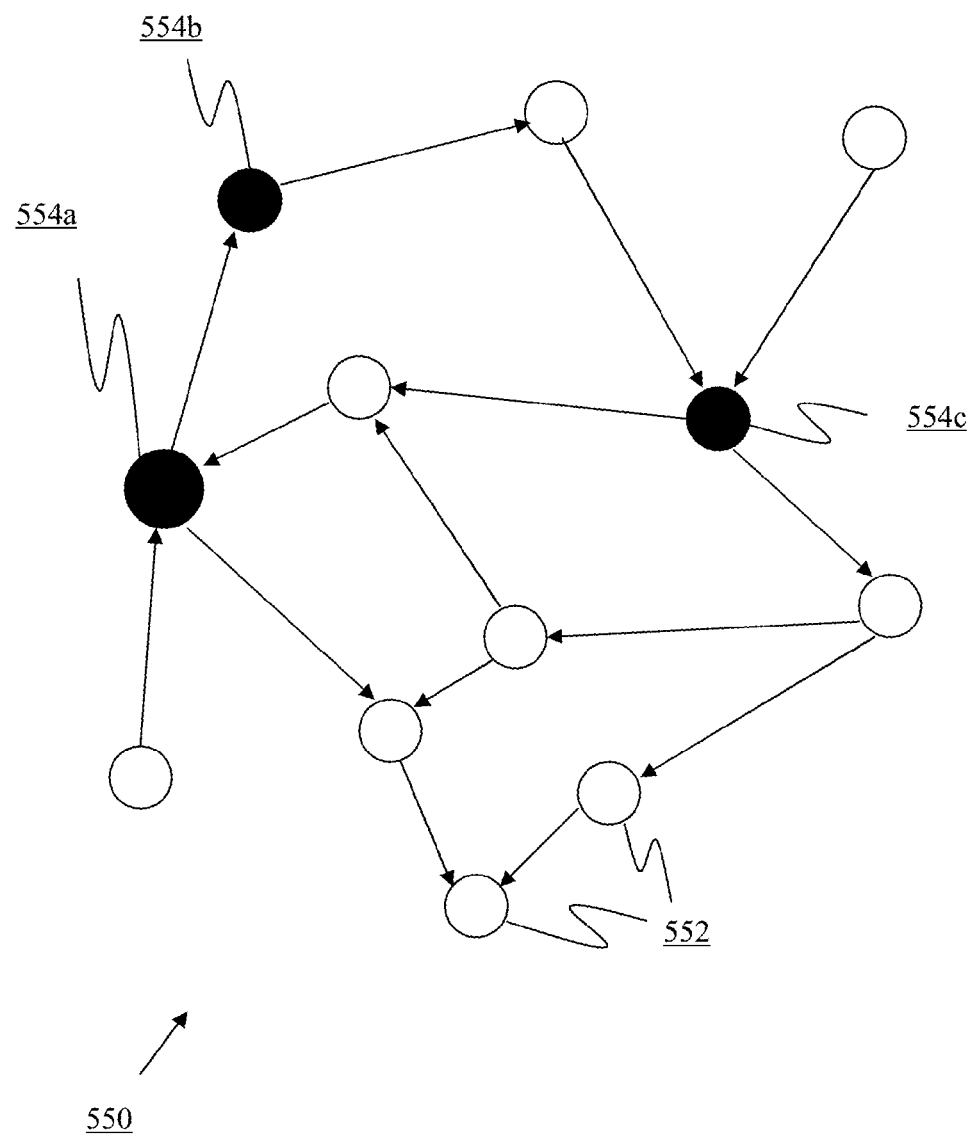
FIG. 5C is another diagram of another embodiment of a global molecular entity graph.

In some instances, activating a pathway or protein may result in different side effects or adverse events than deactivating the pathway or protein. Using the multivariate analysis techniques discussed herein, these differences may be readily examined by extracting, from a subset of adverse event data associated with a pathway or protein, a further subset of adverse event data based on whether a drug was an agonist or activator of the protein or pathway, or whether the drug was an antagonist or inhibitor of the protein or pathway. For example, referring briefly to FIG. 5C, illustrated is an example diagram of an embodiment of a subset of a global entity graph associated with a pathway 550. The subset may be extracted from a global molecular entity graph using any of the techniques discussed above. In some embodiments, the extracted graph may comprise one or more molecular entities 552. Some of the molecular entities may comprise entities 554a-554c that are known to be activated or inactivated by agonist or antagonist drugs. For example, a medication information database may indicate that a first molecular entity 554a is activated by a first medication, or that a second molecular entity 554b is inactivated by a second medication. In some embodiments, a molecular entity may be activated by a first medication and inactivated by a second medication. Thus, in many embodiments, a pathway or protein may be activated by one or more medications and deactivated by one or more medications. By comparing subsets of adverse event data associated with the pathway or protein based on whether the patient experiencing the adverse event consumed an agonist or antagonist, a side effect profile specific to activating or inactivating the pathway or protein may be generated, and compared to general adverse event data for the pathway or for a different activating state to generate distinct adverse event comparison profiles.

Referring now to FIG. 5C, illustrated is a flow chart of an embodiment of a method for extracting and comparing subsets of adverse event data based on activation state of a molecular entity. In brief overview, at step 570, a multivariate analyzer may receive, from a user, an identification of a molecular entity. In some embodiments, the entity may comprise a pathway, while in other embodiments, the entity may comprise a protein, or any other entity. At step 572, the analyzer may retrieve, from a medication information database, an identification of one or more medications affecting the pathway or entity. At step 574, the analyzer may identify a subset of the one or more medications that are agonists or activators of the entity or one or more entities of the pathway, or a subset of antagonists or inhibitors of the entity or one or more entities of the pathway. At steps 576, the analyzer may retrieve, from an adverse event database, adverse event data records including the identified subset of agonists or antagonists. In some embodiments, steps 574-576 may be repeated. In other embodiments, adverse event data records may be retrieved for the medications identified at step 572, to compare an overall side effect profile with an activation state profile. At step 578, the extracted records for different subsets or for the entire set of identification medications may be compared to identify one or more differences in the adverse event profiles for the activation states.

Figure 5D:
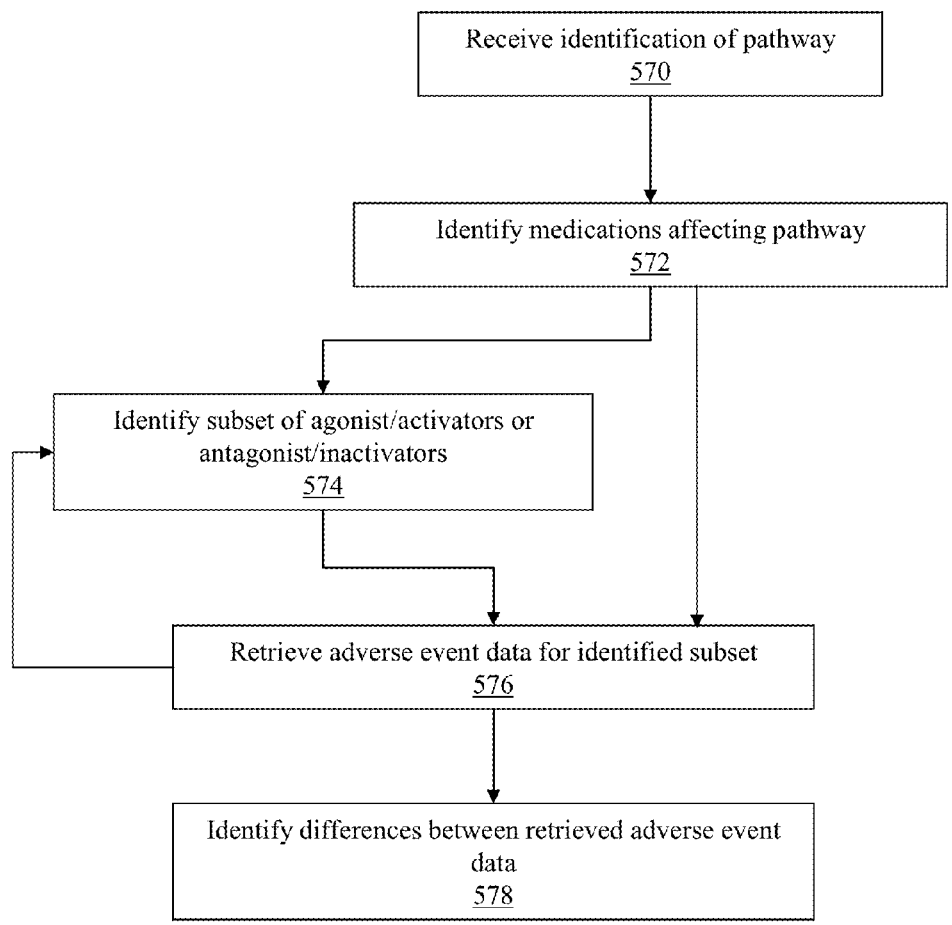
FIG. 5D is a flow diagram of an embodiment of a method for examining side effects associated with activating a pathway vs. inactivating the pathway.

Still referring to FIG. 5D and in more detail, in some embodiments, at step 570, an analyzer may receive an identification of a molecular entity from a user, such as a pathway or protein. In some embodiments, the analyzer may receive the identification via a web interface or application interface, from a remote computing device operating on behalf of the user, or from an input device connected to the computing device executing the analyzer. In many embodiments, the analyzer may receive an identification of a pathway, and may then retrieve from a global molecular entity graph or a molecular entity information database, an identification or subset of entities associated with the pathway, using any of the techniques discussed herein.

At step 572, the analyzer may retrieve, from a medication information database, an identification of medications associated with the entity. For example, in one embodiment in which the entity is a protein, the analyzer may retrieve an identification of medications known to affect the protein. In another embodiment in which the entity is a pathway, the analyzer may identify, from the global molecular entity graph or an entity database, a set of entities, including proteins, associated with the pathway. The analyzer may then retrieve, from the medication information database, an identification of medications known to affect the set of entities associated with the pathway.

At step 574, in some embodiments, responsive to a request from the user, the analyzer may identify a subset of the medications responsive to their activation or inactivation of one or more of the entities of the pathway or an identified protein. For example, in one embodiment, a user may request to identify adverse event data based on activation of the pathway, and the analyzer may identify a subset of the medications that are agonists or activators of entities of the pathway. In another embodiment, the user may request to identify adverse event data based on inhibition of the pathway, and the analyzer may identify a subset of the medications that are antagonists or inhibitors of entities of the pathway. In many embodiments, whether a medication is an agonist or antagonist of an entity may be identified in a medication information database. In some embodiments in which a medication is an agonist of one entity in the pathway and an antagonist of another entity of the pathway, such medications may be excluded from the identified subset. In other embodiments, such medications may be included in the identified subset.

At step 576, the analyzer may retrieve, from an adverse event database, adverse event data associated with the identified subset of medications. In some embodiments, retrieving the adverse event data may comprise retrieving adverse event records for a medication in the identified subset of medications, while in other embodiment, retrieving the adverse event data may comprise querying a database for records associated with the medication. In some embodiments, the analyzer may retrieve adverse event records of patients only taking medications in the identified subset of medications. In other embodiments, the analyzer may retrieve adverse event records of patients taking medications in the identified subset of medications and other medications unrelated to the pathway, but excluding medications with the other activation state of the pathway. For example, for a request for adverse event data associated with activating a pathway, the analyzer may retrieve adverse event records of patients taking any medication identified as an agonist for a protein in the pathway, but excluding any adverse event records of patients taking any medication identified as an antagonist for a protein in the pathway. This may be done to exclude adverse event data associated with patients who are consumed both activating and inhibiting medications.

In some embodiments, it may be more helpful to identify adverse event records associated with activating or inhibiting a plurality of molecular entities in a pathway. For example, inhibiting one protein in a pathway may not have the effect of inhibiting the entire pathway. Accordingly, in some embodiments, the analyzer may identify a plurality of molecular entities in a pathway, and may identify which medication in the identified subset of medications activates or inactivates which of the plurality of molecular entities. In such embodiments, the analyzer may retrieve adverse event records for patients consuming one or more medications, such that all of the identified entities was activated or inactivated by the medications. For example, in one such embodiment in which a first protein is activated by a first medication, and a second protein is activated by a second medication, the analyzer may retrieve only adverse event records associated with patients consuming both medications. Similarly, if a third medication activates both proteins, the analyzer may retrieve adverse event records associated with patients consuming the third medication. Thus, the analyzer may build a side effect profile for patients who have, through one or more medications, activated or inactivated all of the identified entities in the pathway. In some embodiments, all of the entities may be identified, while in other embodiments, certain entities of interest may be identified. Additionally, though discussed in terms of pure activation or inactivation states, the above techniques may be applied to mixed activation or inactivation states of a plurality of entities. Thus, in one example embodiment, the analyzer may retrieve adverse event of patients taking a medication that activated a first protein and inhibited a second protein, or a first medication that activated the first protein and a second medication that inhibited a second protein, allowing complex analyses.

In many embodiments, steps 574-576 may be repeated for different activation states, such as for activating a pathway vs. inhibiting the pathway. In some embodiments, adverse event data may be retrieved for all medications associated with the pathway, regardless of activation state. This may be done to provide a control group or allow comparisons to a particular activation state.

In some embodiments, at step 578, the analyzer or a display module may display side effect profiles or adverse event profiles associated with the one or more sets of adverse event data retrieved at step 576. Such profiles may comprise identifications of adverse events experienced by patients in the extracted subset of records, including identifications of adverse events over time, proportional reporting rates, an ordered list of medications, an ordered list of indications, an ordered list of outcomes, or any other data. In some embodiments, the analyzer may generate a difference profile or identify one or more differences between two profiles. For example, the analyzer may identify indications in different positions or percentages between two profiles, identify differences in the rates of adverse events, or perform other comparisons. Such difference profiles or differences may further be displayed to the user, allowing investigation into adverse event differences.

Figure 6A:
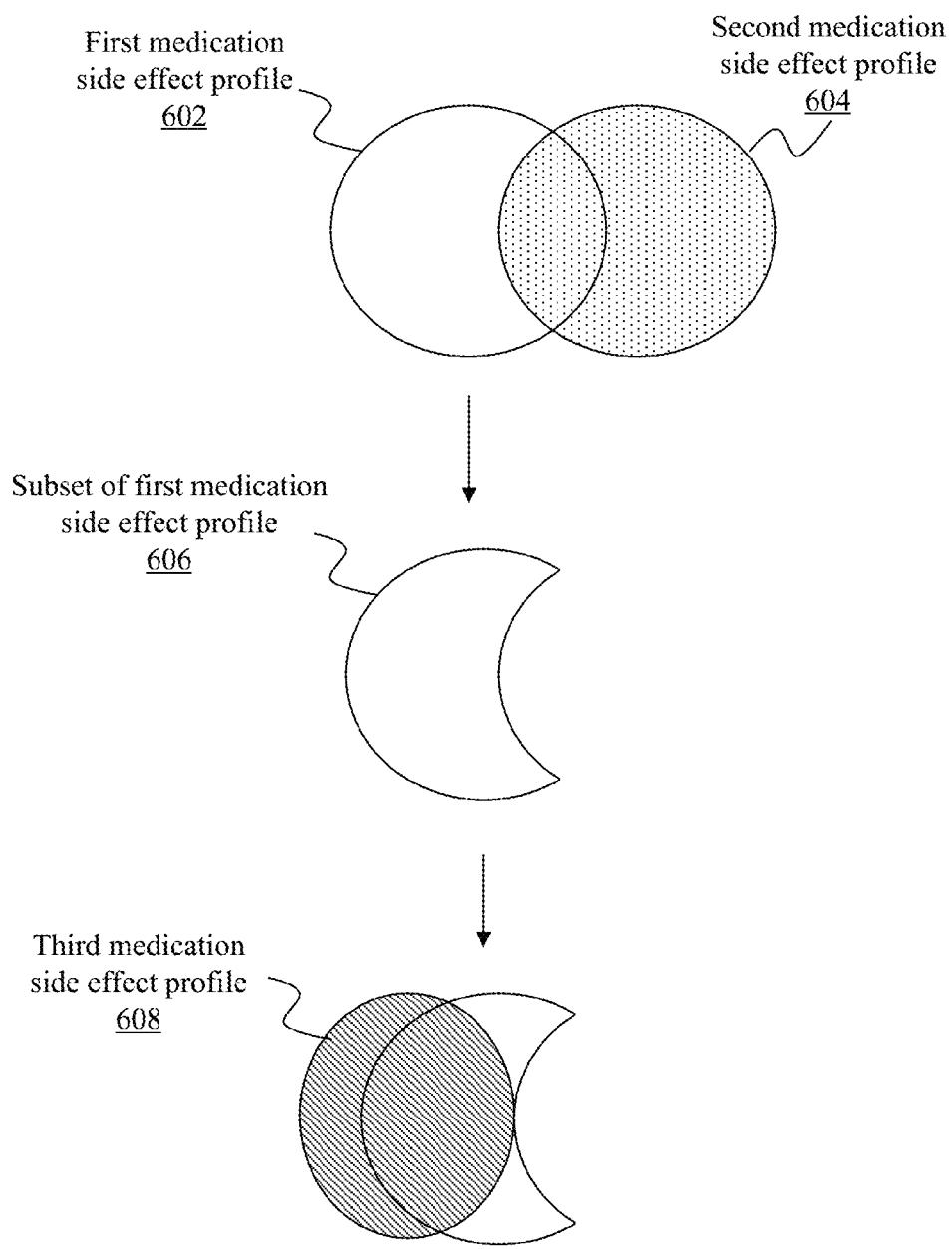
FIG. 6A is a diagram of a method of utilizing side effect profile dissimilarities to identify likely unknown targets of a medication.

Adverse event data may also be used to predicatively identify unknown targets for medications. Because adverse events may be due to physiological reactions from interaction of molecular entities with pharmaceutical compounds, a "backwards" analysis of observed adverse event data may enable identification of molecular entities previously unknown to interact with the pharmaceutical compound. Referring now to FIG. 6A, illustrated is a diagram of a method of utilizing side effect profile dissimilarities to identify likely unknown targets of a medication. A first medication may have a first side effect profile 602 comprising a statistical index of one or more side effects experienced by patients or clinical trial participants consuming the medication, in some embodiments, sorted by frequency or percentage of occurrence, as discussed above. A second, similar medication, may have a second side effect profile 604 that may share some, but not all, characteristics with the first side effect profile 602. In some embodiments, the second similar medication may comprise a second medication in the same drug class as the first medication, while in other embodiments, the second similar medication may comprise a second medication with an identified known target shared with the first medication, or known to be affecting the same molecular entity as the first medication. In some embodiments, the second side effect profile 604 may include one or more different side effects from the first side effect profile 602, or may include different frequencies or percentages of occurrence for one or more side effects from those of the first side effect profile 602. A multivariate analyzer may generate a difference profile 606 that identifies differences between the first side effect profile 602 and the second side effect profile 606. For example, a first medication such as lapatinib, may have a first side effect profile 602 that includes rash as a side effect at a very high rate, and may be known to bind to Human Epidermal Growth Factor Receptor 2 (HER2). A second medication may be selected that also binds to HER2, such as Herceptin, which may have a second side effect profile 604 that does not include rash as a side effect or includes rash only at a very low frequency. Accordingly, an analyzer may generate a difference profile or subset of the first medication side effect profile 606 that includes rash at a high frequency.

The analyzer may compare the difference profile 606 to other medication side effect profiles to identify another medication that includes the identified differences in its side effect profile 608. In some embodiments, the analyzer may limit the comparison to other medications in the same drug class or type, such as kinase inhibitors. For example, given a difference profile 606 including rash at a high frequency, the analyzer may identify that rash is also commonly associated with medications such as gefitinib and erlotinib. Known targets of the identified other medication may then be indicated as likely targets of the first medication. For example, Epidermal Growth Factor Receptor (EGFR) is a known target of gefitinib and erlotinib (as well as being a known target of lapatinib, but not Herceptin). If it was not known that lapatinib bound to EGFR, comparison of its difference side effect profile to the side effect profiles of gefitinib or erlotinib would indicate that EGFR is a likely target of lapatinib. Thus, through side effect profile comparisons and difference profiles, previously-unknown affected molecular entities for medications may be quickly identified for confirmation through targeted research.

Figure 6B:
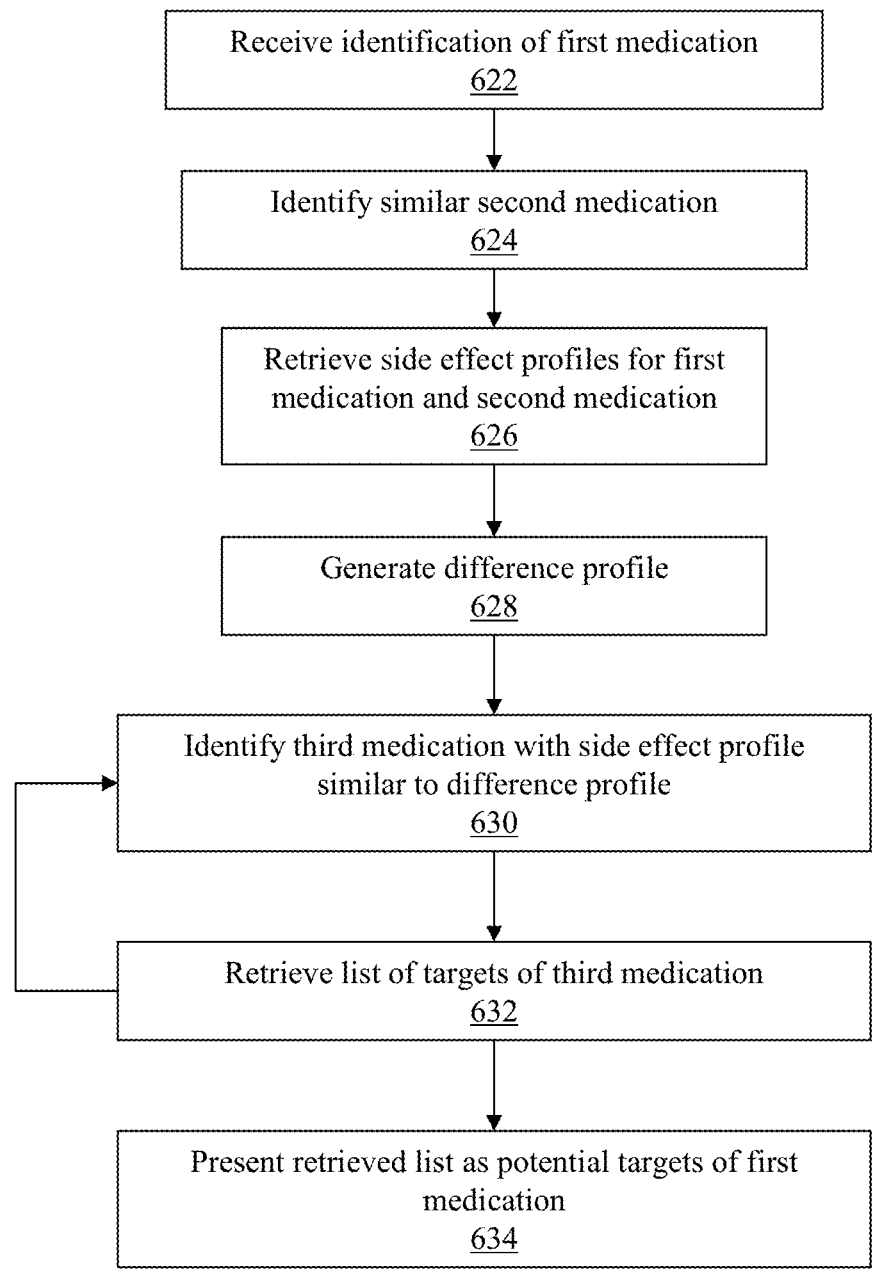
FIG. 6B is a flow chart of an embodiment of a method for identifying unknown likely targets of a first medication via comparison of adverse event data.

Referring now to FIG. 6B, illustrated is a flow chart of an embodiment of a method for identifying unknown likely targets of a first medication via comparison of adverse event data. In brief overview, at step 622, an analyzer may receive an identification of a first medication. At step 624, the analyzer may identify a second, similar medication. At step 626, the analyzer may retrieve side effect profiles for the first medication and the second medication. At step 628, the analyzer may generate a difference profile for the first medication. At step 630, the analyzer may identify a third medication with a side effect profile similar to the difference profile. At step 632, the analyzer may retrieve a list of molecular entities or targets associated with the third medication. In some embodiments, steps 630 and 632 may be repeated for a plurality of medications. At step 634, the analyzer may present the retrieved list as potential targets of the first medication.

Still referring to FIG. 6B and in more detail, at step 622, an analyzer executed by a computing device may receive an identification of a first medication. In some embodiments, the analyzer may receive the identification of the first medication from an input/output module of the computing device. A user may select or enter the medication into an input interface, such as an application interface or web page interface. In many embodiments, the user may use an application on a second computing device to enter or select the medication, and the second computing device may transmit the entered medication to the input/output module of the computing device.

At step 624, the analyzer may identify a similar second medication. In some embodiments, the second similar medication may comprise a second medication in the same drug class as the first medication, while in other embodiments, the second similar medication may comprise a second medication with an identified known target shared with the first medication, or known to be affecting the same molecular entity as the first medication. In still other embodiments, the second similar medication may comprise a medication structurally similar to the first medication.

At step 626, the analyzer may retrieve a first side effect profile associated with the first medication and a second side effect profile associated with the second medication. As discussed above, a side effect profile may comprise a statistical index of one or more side effects experienced by patients or clinical trial participants consuming the medication. The analyzer may retrieve each side effect profile by searching an adverse event database for adverse event records including the medication. In some embodiments, the analyzer may sort each side effect profile by frequency or percentage of occurrence of each side effect, as discussed above.

At step 628, the analyzer may generate a difference profile that identifies differences between the first side effect profile and the second side effect profile. In some embodiments, generating a difference profile may comprise subtracting a frequency of occurrence of a side effect in the second side effect profile from a frequency of occurrence of the side effect in the first side effect profile. In other embodiments, generating a difference profile may comprise discarding each side effect in the first side effect profile for which the second side effect profile includes the side effect at a frequency of occurrence within a predetermined threshold. For example, if a first side effect profile includes a first side effect with an 80% occurrence rate, and the second side effect profile includes the first side effect with a 75% occurrence rate, and the predetermined threshold is 10%, then the first side effect may be discarded from the resulting difference profile.

At step 630, the analyzer may identify a third medication with a third side effect profile similar to or comprising the difference profile. In one embodiment, a side effect profile is similar to the difference profile if the side effect profile includes one or more of the side effects in the difference profile at a frequency of occurrence within a predetermined threshold of the value in the difference profile. For example, if the difference profile includes a side effect with an 80% occurrence rate, and the side effect profile includes the side effect with a 65% occurrence rate, and the predetermined threshold is 20%, the side effect profile may be considered similar to the difference profile. In such embodiments, a predetermined threshold for similarity between the difference profile and the side effect profile may be the same as, or different from the predetermined threshold discussed above for generating the difference profile. In other embodiments, the analyzer may subtract a frequency of occurrence of a side effect in the difference profile from a frequency of occurrence of the side effect in the third side effect profile, and if the result is zero or within a predetermined value, the profiles may be identified as similar. In many embodiments, either of the difference profile or the third side effect profile may include additional side effects not included in the corresponding other profile. Nonetheless, a profile may be identified as similar based on similar values for identified side effects. In some embodiments, similarities must exist between a plurality of side effect occurrence frequencies before a third side effect profile may be identified as similar.

In one embodiment, the analyzer may identify the third medication by searching an adverse event database for all records including a first side effect in the difference profile. For each medication in the identified records, the analyzer may then search the adverse event database for all adverse events associated with the medication. The analyzer may then identify a frequency of occurrence of the first side effect by identifying the percentage of adverse event records for the medication which include the first side effect. This process may be repeated iteratively for additional medications and/or additional side effects to build a side effect profile for the medication. Additionally, in many embodiments, the analyzer may pre-generate side effect profiles for medications, allowing identification at step 630 to be performed quickly using the pre-generated profiles. In some embodiments, the analyzer may limit the comparison and identification to other medications in the same drug class or type.

At step 632, the analyzer may retrieve a list of targets associated with the identified third medication. In some embodiments, as discussed above, the analyzer may retrieve the list of targets from a medication information database. In many embodiments, steps 630-632 may be repeated iteratively to identify additional medications with side effect profiles similar to the difference profile.

At step 634, the analyzer may present the retrieved list of targets as potential unknown targets of the first medication. In some embodiments, the analyzer may remove from the retrieved list any known targets of the first medication, while in other embodiments, the analyzer may add any known targets of the first medication not included in the retrieved list. In some embodiments in which steps 630-632 are repeated for a plurality of medications, the analyzer may generate a union of the retrieved lists of targets, while in other embodiments, the analyzer may take an intersection of the retrieved lists of targets. This may be done to increase the number of potential targets or decrease the number of potential targets, respectively. For example, utilizing an intersection of lists of targets of medications identified as having side effect profiles comprising or at least partially similar to the difference profile may result in removing targets that are associated with less than all of the medications, and thus may not contribute to the occurrence of the side effect.

Molecular entity interactions, even for a single drug, may be complex. With multiple drugs consumed by a patient, and information about each medication in a text-based form, it may difficult to identify interactions or treatment redundancies. As a result, physicians tend to use only known drug-drug interactions in considering prescriptions. Furthermore, in many instances, patients may be prescribed drugs with redundant interactions, resulting in potential unpredictable side effects. For example, a first drug may need to be catalyzed by a first enzyme into a bioavailable compound, and the drug dosage may be calculated based on normal levels of the enzyme. If a patient is prescribed a second drug that is also catalyzed by the first enzyme, the enzyme may not be available in sufficient amounts to catalyze both drugs. In such cases, the first drug may not be present in sufficient amounts of its bioavailable form to treat the indication, or may be present in its non-catalyzed form at potentially toxic levels. Even if non-toxic, in some instances, the combination of drugs may result in one being excreted unprocessed by the patient, resulting in potentially expensive waste. Accordingly, it may be useful to physicians and patients self-managing care, as well as insurance companies or health care providers, to have an intuitive tool for examining molecular dependencies of a patient's prescription load, including all drugs, and the targets, carriers, metabolizing enzymes, transporters, pathways, and other molecular entities involved with each medication.

Figure 7A:
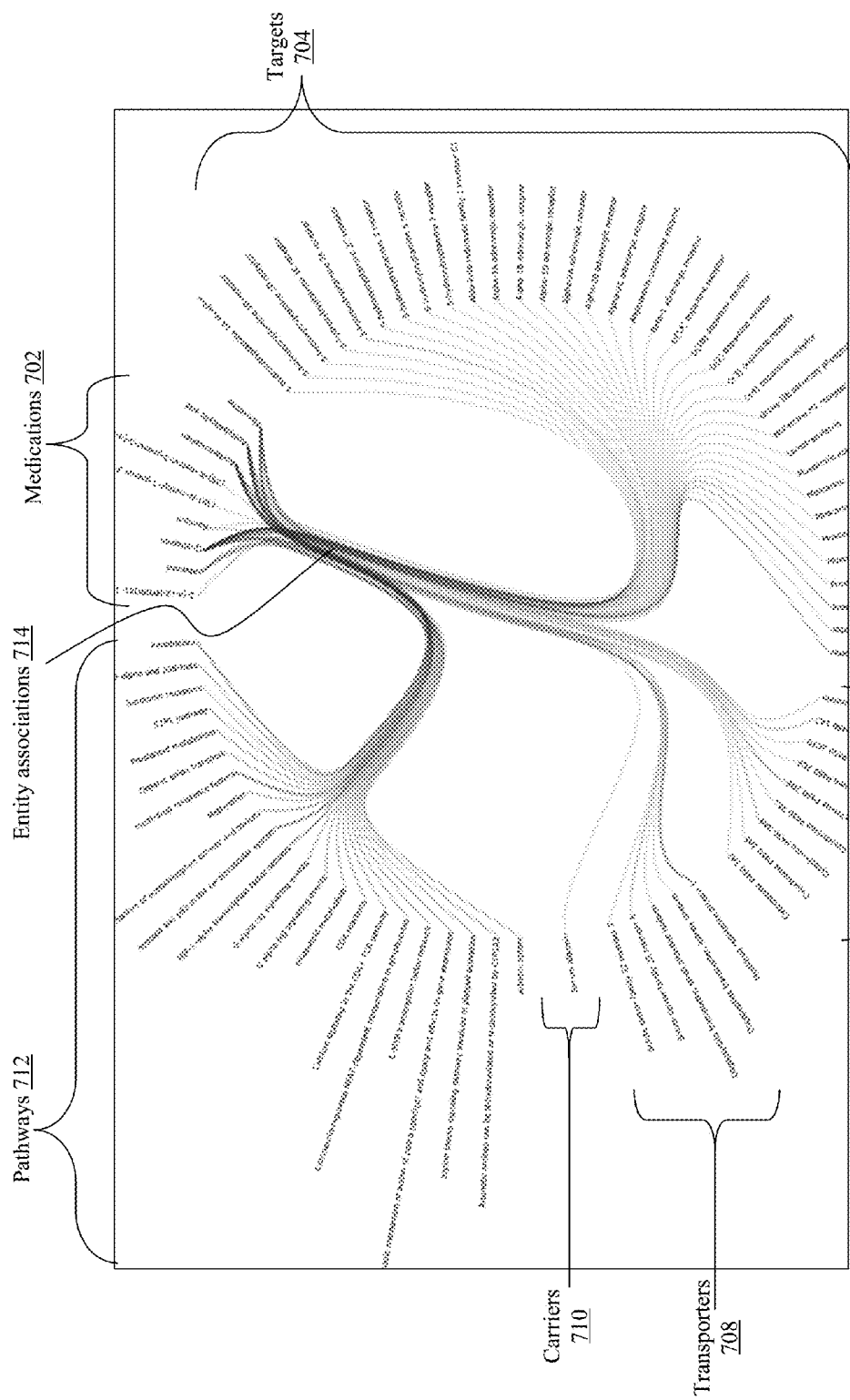
FIG. 7A-7C are screenshots of an example of embodiments of a molecular entity dependency graph that provides intuitive identification of redundancies and molecular interactions between medications in a patient's prescription load.

Referring now to FIG. 7A, illustrated is a screenshot of an example of an embodiment of a molecular entity dependency graph that provides intuitive identification of redundancies and molecular interactions between medications in a patient's prescription load. In some embodiments, a display module, embodiments of which are discussed above, may generate the dependency graph responsive to identification of a patient's prescription load. The display module and/or an analyzer may retrieve, from a medication information database, an identification of molecular entities associated with each medication prescribed to the patient and their associations and inter-associations for display in the dependency graph. In some embodiments, the dependency graph may comprise a radial graph of a plurality of molecular entities as radial entries. The molecular entities may be grouped into sub-groups of medications 702 prescribed to a patient; targets 704 of the medications 702; enzymes 706 catalyzing the medications 702; membrane transporters 708 of the medications 702; carriers 710 such as a carrier protein utilized by the medications 702; and/or pathways 712 associated with the medications 702. Molecular entities in the radial graph may be visually linked by entity associations 714. In some embodiments, the radial entries may include mapped mutational information for the patient, such as identified genetic variants for the patient. Such variants may be linked with other molecular entities in the graph, for example, corresponding protein targets 704 whose activation is modified by the variant. Although shown linking entities 704-712 to medications 702, in some embodiments, pathways 712 may be visually linked to other molecular entities such as target proteins 704 associated with the pathway. As shown, in many embodiments, entity associates 714 may comprise splines, and may be generated to be grouped with other associations between a first subcategory of entities and a second subcategory of entities. This may help to visually separate out entity associations, as opposed to depicting entity associations with straight lines from one radial entry to another. For example, a straight line from a first medication 702 to a first carrier 710 may intersect with a straight line from a second medication 702 to a target 704, potentially visually confusing the two lines. Additionally, through the use of splines as shown in FIG. 7A, a plurality of entity associations 714 from one subgroup of entities to another subgroup of entities may be substantially parallel until splitting out at each end, reducing visual confusion.

Figure 7B:
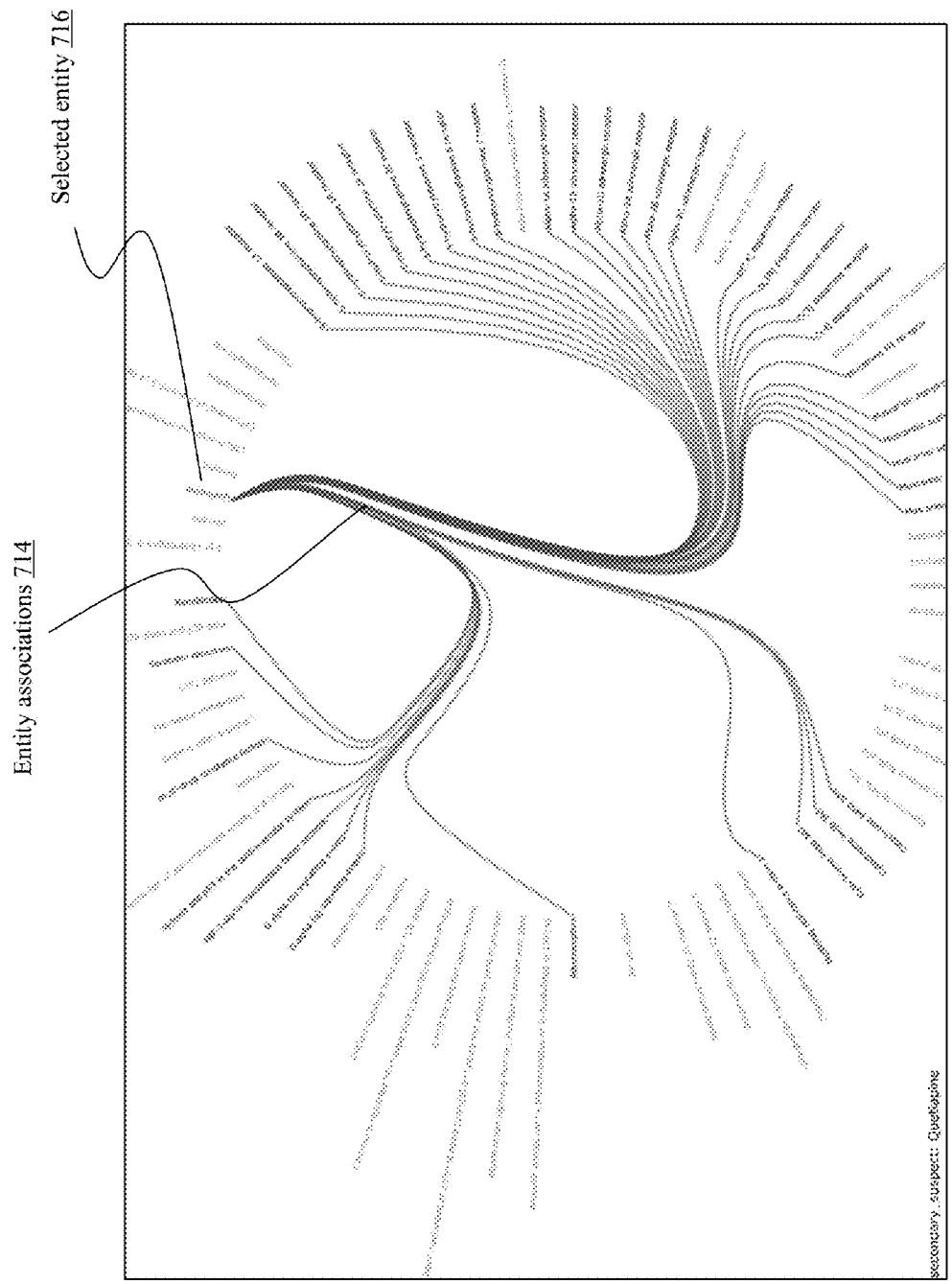

In some embodiments, the dependency graph may be interactive. For example, a display module may provide the dependency graph to an input/output module, such as a web server or server-side application, which may allow user interaction with the graph. In some embodiments, the user may select a first molecular entity, such as by clicking on the first molecular entity. In one such embodiment, the display module and/or input/output module may hide entity associations 714 not connected to the selected molecular entity. Referring now to FIG. 7B, illustrated is a screenshot of an example of an embodiment of a dependency graph allowing user interaction. As shown, in such embodiments, a user may select an entity 716, and a subgroup of entity associations 714 associated with only that entity 716 may be displayed. In some embodiments, radial entries connected to the subgroup may be highlighted or in darker text, as shown, while other radial entries may be faded or presented in lighter text, to visually distinguish associated entities and non-associated entities.

Figure 7C:
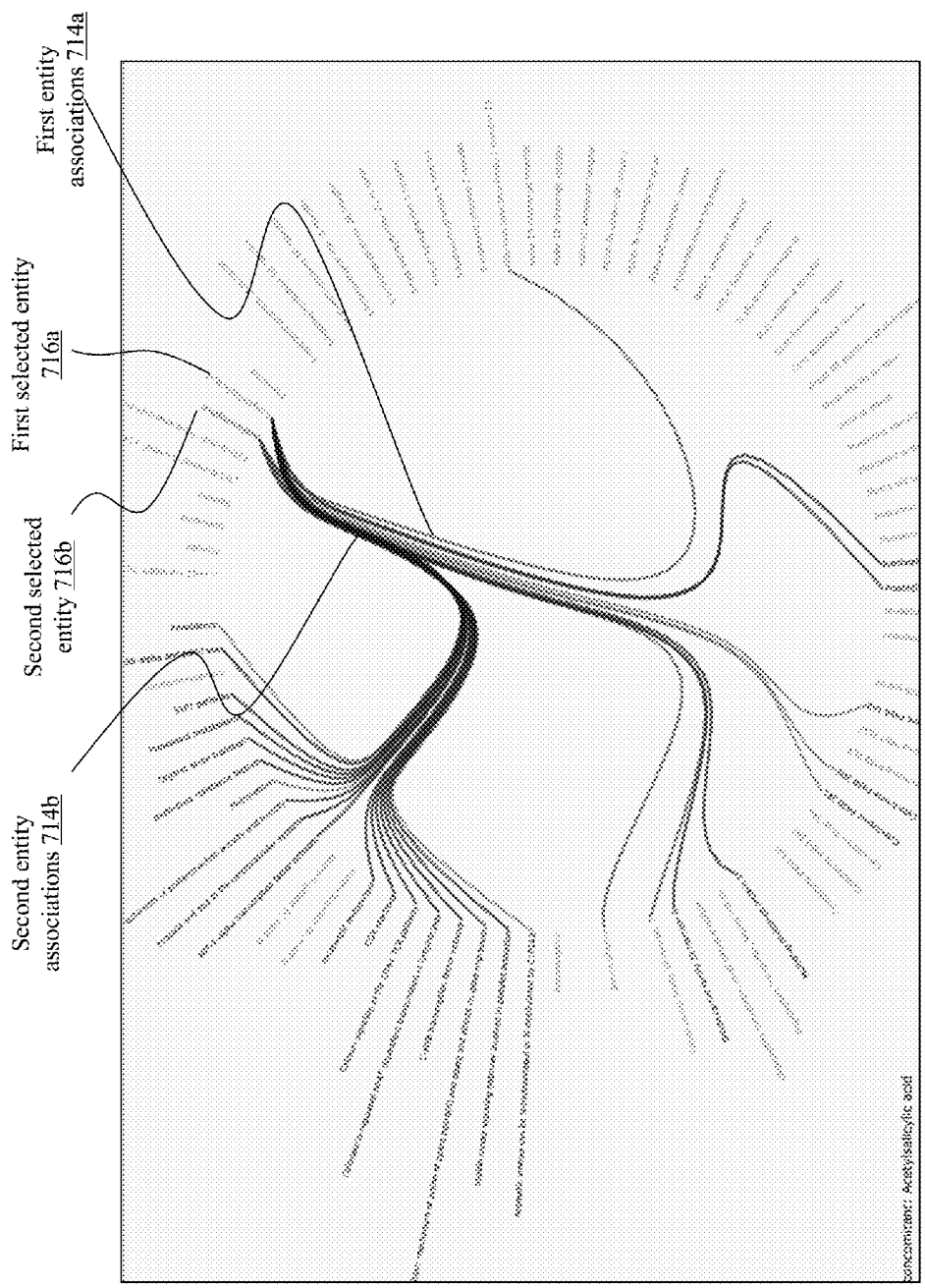

Referring briefly to FIG. 7C, illustrated is another screenshot of an example of an embodiment of a dependency graph allowing user interaction. As shown, in some embodiments, the display module and/or input/output module may be configured to allow a user to select a plurality of entities 716a-716b. The display module may display corresponding entity associations 714a-714b for each of the plurality of selected entities, allowing direct comparison of two molecular entities, such as two medications 702. In some embodiments, the display module may show entity associations 714a for a first selected entity 716a in a first color or shade, and entity associations 714b for a second selected entity 716b in a second color or shade. This may be particularly helpful when each selected entity is associated with the some of the same other entities. For example, as shown in FIG. 7C, the two selected entities 716a-716b have associations with many of the same molecular entities. In a further embodiment, associations connected to a first selected entity may be displayed in a first color, associations connected to a second selected entity may be displayed in a second color, and display module may merge the colors of overlapping associations to display a third color representing shared associations. Returning briefly to FIG. 7A, as shown, in some embodiments, the display module may be configured to optionally display selected entities and corresponding associations in a highlighted or darker color, and non-selected entities and corresponding associations in a non-highlighted or lighter color. In one such embodiment, a user need not click to select an entity, but rather the display module may highlight entities and corresponding associations 714 as the user moves a cursor over each radial entry.

In some embodiments, the dependency graph may allow a user to easily identify redundant medications. For example, a patient may be prescribed a first pain reliever and a second pain reliever, which may act in a similar way. The two medications may both be associated with many of the same molecular entities. If the two medications target different proteins, but utilize the same enzymes, transporters, and pathways, a simple target comparison may not identify a potential interaction (as well as potentially missing off-target interactions with proteins) that may cause an adverse effect or reduced efficacy of one or both medications. As the dependency graph intuitively highlights such interactions, a patient self-managing care or an insurance provider who lacks an advanced biology education may still be able to identify potential concerns or reduced efficacies for further discussion with a physician. In some embodiments, this may also allow identification of drugs with similar or identical interactions, raising questions of whether both drugs are needed for treatment. Reducing or eliminating one may reduce patient or insurance provider cost, increase efficacy of the remaining drug or drugs, and reduce unpredictable effects due to drug-drug interactions.

In some embodiments, adverse event data related to dangerous or efficacious combination therapies may be used with patient-specific genomic information to optimize or de-risk therapy for the patient. For example, in one embodiment, adverse event data may indicate that a combination therapy targeting a first protein (protein A) with a first medication (drug A) and targeting a second protein (protein B) with a second medication (drug B) may have a high rate of adverse side effects and/or negative outcomes. In addition to recognizing that drug A and drug B should not be co-prescribed to a patient, by identifying patient variants associated with the molecular entities protein A and protein B, it may even be determined that either of drug A or drug B should not be prescribed to the patient alone. For example, if the patient has a genetic mutation that inactivates protein B and drug B is an antagonist (such that normal operation of drug B blocks binding of protein B, for example), then physiologically, the patient's system may be equivalent to a normal patient consuming drug B. Accordingly, prescribing drug A alone to the patient may unintentionally result in adverse events normally seen through the combination of drug A and drug B.

Similar relationships may result based on whether the mutation is inactivating or activating of the protein, and whether the drug is an agonist or antagonist. For example, in an embodiment in which drug A is an agonist, drug B is an agonist, and the combination of drug A and drug B results in an adverse event:

a. If the patient has an activating mutation for protein A, then drug B should be contraindicated.
b. If the patient has an inactivating mutation for protein A, then drug B may be indicated.
c. If the patient has no mutation (i.e. a wildtype) for protein A, then drug B may be indicated.
d. If the patient has an activating mutation for protein B, then drug A should be contraindicated.
e. If the patient has an inactivating mutation for protein B, then drug A may be indicated.
f. If the patient has no mutation (i.e. a wildtype) for protein B, then drug A may be indicated.

Similarly, if drug A is an antagonist, drug B is an antagonist, and the combination of drug A and drug B results in an adverse event:

a. If the patient has an inactivating mutation for protein A, then drug B should be contraindicated.
b. If the patient has an activating mutation for protein A, then drug B may be indicated.
c. If the patient has no mutation (i.e. a wildtype) for protein A, then drug B may be indicated.
d. If the patient has an inactivating mutation for protein B, then drug A should be contraindicated.
e. If the patient has an activating mutation for protein B, then drug A may be indicated.
f. If the patient has no mutation (i.e. a wildtype) for protein B, then drug A may be indicated.

Likewise, if drug A is an agonist, drug B is an antagonist, and the combination of drug A and drug B results in an adverse event:

a. If the patient has an activating mutation for protein A, then drug B should be contraindicated.
b. If the patient has an inactivating mutation for protein A, then drug B may be indicated.
c. If the patient has no mutation (i.e. a wildtype) for protein A, then drug B may be indicated.
d. If the patient has an inactivating mutation for protein B, then drug A should be contraindicated.
e. If the patient has an activating mutation for protein B, then drug A may be indicated.
f. If the patient has no mutation (i.e. a wildtype) for protein B, then drug A may be indicated.

Similarly, if drug A is an antagonist, drug B is an agonist, and the combination of drug A and drug B results in an adverse event:

a. If the patient has an inactivating mutation for protein A, then drug B should be contraindicated.
b. If the patient has an activating mutation for protein A, then drug B may be indicated.
c. If the patient has no mutation (i.e. a wildtype) for protein A, then drug B may be indicated.
d. If the patient has an activating mutation for protein B, then drug A should be contraindicated.
e. If the patient has an inactivating mutation for protein B, then drug A may be indicated.
f. If the patient has no mutation (i.e. a wildtype) for protein B, then drug A may be indicated.

Although discussed in terms of a pair of interacting drugs, in many embodiments, the analysis may be extended to any number of interacting medications. For example, if it is observed that four drugs prescribed in combination results in a high rate of adverse events, patient genetic variant information relating to the molecular entities targeted by each drug may be analyzed to determine if a single drug, pair of drugs, or trio of drugs should be contraindicated, responsive to corresponding variants for three targets, two targets, or one target respectively. In other embodiments, a drug may have a plurality of target proteins, and the system may contraindicate other drugs responsive to the patient having corresponding variants for each protein. Thus, for example, if drug A is an antagonist of proteins A and C, in some embodiments, drug B may be contraindicated only if the patient has inactivating mutations for both of proteins A and C.

Figure 8:
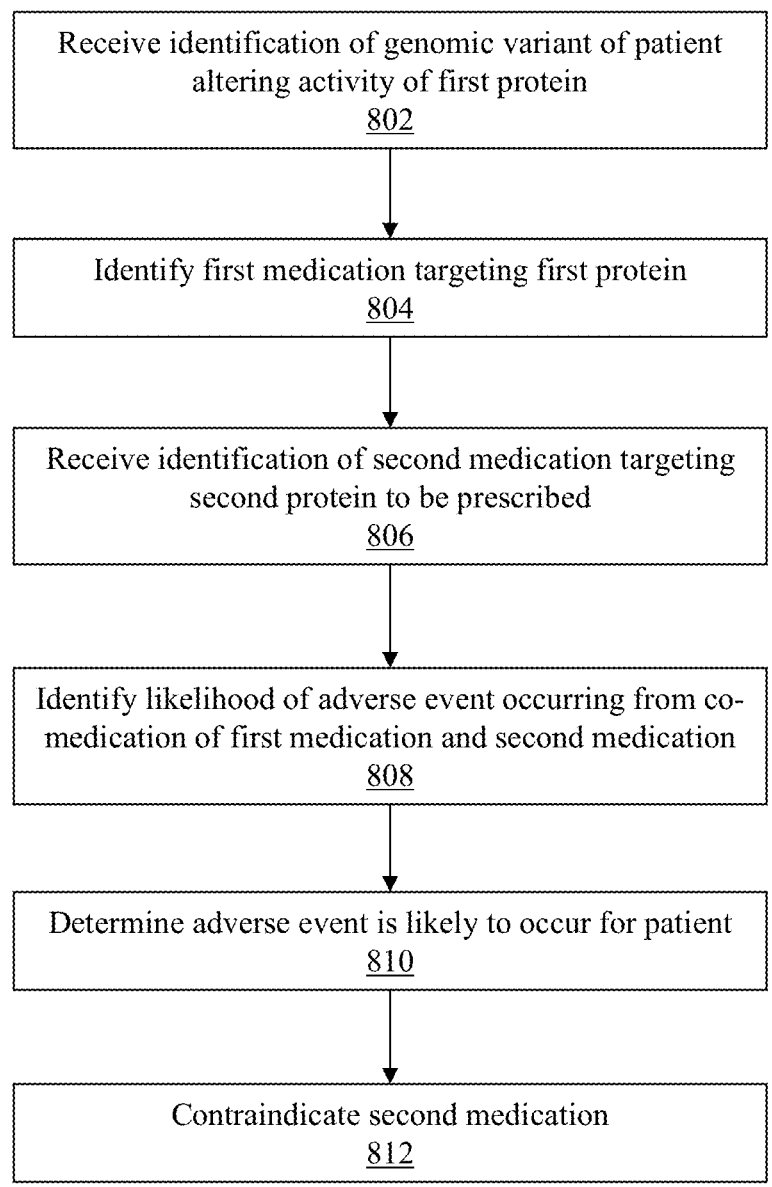
FIG. 8 is a flow chart of an embodiment of a method for personalized de-risking of medications based on genomic information of a patient and adverse event data of combination therapies.

Referring now to FIG. 8, illustrated is a flow chart of an embodiment of a method for personalized de-risking of medications based on genomic information of a patient and adverse event data of combination therapies. In brief overview, at step 802, an analyzer executed by a computing device may receive an identification of a genomic variant of a patient altering activity of a first protein. At step 804, the analyzer may identify a first medication targeting the first protein. At step 806, the analyzer may receive an identification of a second medication targeting the second protein considered as a potential medication to be prescribed. At step 808, the analyzer may identify a likelihood of an adverse event occurring from co-medication of the first medication and second medication. At step 810, the analyzer may determine that an adverse event is likely to occur for the patient. At step 812, the analyzer may contraindicate the second medication.

Still referring to FIG. 8 and in more detail, in one embodiment, an analyzer may receive an identification of a genomic variant of a patient altering activity of a first protein. In one embodiment, the analyzer may receive a list of variants of the patient. In some embodiments, in which the analyzer receives a plurality of variants, the analyzer may select a variant and repeat the method of FIG. 8 iteratively. In some embodiments, the list of variants may explicitly identify corresponding proteins, while in other embodiments, the analyzer may retrieve identifications of one or proteins corresponding to each variant from a genetic information database. In some embodiments, the analyzer may receive the identification of genomic variants from an input/output module, as discussed above. In some embodiments, a user of a second computing device may transfer or upload a list of variants to the analyzer, such as via a web interface or application.

At step 804, the analyzer may identify a first medication targeting the first protein. In one embodiment, the analyzer may search a medication information database for medications identified as targeting the first protein. In another embodiment, the analyzer may utilize an adverse event database that includes in adverse event records identification of target proteins targeted by medications consumed by the person experiencing the adverse event. The analyzer may query the database to retrieve a list of medications associated with the first protein.

At step 806, the analyzer may receive an identification of a second medication for consideration for prescription to the patient. The second medication may target a second protein. In some embodiments, a user may select a second medication from a list of medications, while in other embodiments, the user may enter a name or part of a name of a medication through a web interface or application interface, as discussed above.

At step 808, the analyzer may determine whether an adverse event is likely to occur if both the first medication and second medication are prescribed to a patient. In some embodiments, the analyzer may query an adverse event database to retrieve an identification of a number of adverse event records including both medications as consumed by the person experiencing the adverse event. The adverse event database may, in some embodiments, identify a number of times each drug was prescribed or number of times the combinations of drugs were prescribed, such that the analyzer may determine a ratio of adverse event occurrences to total number of prescriptions. In other embodiments, such as where such non-adverse event data is unavailable, the analyzer may query the adverse event database to determine a ratio of serious outcomes to total number of adverse events for the combination of medications. For example, if a serious outcome, such as death or disability occurs in the majority of adverse event reports for the two medications, the combination may be considered to have very high risk. In comparison, if a serious outcome occurs in only a slim minority or none of the adverse event reports, with non-serious outcomes dominating the records, then the combination may be considered to have a low risk. Thus, in such embodiments, the analyzer may determine whether an adverse event including a serious outcome is likely to occur if both the first medication and second medication are prescribed to a patient.

At step 810, the analyzer may determine that an adverse event is likely to occur for the patient if the patient is prescribed the second medication, responsive to determining that an adverse event is likely to occur if the patient comedicated with the first medication and the second medication and that the patient has a genetic mutation affecting a protein corresponding to activity of the first medication with the protein. As discussed above, this determination may be responsive to whether the mutation is activating or non-activating, and whether the medication is an agonist or antagonist, respectively.

At step 812, responsive to determining that an adverse event is likely to occur for the patient if the patent is prescribed the second medication, the analyzer may contraindicate the second medication. In some embodiments, contraindicating the medication may comprise generating a list of contraindicated medications for display to the user.

As discussed above, in many embodiments, steps 806-812 may be iteratively repeated for additional medications, to de-risk a patient's prescription load. Accordingly, at step 808, the analyzer may search for adverse events with a pair of medications, trio of medications, or more medications, responsive to the number of medications identified by the user. Additionally, in some embodiments, steps 806-812 may be iteratively repeated for alternate, similar medications to the identified second medication. For example, in one such embodiment, having determined that the patient will likely experience an adverse event upon consuming the identified second medication, the analyzer may repeat steps 806-812 for a third medication in the same drug class or type as the second medication. For example, if the analyzer identifies that, due to a genetic mutation in a patient and based on adverse event data, the patient will likely experience an adverse event upon consuming gefitinib, the analyzer may repeat the analysis for erlotinib, another kinase inhibitor. If the analyzer determines that the third medication may not induce an adverse effect in the patient, the analyzer may identify the third medication as a potential alternate prescription. This may allow the system to automatically identify safer alternative medications for consideration.

Furthermore, in a similar embodiment, patient genomic information may be used to determine if, for example, a mutation in a protein will decrease the binding affinity of a specific drug, leading to the drug building up to toxic levels and causing adverse events if consumed by the patient. Such proteins may comprise any proteins that interact with and/or are critical to the mode of action, metabolism, or passage of the drug through the patient system, or otherwise directly interact with the drug at the pharmacokinetic or pharmacodynamics levels. Accordingly, in such embodiments, the model of the drug's passage and mode of action within the patient system may be analyzed against patient variant information. This may allow identification of mutations in genes that do not directly interact with the drug, but whose functions regulate the activity of a gene or protein that does. Similarly, in some embodiments, the above methods and systems may be used to identify mutations in genes that affect the expression or binding affinities for off-target proteins that may lead to adverse events. For example, over-expressed off-target proteins may act as "molecular sinks" for a drug, decreasing the therapeutic efficacy of the medication. Identifying such interactions with the above-discussed systems may allow contraindication of apparently unrelated medications, reducing the incidence of previously unpredictable adverse events.

Furthermore, by collecting and analyzing patent-specific genomic information, adverse event profiles may be generated based on a genetic mutation. For example, variant identifications of patients that suffered a specific adverse event may be compared to identify genetic commonalities, which may be used to potentially de-risk new patients.

In another embodiment, homologous family members of proteins may be identified as likely off-target candidates. For example, using knowledge about the diseases caused by mutations in these candidates, the analysis system may predict potential adverse events induced by consumption of drugs targeting the homologous family members by the patient.

In some embodiments, a multivariate analysis system may be able to reduce false signals in planned clinical trials by identifying medications to be contraindicated for a cohort. For example, in many instances, a disease and a side effect may differ only due to the side effect being drug-induced. Accordingly, the side effect may be thought of as a drug-induced disease. For manufacturers and researchers developing new pharmaceuticals, it may be important during trials to avoid including patients taking other drugs that may induce the same side effect as the disease in question. Furthermore, it may be desirable to screen all patient co-medications for drug interactions at many levels, including on a molecular basis.

In some embodiments, it may be desirable to exclude drugs from a proposed clinical trial with side effect profiles that include side effects corresponding to a disease that is the subject of the clinical trial. For example, in one embodiment, if a proposed clinical trial is examining the effect of drug A in indication A, but adverse event data indicates that a side effect corresponding with indication A is also inducible by drug B, then the analysis system may contraindicate drug B from the clinical trial. The inclusion of such contraindicated drugs may result in false negatives, as they have a chance of counteracting any therapeutic effects of drug A on the disease. In another embodiment, if a clinical trial is examining the combined effects of two approved drugs for investigation into potential combination therapies, the analysis system may be used to examine the safety profile of the combination and include potential safety issues in the trial protocol.

In some embodiments, as discussed above, analysis may be performed on a molecular basis. For example, in one such embodiment with a first drug targeting a first protein to be used for a clinical trial, a multivariate analysis system may retrieve a side effect profile for the protein, based on adverse event data for all medications targeting the protein. In other embodiments, molecular entities functionally related to the protein may be identified, and side effect profiles for medications targeting those molecular entities may be retrieved. In many embodiments in which molecular entity information is integrated into adverse event records as discussed above, side effect profiles may be generated for the molecular entities directly, and then medications associated with high risk entities may be identified for contraindication.

Figure 9:
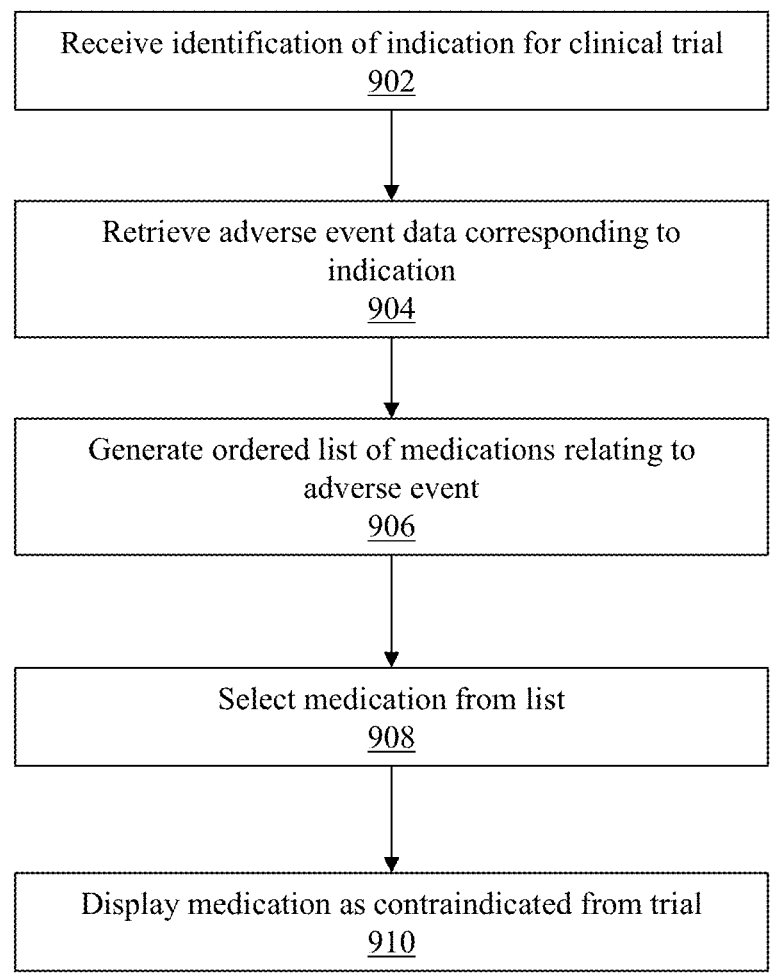
FIG. 9 is a flow chart of an embodiment of a method for identifying a medication for contraindication from a clinical trial of another medication.

Referring now to FIG. 9, illustrated is a flow chart of an embodiment of a method for identifying a medication for contraindication from a clinical trial of another medication. In brief overview, at step 902, an analyzer executed by a computing device may receive an identification of an indication for a clinical trial. At step 904, the analyzer may retrieve adverse event data for a side effect corresponding to the indication. At step 906, the analyzer may generate an ordered list of one or more medications consumed by patients that experienced the side effect. At step 908, the analyzer may select one or more medications from the list, and at step 910 may display the one or more medications as contraindicated from the clinical trial.

Still referring to FIG. 9 and in more detail, at step 902, an analyzer executed by a computing device may receive an identification from a user of an indication for a clinical trial. In some embodiments, the user may select or enter the indication via a web interface or application interface. The user may utilize the same computing device or a second computing device connected to the first computing device via a network.

In some embodiments, at step 904, the analyzer may retrieve adverse event data for a side effect corresponding to the indication from an adverse event database. In some embodiments, the analyzer may query the database for records including the side effect corresponding to the indication. Such records may comprise identifications of the side effect and outcome experienced by the patient, medications consumed by the patient, patient demographic information, and any other relevant information. In some embodiments, the records may comprise identifications of molecular entities corresponding to the medications, while in other embodiments, such identifications may be in a second medication information database.

At step 906, the analyzer may generate a list of medications identified in each retrieved record. In some embodiments, the analyzer may count the number of times each medication appears in the retrieved records in order to order the list via frequency of appearance. In some embodiments, each medication may be scored in the list or have an associated frequency value and/or statistical percentage or rate of appearance. In some embodiments, the analyzer may determine one or more statistical measures for the medication, such as reporting odds ratio (ROR), incidence rate ratio, or proportional reporting ratio (PRR), or may apply one or more statistical algorithms, such as a multi-item gamma poisson shrinker (MGPS) algorithm.

At step 908, the analyzer may identify one or more medications from the list to be contraindicated. In some embodiments, the analyzer may select all medications in the list to be contraindicated, while in other embodiments, the analyzer may select a subset of medications in the list. For example, in one embodiment, the analyzer may select all medications in the list associated with a particular organ that is the subject of the clinical trial. In another embodiment, the analyzer may select all medications in the list of a particular drug class or type. In still another embodiment, the analyzer may select medications having a statistical value or ratio above a predetermined threshold. For example, the analyzer may select all medications having a PRR or MGPS value over 2 and discard other medications from the list.

At step 910, the analyzer may display the identified one or more medications as medications to be contraindicated from the trial. In some embodiments, the analyzer may display one or more statistically likely side effects that may be induced by each contraindicated medication.

In some embodiments, the analyzer may further identify combinations of medications to be contraindicated for the trial. For example, in some instances, a side effect corresponding to the indication may appear when two medications are consumed by a patient, but not when either is consumed alone. From the adverse event data, the analyzer may identify that each medication is included individually in adverse event records for the side effect. The analyzer may then compare pairs or sets of identified medications for frequency of co-appearance within each retrieved record. Medications that appear together at a high frequency within the adverse event records may be identified as a contraindicated combination.

In some embodiments, a multivariate analysis of adverse event data may be further used to identify novel combination therapies for research by generating cohorts of patients conforming to specific clinical and treatment variables. Cohorts can be compared in terms of patient outcomes, with variables examined for potential clinical effects. For example, adverse event data for a first cohort of patients with cancer who have taken an anti-neoplastic agent may be retrieved and compared to adverse event data for a second cohort of patients with cancer who have taken an anti-neoplastic agent plus another class of drug. The sets of adverse event data for each cohort may be compared to identify if the other class of drug has any effect on the death rate of cancer patients across cancer indications. Drugs which appear to decrease the death rate or are associated with a lower death rate in adverse event reports may then be potential candidates for combination therapy. Furthermore, such analysis may be done for any molecular entity.

Figure 10A:
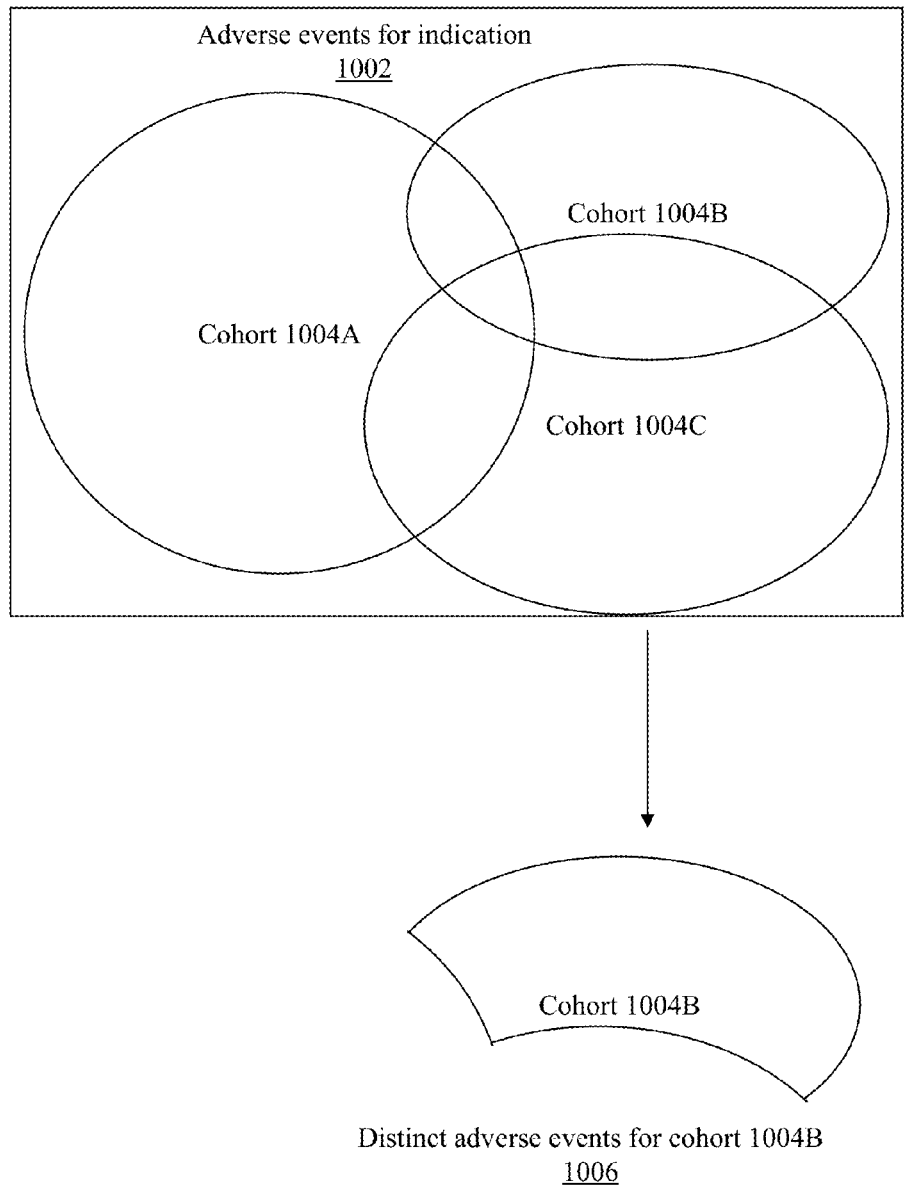
FIG. 10A is a Venn diagram of an example of an embodiment of defining cohorts within adverse event data and extracting difference profiles for a cohort.

For example, and referring briefly to FIG. 10A, illustrated is a Venn diagram of an example of an embodiment of defining cohorts within adverse event data and extracting difference profiles for a cohort. Adverse event data for an indication 1002 may be retrieved from an adverse event database through a query by an analyzer. The query may further comprise additional variables to define cohorts 1004A-1004C or patients defined by the variable, and adverse event data for each cohort may be retrieved. In many embodiments, patients may be in multiple cohorts. For example, a first cohort may be defined as patients who consumed a first drug, and a second cohort may be defined as patients who consumed a second drug. Accordingly, patients consuming both drugs may be placed in both cohorts. Variables for defining cohorts may be of different types. For example, a first cohort may be defined as patients who are over a specified age, and a second cohort may be defined as patients who consumed a medication that was catalyzed by a specified enzyme. The analyzer may extract a distinct adverse event profile for a cohort 1006. In some embodiments, the analyzer may compare adverse event profiles between cohorts to generate a difference profile, while in other embodiments, the analyzer may generate a query that excludes members of other cohorts from the cohort for which the distinct profile is created. In still other embodiments, the analyzer may retrieve identifications of adverse event records for each cohort, and then eliminate any records shared by each cohort. The analyzer may then determine rates of various outcomes for the records identified in the difference profile, and may compare this to rates of various outcomes for other cohorts, or the indication as a whole. Differences in the rates may thus indicate potential combination therapies.

Figure 10B:
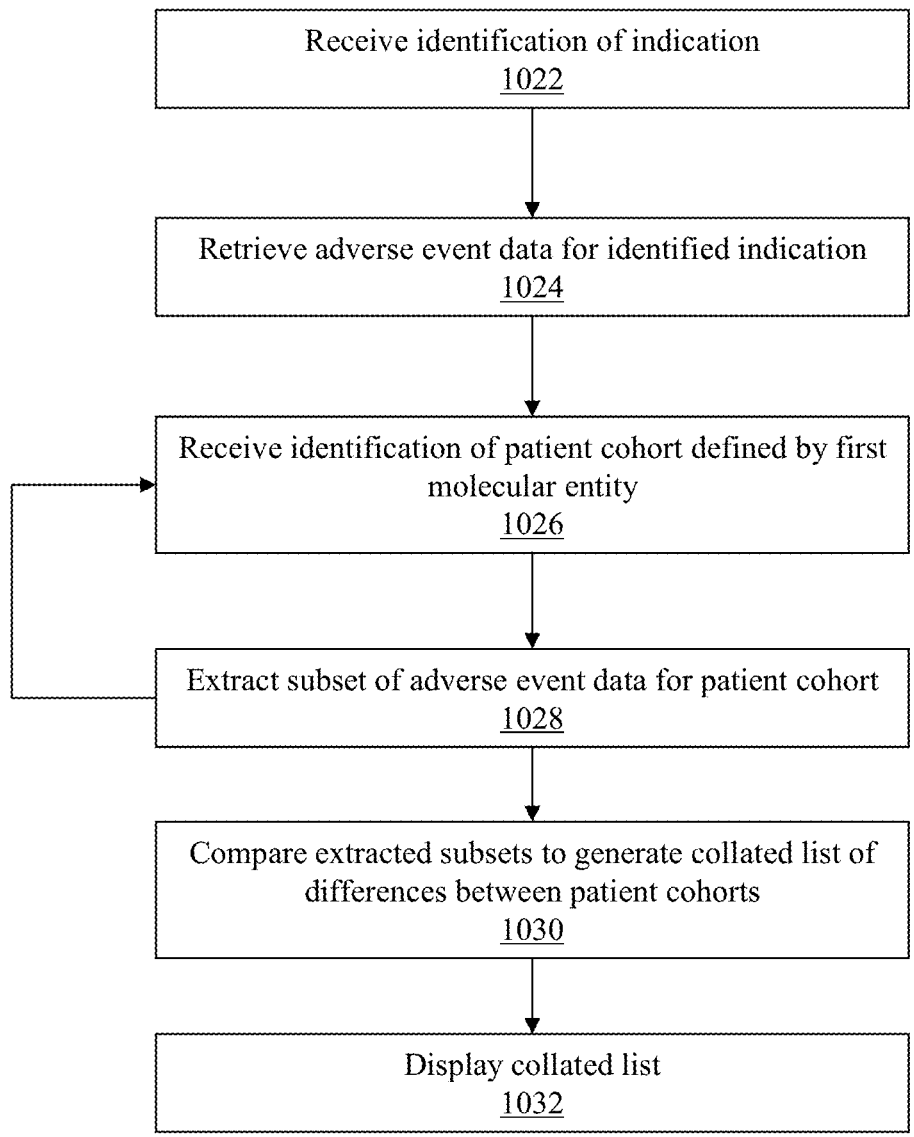
FIG. 10B is a flow chart of an embodiment of a method for identifying potential combination therapies for research via adverse event data.

Referring now to FIG. 10B, illustrated is a flow chart of an embodiment of a method for identifying potential combination therapies for research via adverse event data. In brief overview, at step 1022, an analyzer may receive an identification of an indication. At step 1024, the analyzer may retrieve adverse event data for the identified indication. At step 1026, the analyzer may receive an identification of a patient cohort. In many embodiments, the patient cohort may be defined by a molecular entity, while in other embodiments, the patient cohort may be defined by demographic information or a genotype. At step 1028, the analyzer may extract a subset of adverse event data for the patient cohort. In some embodiments, steps 1026-1028 may be repeated for additional cohorts. At step 1030, the analyzer may compare the extracted subsets to generate a collated list of differences between the patient cohorts. At step 1032, the analyzer or an output module connected to the analyzer may display the collated list of differences. Although shown in one order in FIG. 10B, as discussed above, in some embodiments in which the analyzer uses multivariate queries with Boolean operations to retrieve adverse event data from the adverse event database, many of the steps may be collapsed into a single step.

Still referring to FIG. 10B and in more detail, in one embodiment at step 1022, an analyzer may receive an identification of an indication from a user. In some embodiments, the analyzer may receive the identification via a web interface or application interface communicating via an input/output module. As discussed above, the user may operate an application on the same computing device as the analyzer, or on a different computing device communicating with the first computing device via a network.

At step 1024, in some embodiments, the analyzer may retrieve adverse event data for the identified indication from an adverse event database. As discussed above, adverse event data may comprise records of adverse events experienced by patients, and may identify an indication for which the patient was being treated or may identify a side effect experienced by the patient corresponding to the indication.

At step 1026, the analyzer may receive an identification of a first patient cohort. The patient cohort may be defined by a molecular entity, such as patients consuming a first medication, patients consuming a medication targeting a first protein, patients consuming a medication targeting a first pathway, patients consuming a medication related to a first drug class, etc. In other embodiments, the patient cohort may be defined by demographic information, such as age or gender, or may be defined by patients having specified genetic mutations or wildtypes. In many embodiments, multiple variables may be used to define a patient cohort, such as men over 50 being treated for high cholesterol.

At step 1028, the analyzer may extract a subset of adverse data experienced by the identified first patient cohort. In some embodiments, the analyzer may extract data relating to side effects experienced by the first patient cohort being treated for the identified indication, while in other embodiments, the analyzer may extract data relating to patient outcomes of the first patient cohort. Such data may comprise raw numbers of adverse events for each side effect and/or outcome, or proportional reporting ratios or other statistical identifiers for each side effect and/or outcome. The analyzer may repeat steps 1026-1028 for a plurality of cohorts with at least one modified variable, such as an included or excluded molecular entity, changed demographic information, etc.

At step 1030, the analyzer may compare the extracted subsets for different patient cohorts to identify statistical differences between side effects and/or outcomes between cohorts. In one embodiment, comparing the extracted subsets may comprise generating difference values for each statistical value of a side effect and/or outcome. For example, if 30% of a first cohort is listed as having died as a result of the indication and/or side effect, and 10% of a second cohort is listed as having died as a result of the indication and/or side effect, a difference value of −20% may be identified for the second cohort. In many embodiments, difference values beyond a predetermined threshold may indicate a potentially significant result of the modified variable between the cohorts. In some embodiments, comparing the extracted subsets of adverse event data may comprise generating an index of side effects and/or outcomes experienced by the patients and sorting the index by percentage or raw number. The analyzer may then compare the positions of individual side effects and/or outcomes within the generated index for each cohort. In many embodiments, the analyzer may generate a collated list of one or more statistical differences between the side effect profiles for each cohort. As discussed above, in many embodiments, the list may be limited to statistical differences above a predetermined threshold, such as difference percentages over a predetermined rate, or altered index positions greater than a predetermined number.

At step 1032, the analyzer or a display module or output module connected to the analyzer may display the generated list of statistical differences to the user. The list may be used to identify statistically significant differences in adverse events experienced by each cohort, and potentially attributable to the modified variable or variables between the cohorts. This may point to potential combination therapies for reducing risk or increasing efficacy of therapy.

Figure 11A:
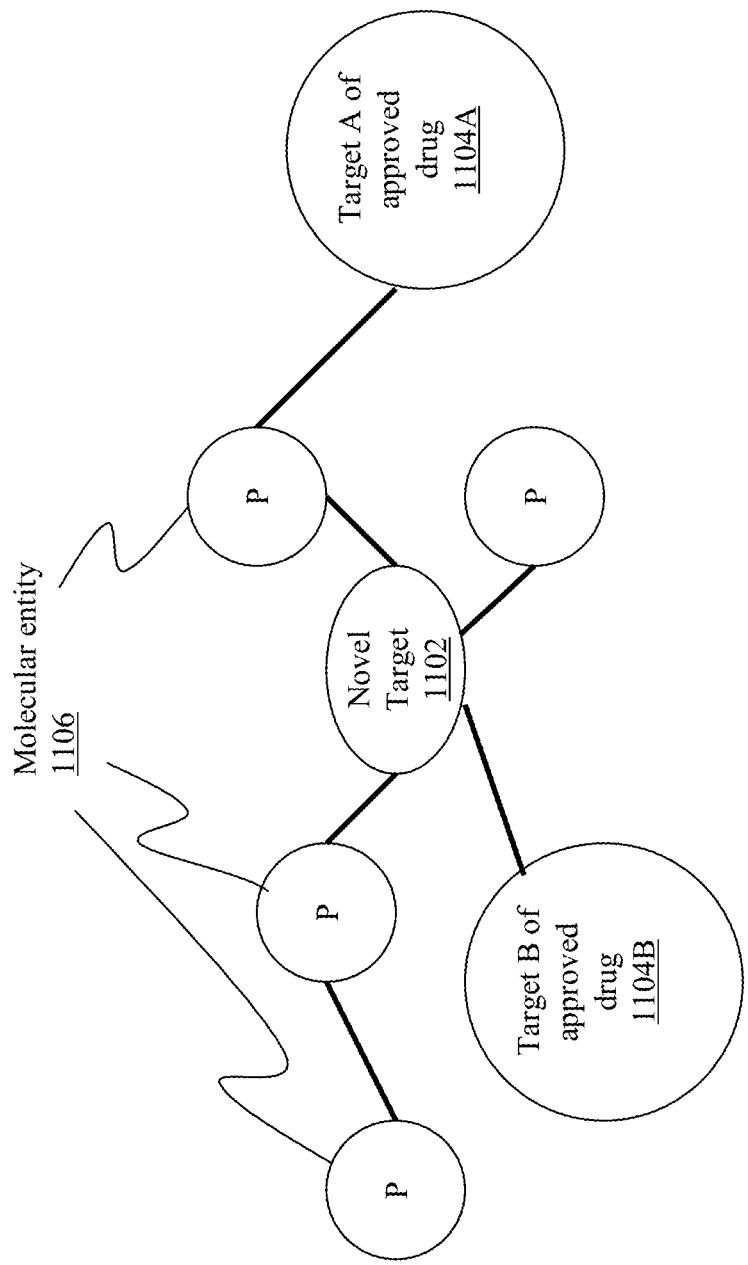
FIG. 11A is a graph of an example of a region of an example embodiment of a global molecular entity graph or molecular entity network comprising a plurality of molecular entities 1106 connected via functional links.

By integrating an adverse event database with molecular entity information, such as the global molecular entity graph discussed above, a multivariate analysis system may be able to predict a likely side effect profile for even new, untested medications. Specifically, a predicted side effect profile may be generated based on intersections of side effect profiles of other medications that affect the same or related molecular entities, such as the nearby target proteins, involve the same pathways, or are otherwise similarly related. To generate a predicted side effect profile for a new drug targeting a novel or previously un-targeted protein target, an analyzer may query an adverse event database for records pertaining to patients who have taken drugs or combinations of drugs that target or affect molecular entities in the vicinity of the novel target within a global molecular entity graph. By examining the side effect profiles associated with the connected targets, one can look for commonalities that might also be expected with the novel target. For example, referring briefly to FIG. 11A, illustrated is a graph of an example of a region of an example embodiment of a global molecular entity graph or molecular entity network comprising a plurality of molecular entities 1106 connected via functional links. To generate a predicted side effect profile for a new drug targeting novel target protein 1102, an analyzer may query an adverse event database for adverse event records of patients who consumed a first approved drug targeting a first protein A 1104A; adverse event records of patients who consumed a second approved drug targeting a second protein B 1104B; and records of patients who consumed both drugs. Intersections and/or difference profiles may be generated based on these retrieved adverse event records to a generate side effect profile of adverse event records that likely involved the novel target 1102, even if it was not realized at the time. For example, a patient who consumed both the first drug and second drug targeting proteins A and B likely affected their processing of the novel target protein 1102, for example by reducing availability of an enzyme needed to catalyze the protein 1102, resulting in higher systemic levels of the protein than normal. In some embodiments, this may have a similar effect as a novel drug that acts as an agonist of the protein, for example. Accordingly, side effects experienced by such a patient may be similar to side effects that may be experienced by a patient consuming the novel drug.

Figure 11B:
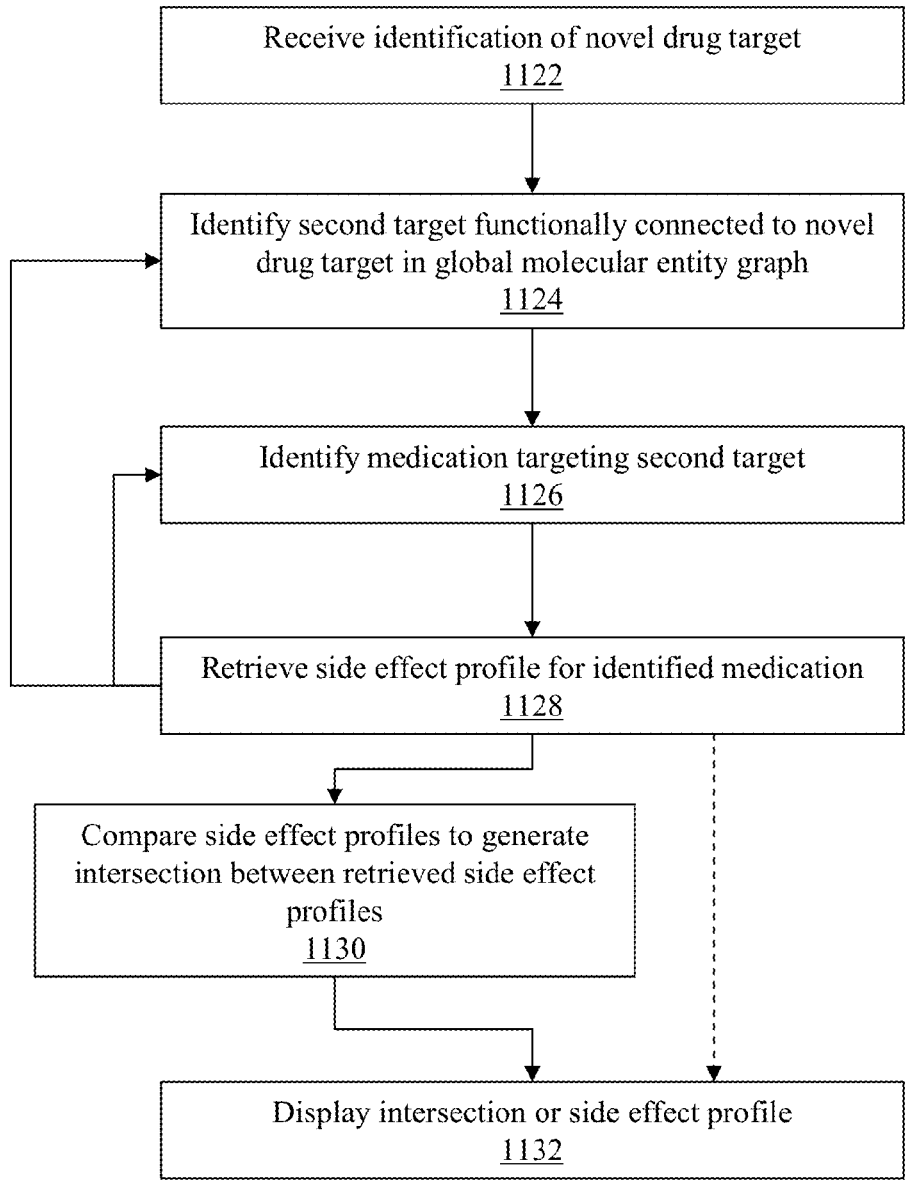
FIG. 11B is a flow chart of an embodiment of a method for generating a predicted side effect profile for a medication targeting a novel target.

Referring now to FIG. 11B, illustrated is a flow chart of an embodiment of a method for generating a predicted side effect profile for a medication targeting a novel target. In brief overview, at step 1122, an analyzer or input module may receive an identification of a novel drug target. At step 1124, the analyzer may identify a second target functionally connected to the novel drug target in a global molecular entity graph. At step 1126, the analyzer may identify a medication targeting the second target. At step 1128, the analyzer may retrieve a side effect profile for the identified medication targeting the second target. In some embodiments, the analyzer may output the retrieved side effect profile at step 1132 for display to the user as a predicted side effect profile of the novel drug target. In many embodiments, the analyzer may repeat steps 1126-1128 to retrieve side effect profiles for one or more additional medications targeting the second target, while in other embodiments, the analyzer may repeat steps 1124-1128 to identify one or more additional targets and additional medications. At step 1130, the analyzer may generate an intersection side effect profile of the retrieved side effect profiles, and at step 1132, may output the retrieved side effect profile for display to the user as a predicted side effect profile of the novel drug target.

Still referring to FIG. 11B and in more detail, at step 1122, an analyzer executed by a computing device may receive an identification of a novel drug target from a user. The novel drug target may comprise a molecular entity, such as a protein, enzyme, transporter, or other entity that may be known, but not previously targeted by a medication. Functional relationships or connections to other molecular entities from the novel drug target may also be known, such as the inclusion of the novel drug target in a global molecular entity graph. In some embodiments, the analyzer may receive the identification of the novel drug target via an application executed by the computing device used by the user, while in other embodiments, the analyzer may receive the identification via a web interface or application interface via a network from a second computing device.

At step 1124, the analyzer may identify a second target functionally connected to the novel drug target in a global molecular entity graph. In one embodiment, the analyzer may select a nearby drug target using a shortest path algorithm. In another embodiment, the analyzer may select a nearby drug target with the most interconnections to nodes also connected to the novel drug target. For example, if the novel drug target is connected to five additional nodes, two of which are also connected to a first target and three of which are connected to a second target, the analyzer may select the second target based on the additional shared node. In some embodiments, a combination of these approaches may be used. For example, the analyzer may select a nearby target that has the most independent paths to the novel target of less than a predetermined length. In some embodiments, the analyzer may even select such a target over a second target that has fewer, but shorter paths. For example, if a first nearby target has five paths to the novel target, each path traversing one intermediate node (i.e. length two), the analyzer may select this target over a second nearby target that has only one path that directly connects to the novel target (i.e. length one). In some embodiments, nearby targets may be selected based on their relationship to the same organ involved with the first target. In other embodiments, nearby targets may be scored based on their inclusion in a common pathway or pathways with the novel target, and the analyzer may select the highest scoring target. In still other embodiments, nearby targets may be scored based on their number of connections to nodes in a shared pathway with the novel target. In a further embodiment, a target's score may be reduced based on its number of connections to nodes in pathways not shared with the novel target. In still other embodiments, combinations of a plurality of these techniques may be used to generate a score for each nearby target, and the analyzer may select a high scoring target. In repeated iterations, the analyzer may select additional targets scoring above a predetermined threshold.

At step 1126, the analyzer may identify a medication targeting the second target. In one embodiment, the analyzer may query a medication information database for one or more medications identified as targeting the second target. In some embodiments, the analyzer may identify medications that are known to have off-target effects on the second target. In some embodiments, the analyzer may identify a plurality of medications targeting the second target and may repeat steps 1126-1130 iteratively for each of the plurality of medications.

At step 1128, in some embodiments, the analyzer may retrieve from an adverse event database or generate from records retrieved from the adverse event database a side effect profile for the identified medication. As discussed above, the side effect profile may comprise an identification of all side effects or adverse events listed in the adverse event database as experienced by patients consuming the medication, along with a score, raw number, percentage or proportional reporting ratio, or other metric to identify a statistical rate for each side effect. In some embodiments, the analyzer may return the side effect profile as a predicted side effect profile for the novel target at step 1132 for display to the user. This may be done, for example, if the second target is only targeted by one medication. Typically, however, the analyzer may repeat steps 1126-1128 for additional medications identified as targeting the second target, and/or steps 1124-1128 for additional targets nearby the novel target in the global molecular entity graph.

At step 1130, in some embodiments, the analyzer may compare a plurality of retrieved side effect profiles to generate an intersection profile. In one embodiment, an intersection profile may comprise one or more side effects or adverse events present in each retrieved side effect profile. In another embodiment, an intersection profile may comprise one or more side effects or adverse events present in each retrieved side effect profile with a similar reporting percentage or PRR, such as within a predetermined range. This may be useful to discard false positives where a side effect profile includes large numbers of side effects only associated with a few records. In some embodiments, an intersection profile may be further differentiated by outcome. For example, the intersection profile may comprise one or more side effects or adverse events present in each retrieved side effect profile with a similar reporting percentage and similar rate of serious or non-serious outcomes. This may be an important distinction, for example, if two side effect profiles experience a side effect at the same rate, but one has a much higher rate of serious outcomes.

At step 1132, the intersection profile may be presented to the user as a predicted side effect profile for the drug targeting the novel target. In one embodiment, a display module or output module may generate a table, list or index of the intersection profile for display to the user. In some embodiments, the intersection profile may be transmitted to a second computing device for display to the user. Such predicted side effect profiles may be used to establish safety measures for a trial protocol for the drug. Furthermore, in some embodiments, while an intersection profile may be more narrowly tailored to the target protein, the analyzer may instead generate a union or combination profile at step 1130. This may be done to ensure that all potential side effects are included in the predicted side effect profile. In such embodiments, the combination profile may comprise a combination of the retrieved side effect profiles. In some embodiments, duplicate entries in the side effect profiles, such as one side effect that appears in each profile at a similar rate, may be removed. In other embodiments, duplicate entries may be more highly scored, such as with a confidence value. Thus, a side effect that appears in only one profile may be included in the combination profile but scored lower than a side effect that appears in a plurality of profiles at similar rates. The latter may be more likely to occur with the new drug. Scores or confidence values may be displayed to the user along with profile to aid in predicting likely side effects.

In some embodiments, by integrating patient or trial participant-specific genetic information with adverse event data, a multivariate analysis system may be able to identify genetic variants associated with adverse events in a clinical trial. This may enable deeper levels of interpretation of safety signals than are available through purely observational means, allowing in-depth insights into the molecular protagonists and pathways involved in eliciting drug side effects. On the one hand, a multivariate analysis may detect drugs that induce specific clinical side effects. Exploration of the underlying molecular mechanisms of offending drugs allows researchers and clinicians to hone in on the activity of targets and off-targets whose drug-induced perturbation leads to specific adverse phenotypes. On the other hand, the multivariate analysis may capture and contextualize relevant published information, providing another level of gene prioritization in association with specific side effects. Combining these techniques and integrating other clinico-molecular information may provide the ability to efficiently analyze patient specific genomic information in search of genetic factors that influence a drugs risk profile.

Figure 12A:
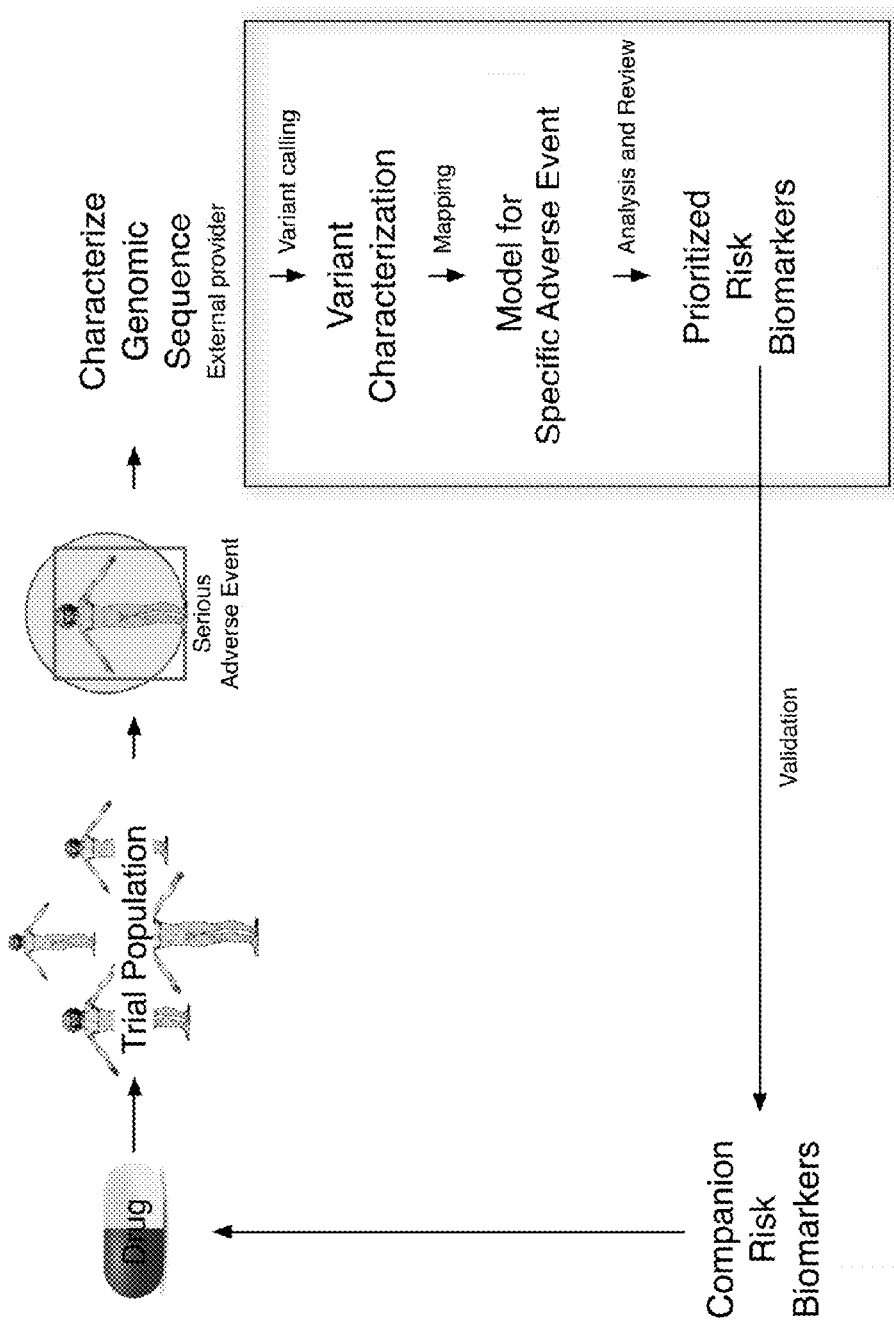
FIG. 12A is a block diagram of an embodiment of a process for using genomic information to identify protein targets responsible for adverse events.

For example, and referring briefly to the block diagram illustrated in FIG. 12A, in one embodiment involving a clinical trial where a serious and unexpected adverse reaction is encountered, a researcher may generate complete genome sequence information for the affected patient or patients, and then attempt to identify a causal genetic predisposition or predispositions to the observed effect. Such sequence information may comprise identifications of the patient's specific genetic mutations and variants. In many embodiments, the sequence information may be obtained from an external provider of genomic information. The sequence may be analyzed to detect variants from wildtypes, and each variant may be mapped to one or more corresponding molecular entities based on their relationship to the entities, such as whether they are activating or inactivating of a protein, etc. By combining information and knowledge about the molecular mechanisms associated with side effects with complete genomic sequencing, researchers can quickly identify genetic factors that may increase a patient's risk of drug-induced side effects. The multivariate analyzer may determine, from adverse event data associated with molecular entity information, which molecular entities may be responsible for an adverse event, and correspondingly, whether the event may be likely to occur in the general trial population or whether it is associated with a specific variant or variants of the affected patient.

Figure 12B:
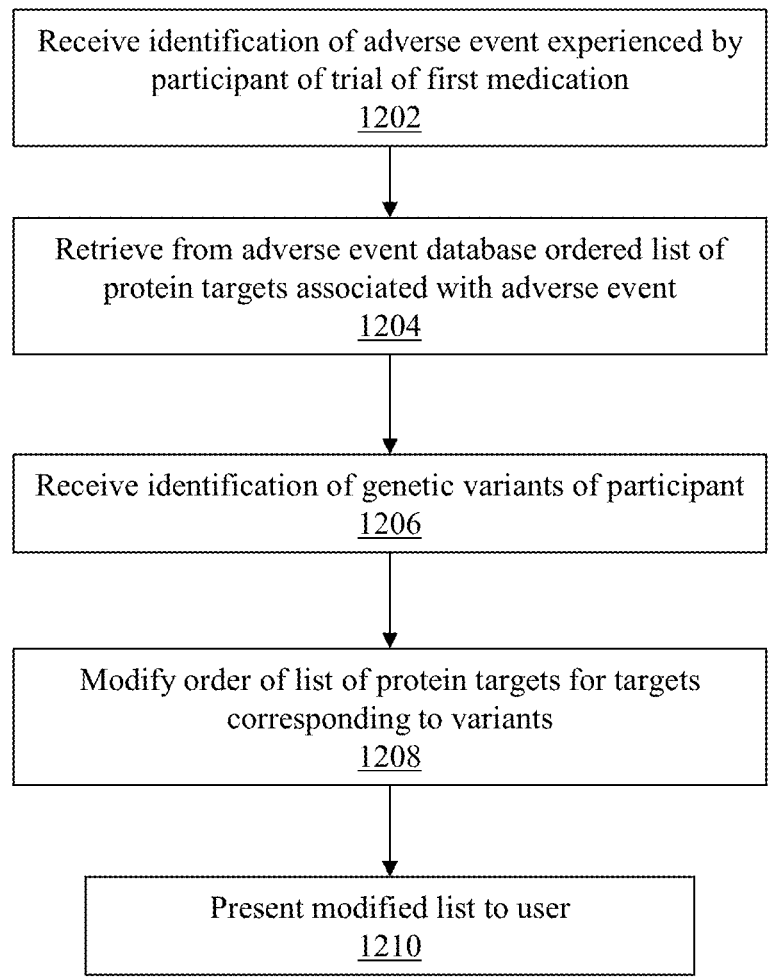
FIG. 12B is a flow chart of an embodiment of a method of identifying genetic variants associated with adverse events.

Referring now to FIG. 12B, illustrated is a flow chart of an embodiment of a method of identifying genetic variants associated with adverse events. In brief overview, at step 1202, an analyzer executed by a computing device may receive an identification of an adverse event experienced by a patient or participant in a clinical trial of a first medication. At step 1204, the analyzer may query an adverse event database for records associated with the adverse event to generate an ordered list of one or more protein targets most associated with the event. At step 1206, the analyzer may receive an identification of one or more genetic variants of the participant or patient. At step 1208, the analyzer may modify the order of the list of one or more protein targets responsive to targets in the list corresponding to the identified one or more genetic variants. At step 1210, the analyzer or an output module connected to the analyzer may output the modified list to a user as a prioritized list of variants potentially responsible for the adverse event.

Still referring to FIG. 12B and in more detail, at step 1202, a multivariate analyzer executed by a computing device may receive, from a user, an identification of an adverse event experienced by a participant of a clinical trial of a first medication. In some embodiments, the analyzer may receive the identification of the adverse event via an input module, such as a web interface or application interface. In many embodiments, the analyzer may receive the identification from a second computing device via a network.

At step 1204, the analyzer may query an adverse event database for one or more adverse event records associated with the adverse event. As discussed above, in some embodiments, each record may comprise or be linked to identifications of one or more protein targets targeted by drugs consumed by the person who experienced the adverse event for which the record was generated. In other embodiments, each record may comprise identifications of one or more medications consumed by the person who experienced the adverse event, and the analyzer may retrieve one or more corresponding protein targets for the one or more medications from a medication information database. The analyzer may generate an ordered list of the proteins based on the frequency with which the protein (or a medication targeting the protein) appears in the adverse event records. In some embodiments, the analyzer may include a PRR or percentage rate with which each protein appears in or is associated with the adverse event records. In one embodiment, the analyzer may generate a score for each protein based on the order of the protein within the list or the identified rate.

At step 1206, the analyzer may receive an identification of one or more genetic variants of the participant who experienced the adverse event in the clinical trial. In some embodiments, the user of the computing device may provide a list of variants to the analyzer, while in other embodiments, the user of the computing device may provide a full or partial genetic sequence of the participant, and the analyzer may identify one or more variants within the genetic sequence through comparison with a database of genetic wildtypes.

At step 1208, the analyzer may modify the order of the list of proteins for protein targets corresponding to identified genetic variants of the participant. In some embodiments, the analyzer may increase a score associated with each protein in the ordered list responsive to the participant having a variant associated with the protein, or decrease scores associated with each protein in the ordered list responsive to the participant not having a variant or having a wildtype associated with the protein. In a further embodiment, the analyzer may increase a score of a protein targeted by the first medication if the participant has a genetic variant corresponding to the protein. In some embodiments, the analyzer may increase the scores of proteins in the list associated with an organ related to the adverse event, such as increasing the score of proteins associated with the kidneys if the participant experienced renal failure. Accordingly, the analyzer may modify the order of the list of proteins and/or score of each protein to generate a prioritized list of potential targets inducing the adverse event in the participant. At step 1210, the analyzer or an output module may present the modified list to the user as a prioritized list of proteins potentially responsible for the experienced adverse event. In a further embodiment, the analyzer or output module may present the modified list with corresponding genetic variants of the patient. Accordingly, the list may identify the genetic variants and proteins most likely to be associated with inducing of the adverse event.

It may be helpful to briefly discuss examples of embodiments of an interface for performing multivariate analysis of adverse event data. One skilled in the art may readily appreciate that many other interfaces may be utilized, and as such, the examples should be considered non-limiting.

Figure 13A:
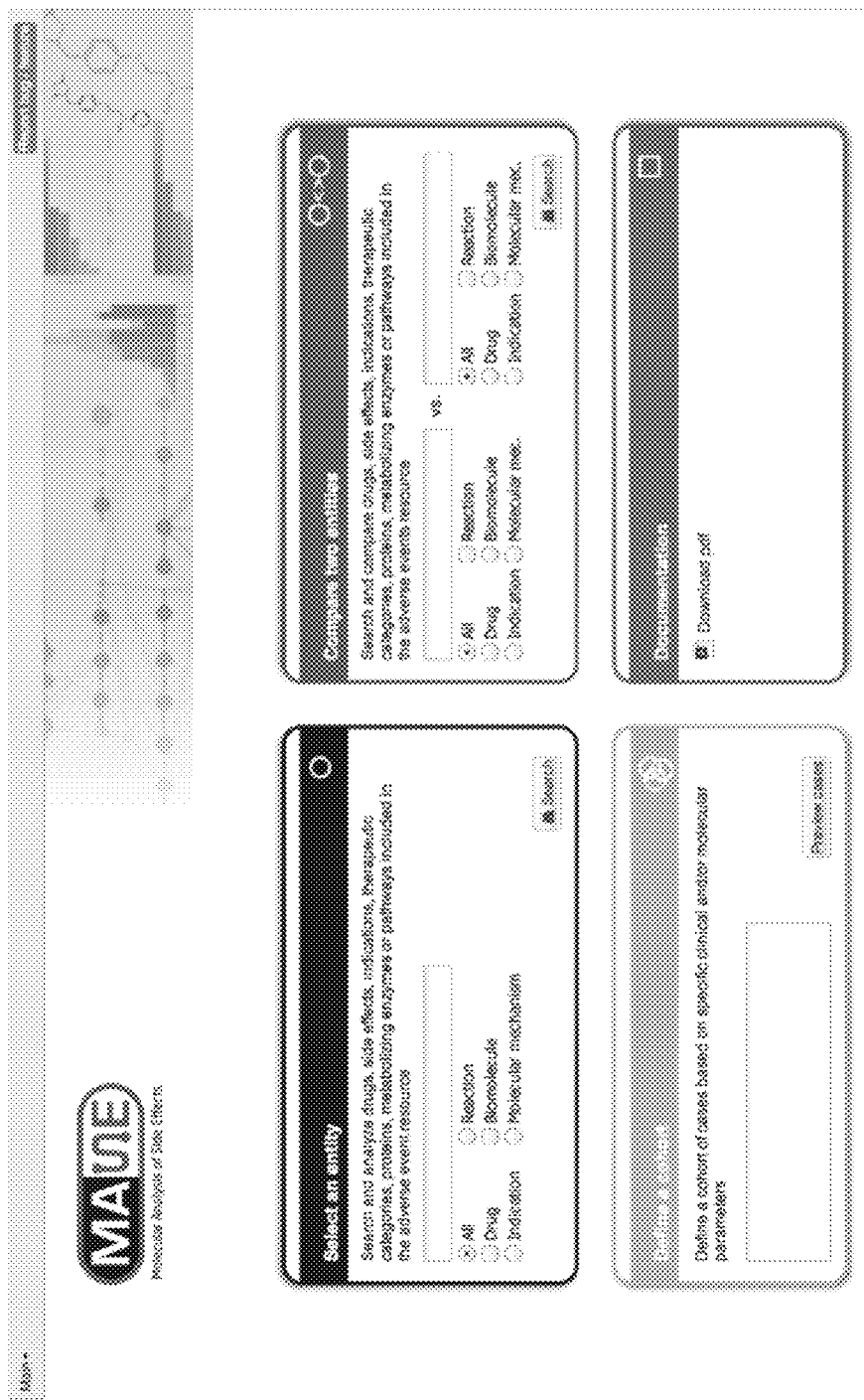
FIGS. 13A-13Y are screenshots of an example embodiment of an interface for analyzing adverse event data.
Figure 13B:
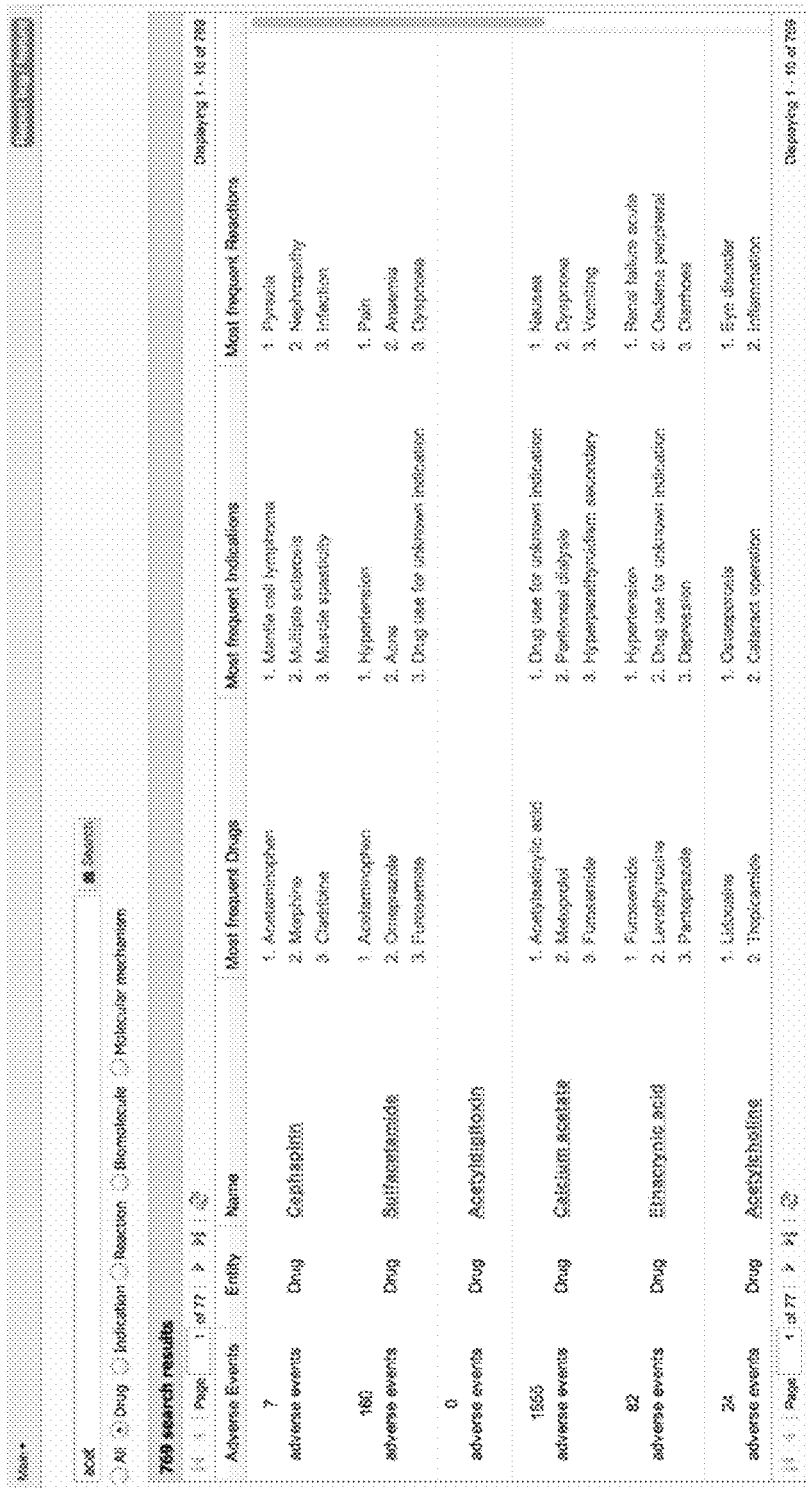
Figure 13C:
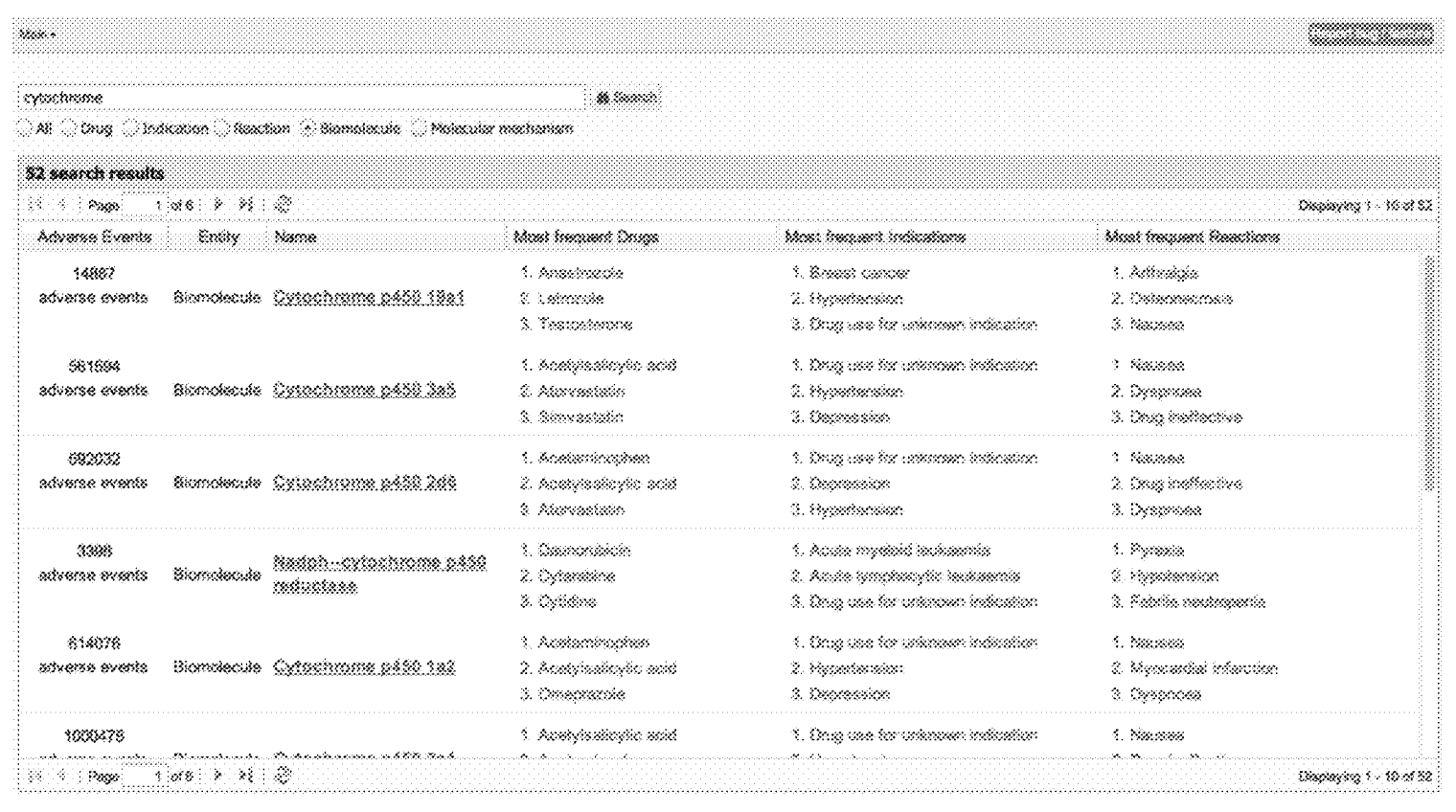
Figure 13D:
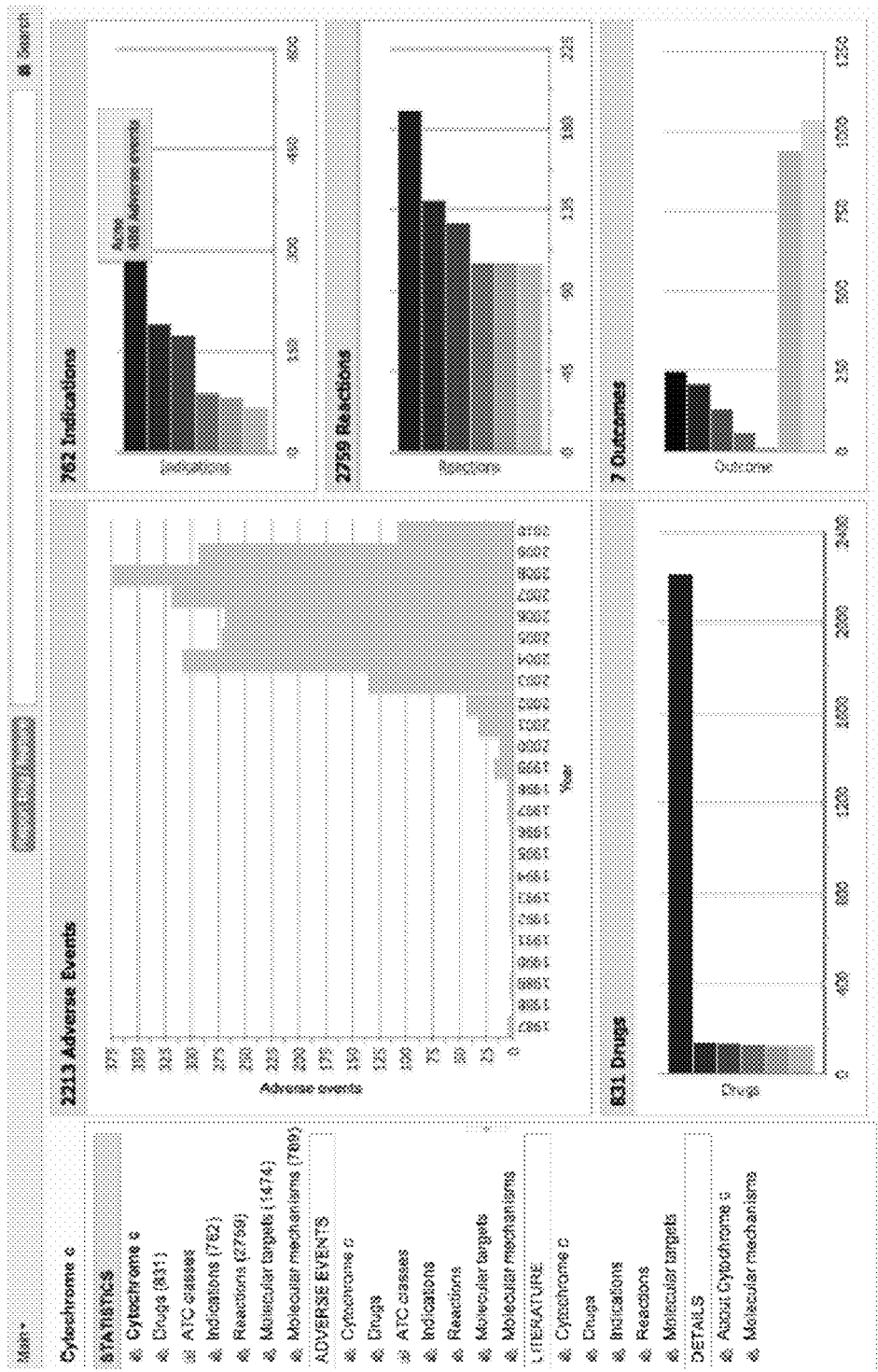
Figure 13E:
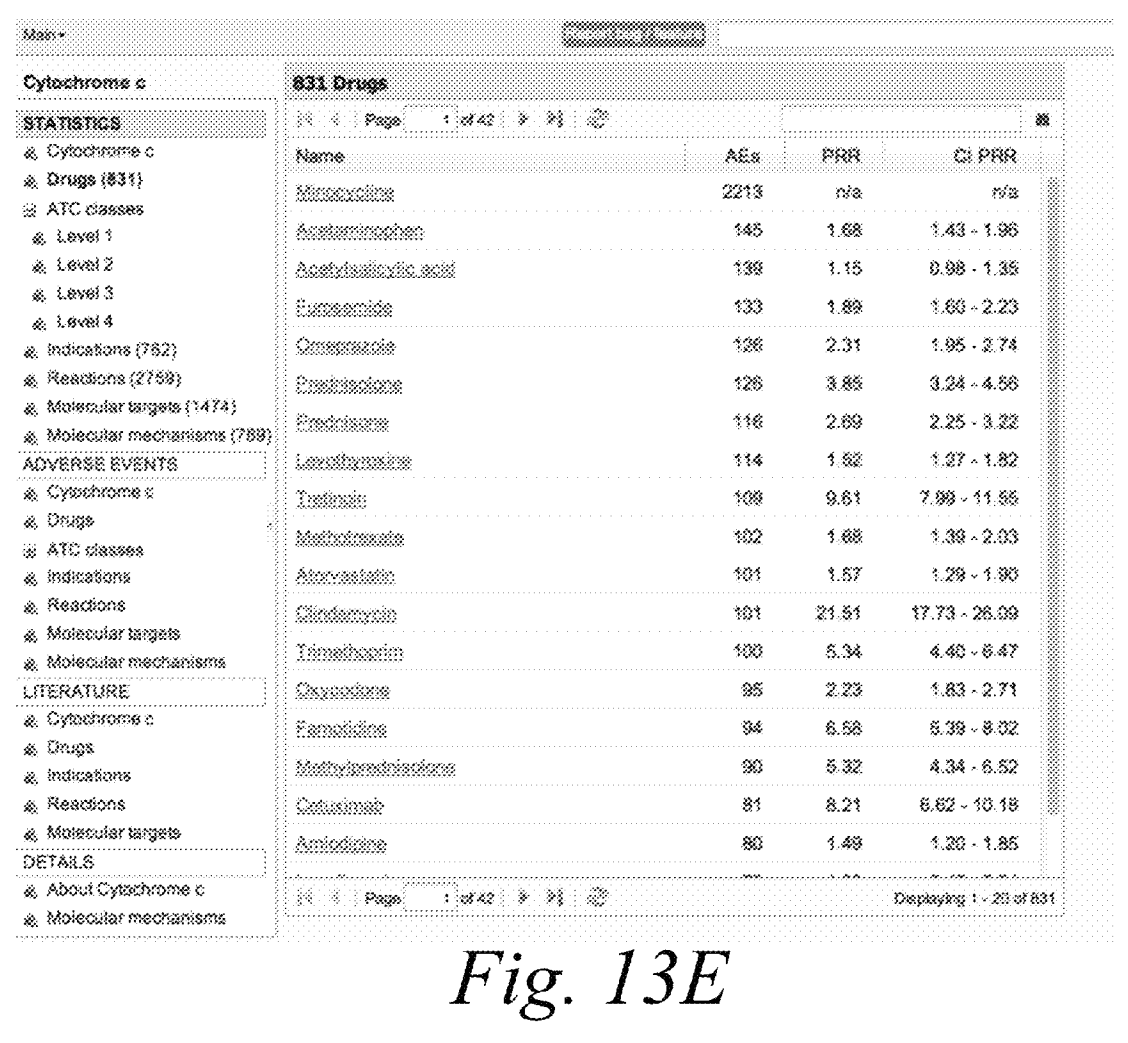
Figure 13F:
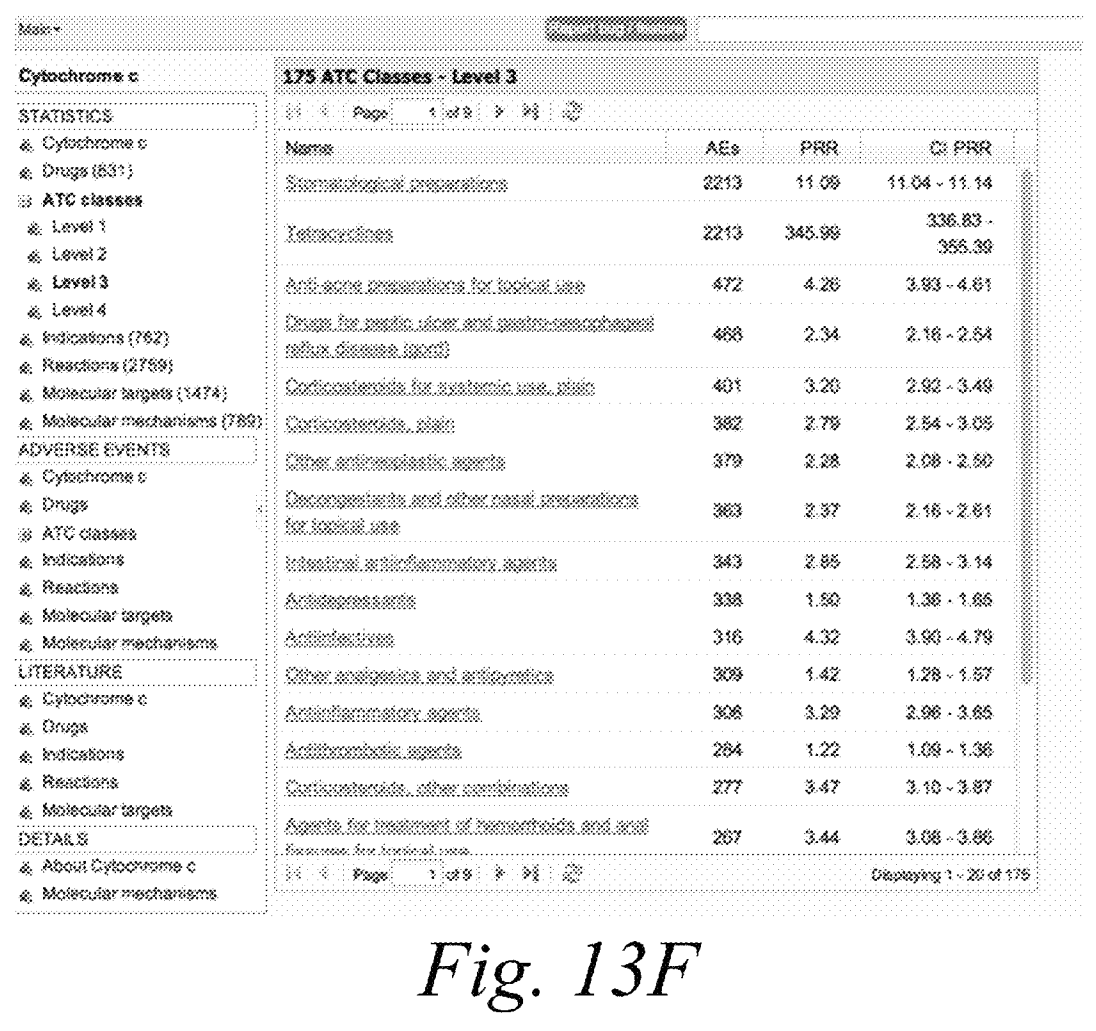
Figure 13G:
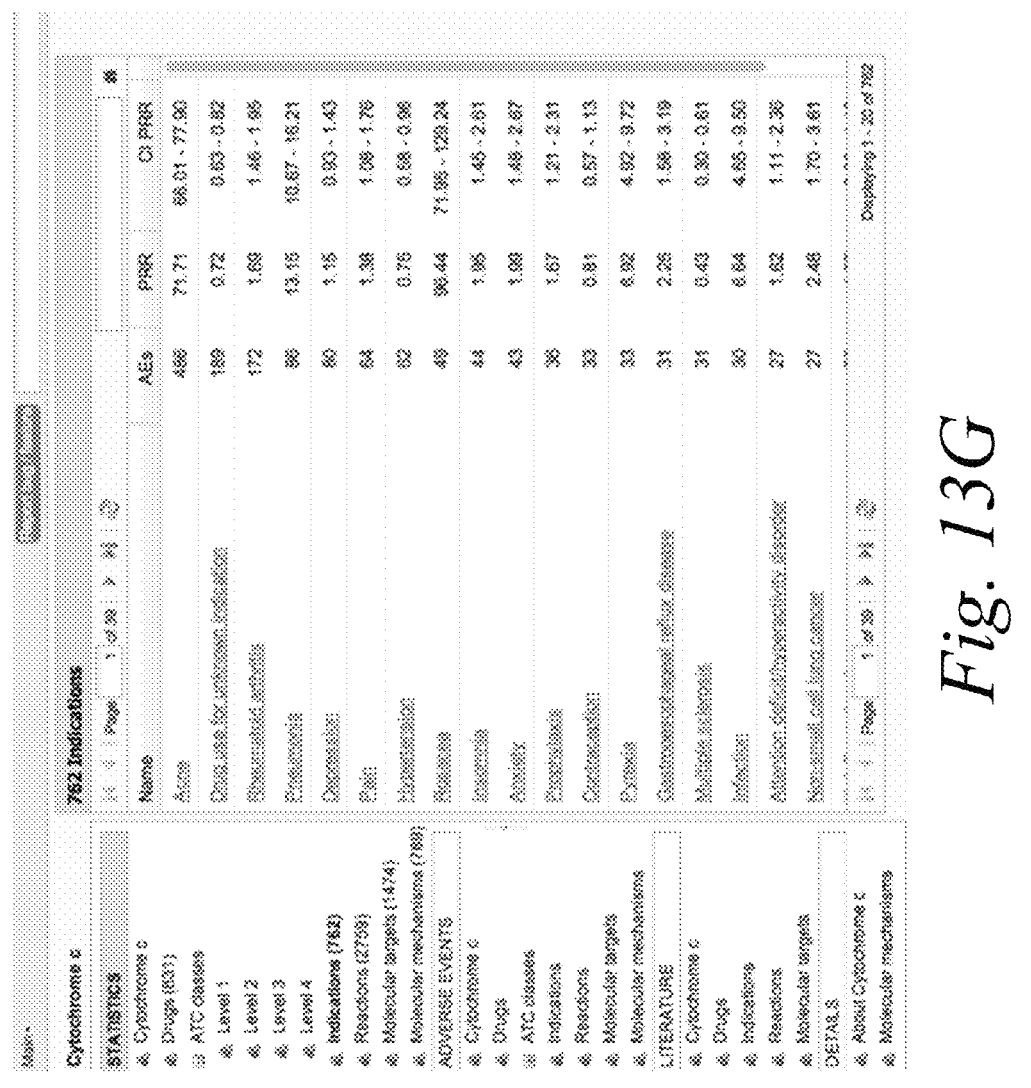
Figure 13H:
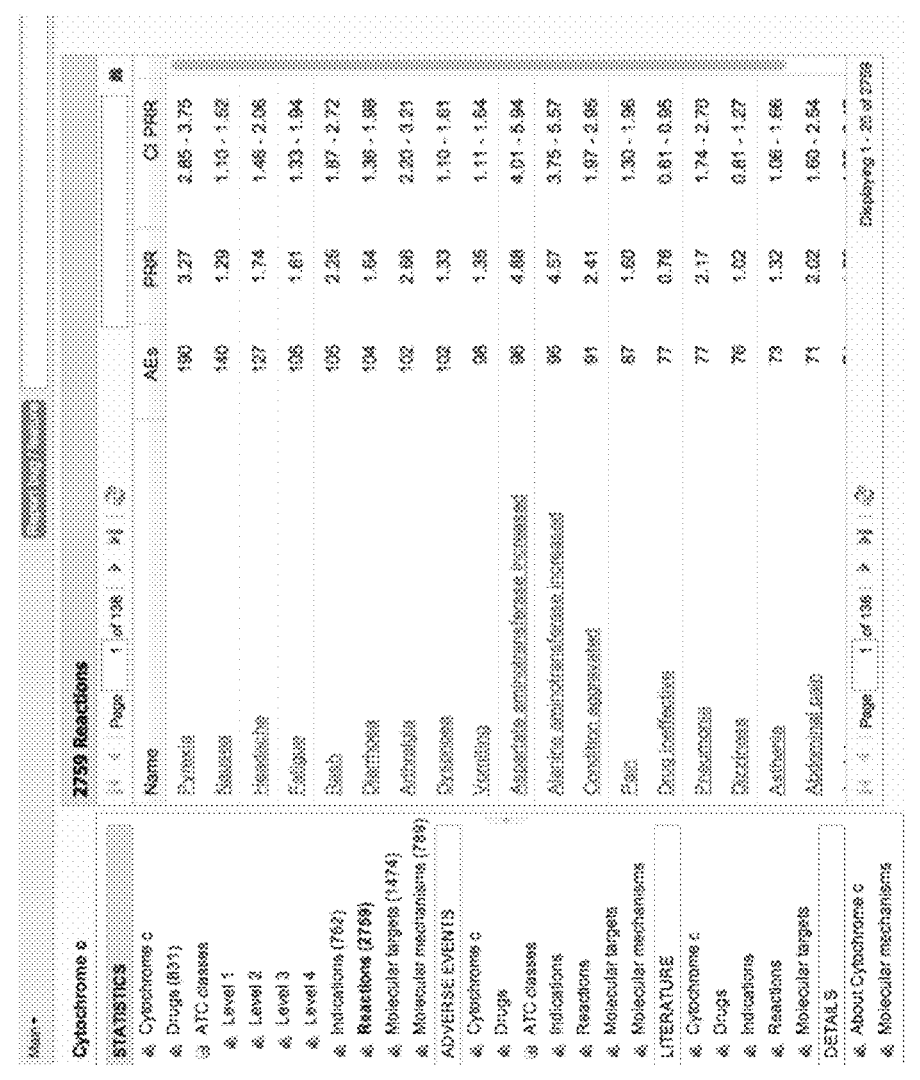
Figure 13I:
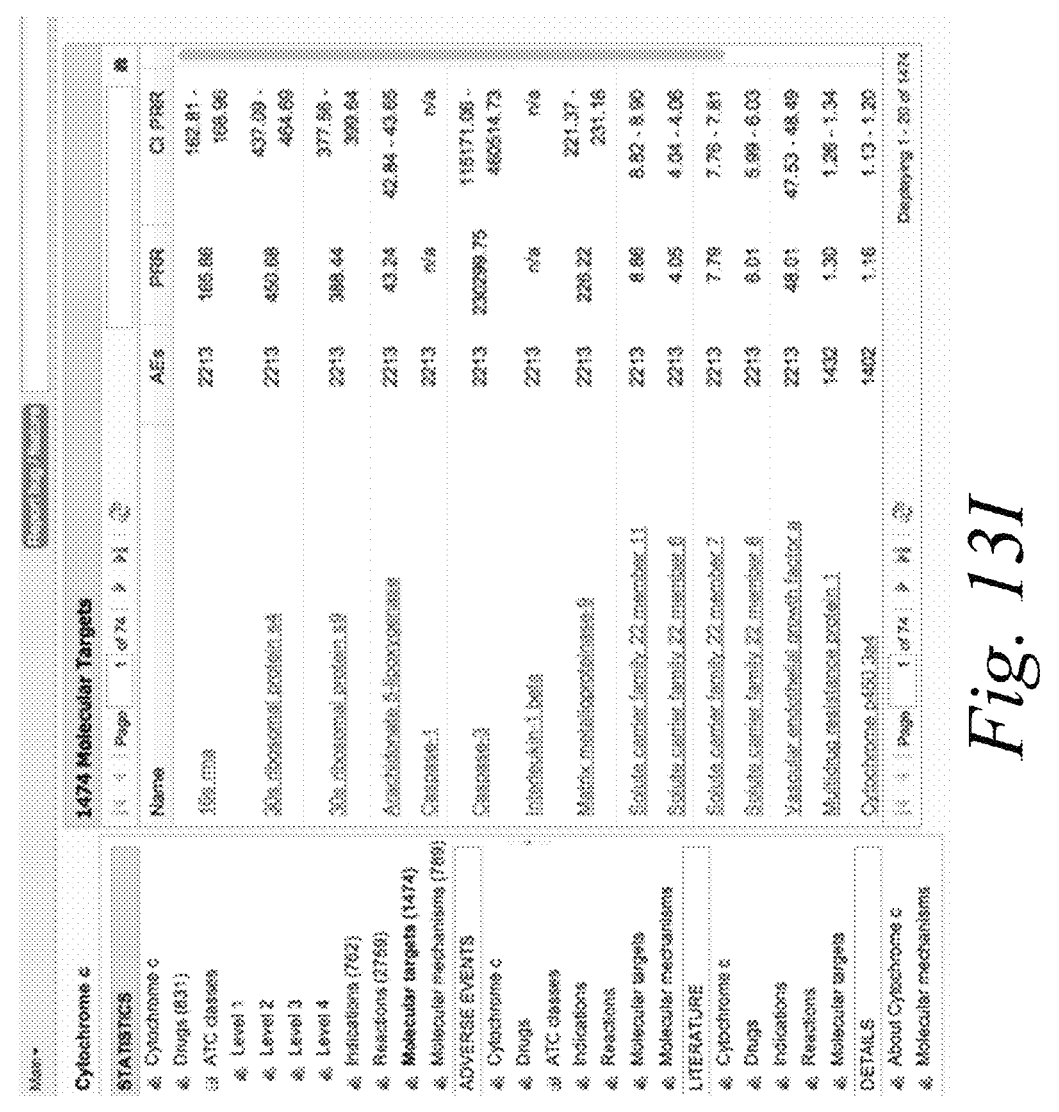
Figure 13J:
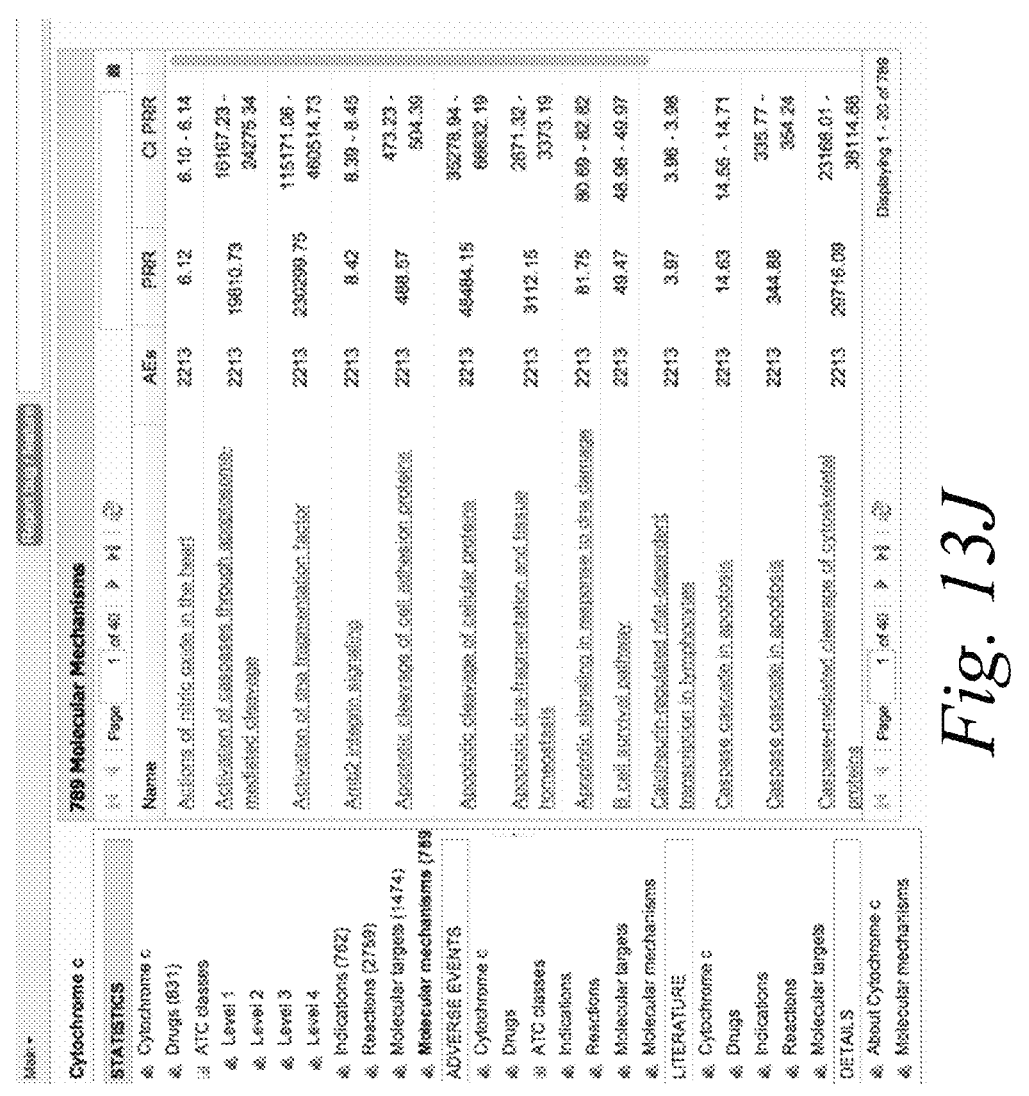
Figure 13K:
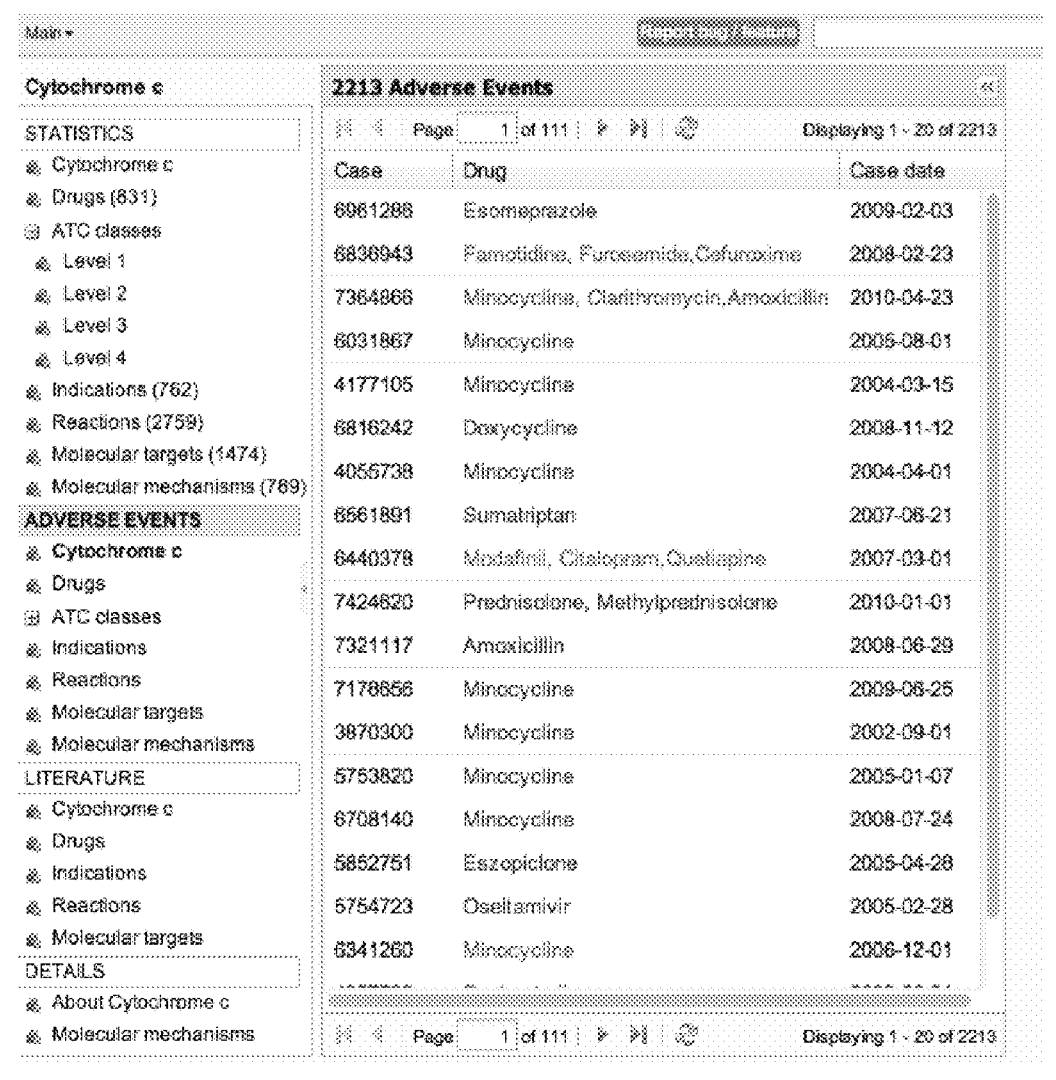
Figure 13L:
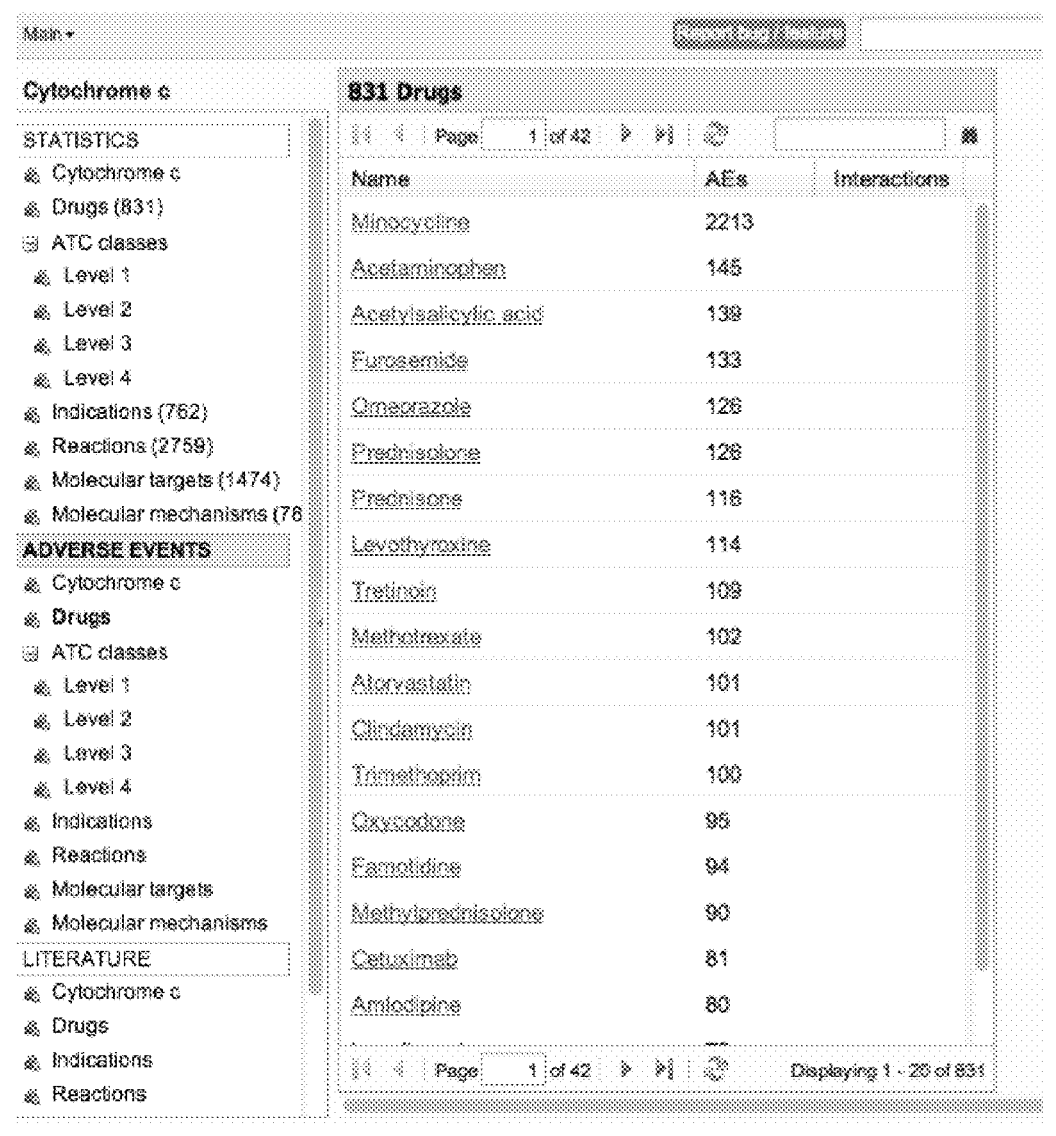
Figure 13N:
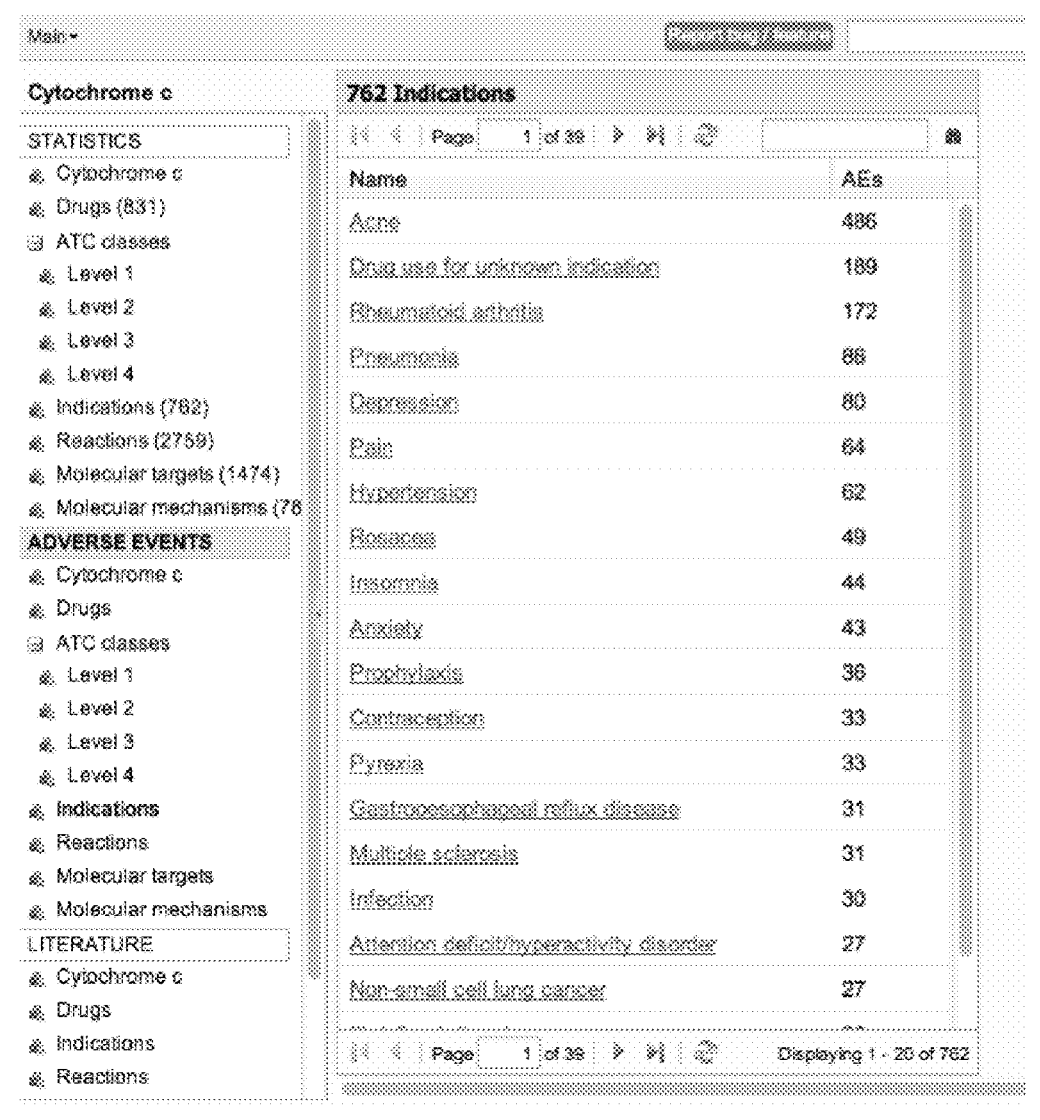
Figure 13O:
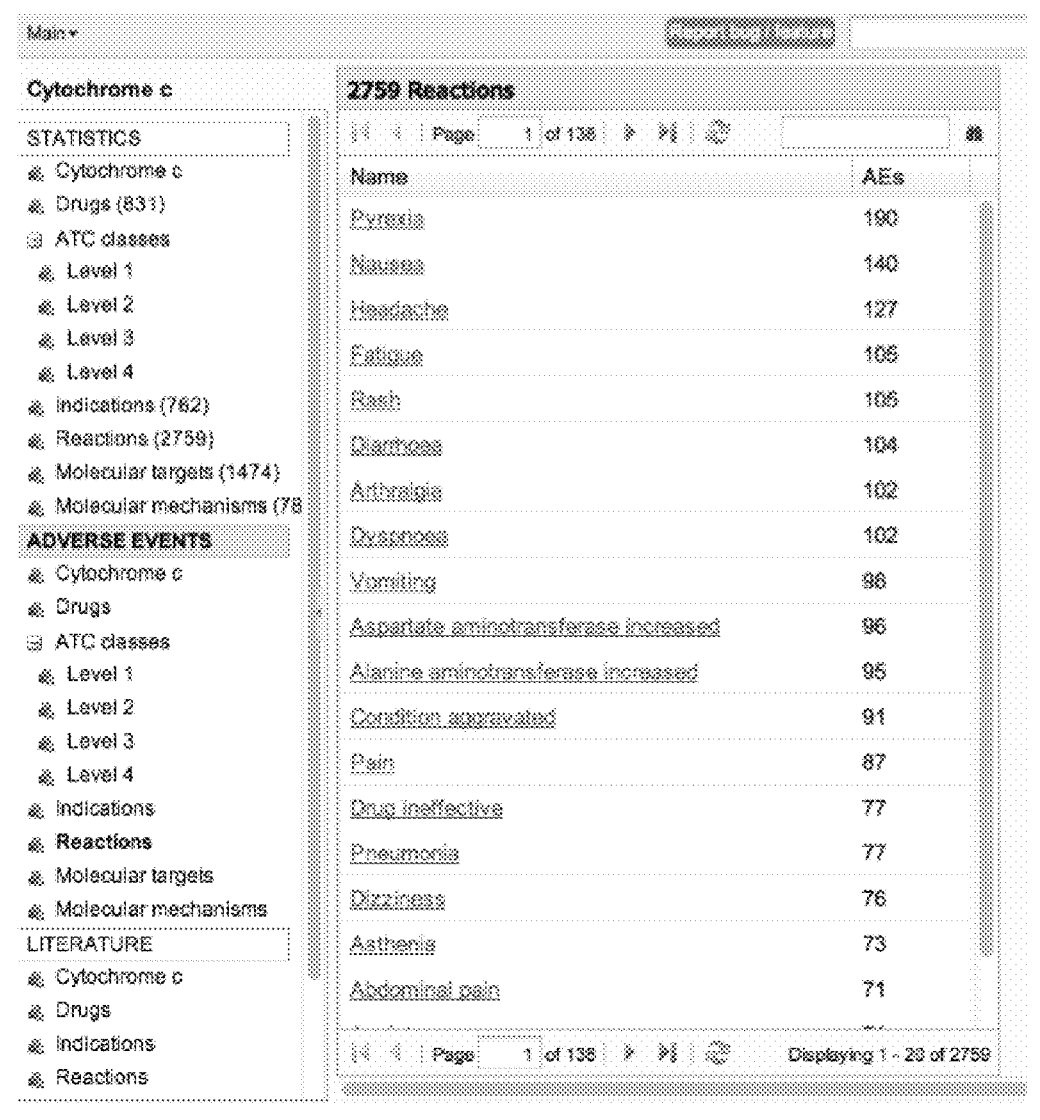
Figure 13P:
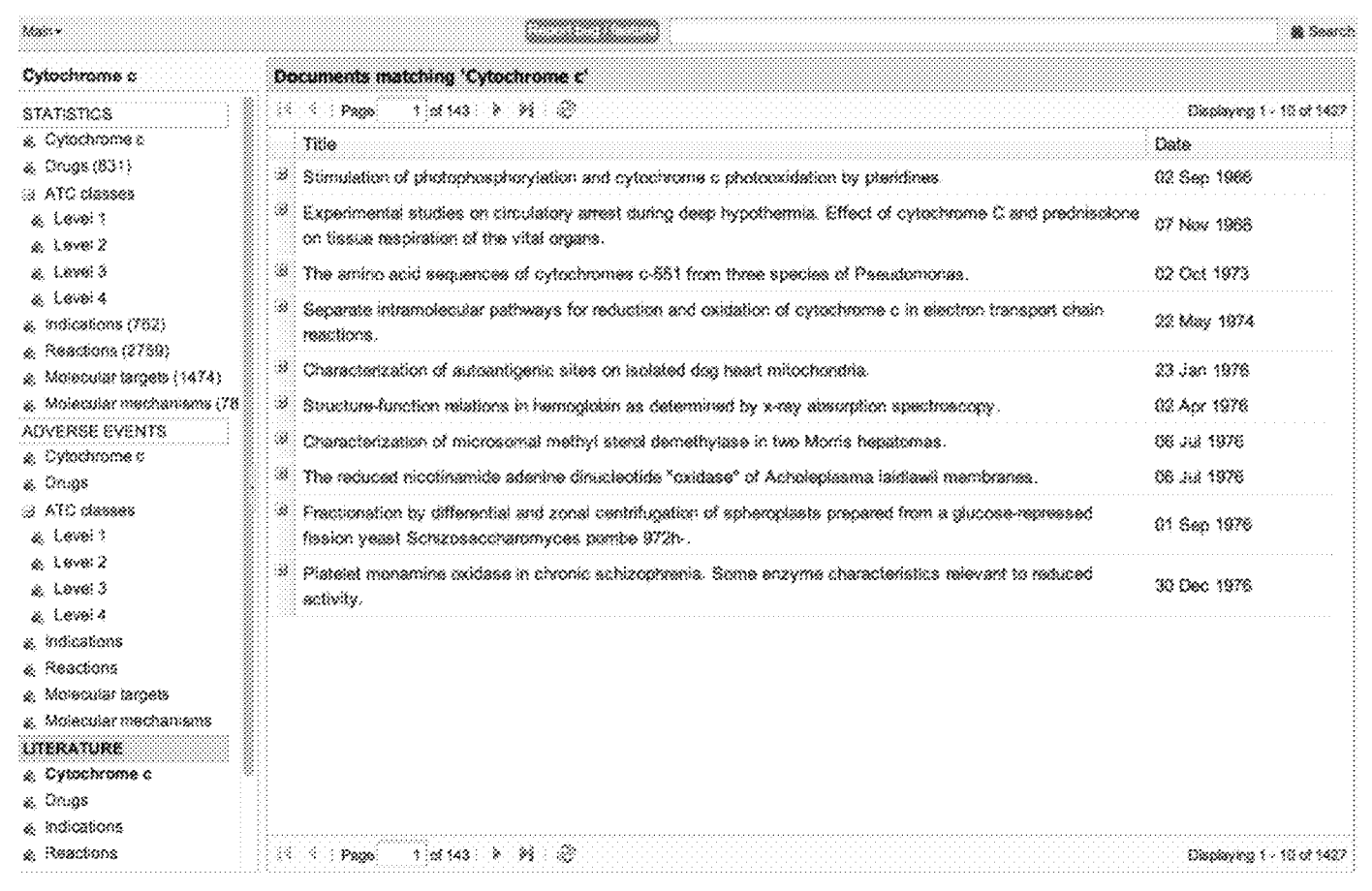
Figure 13Q:
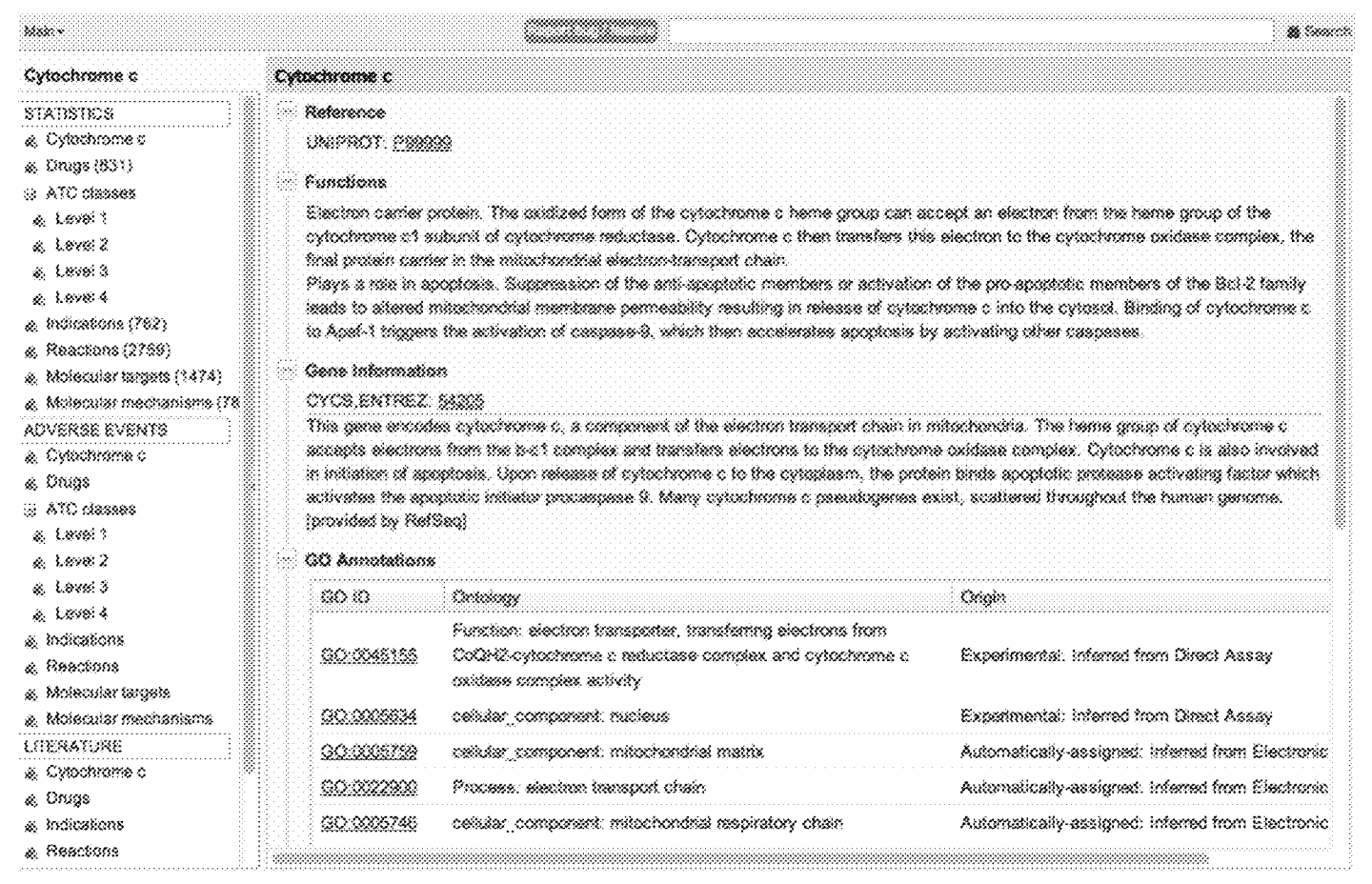
Figure 13R:
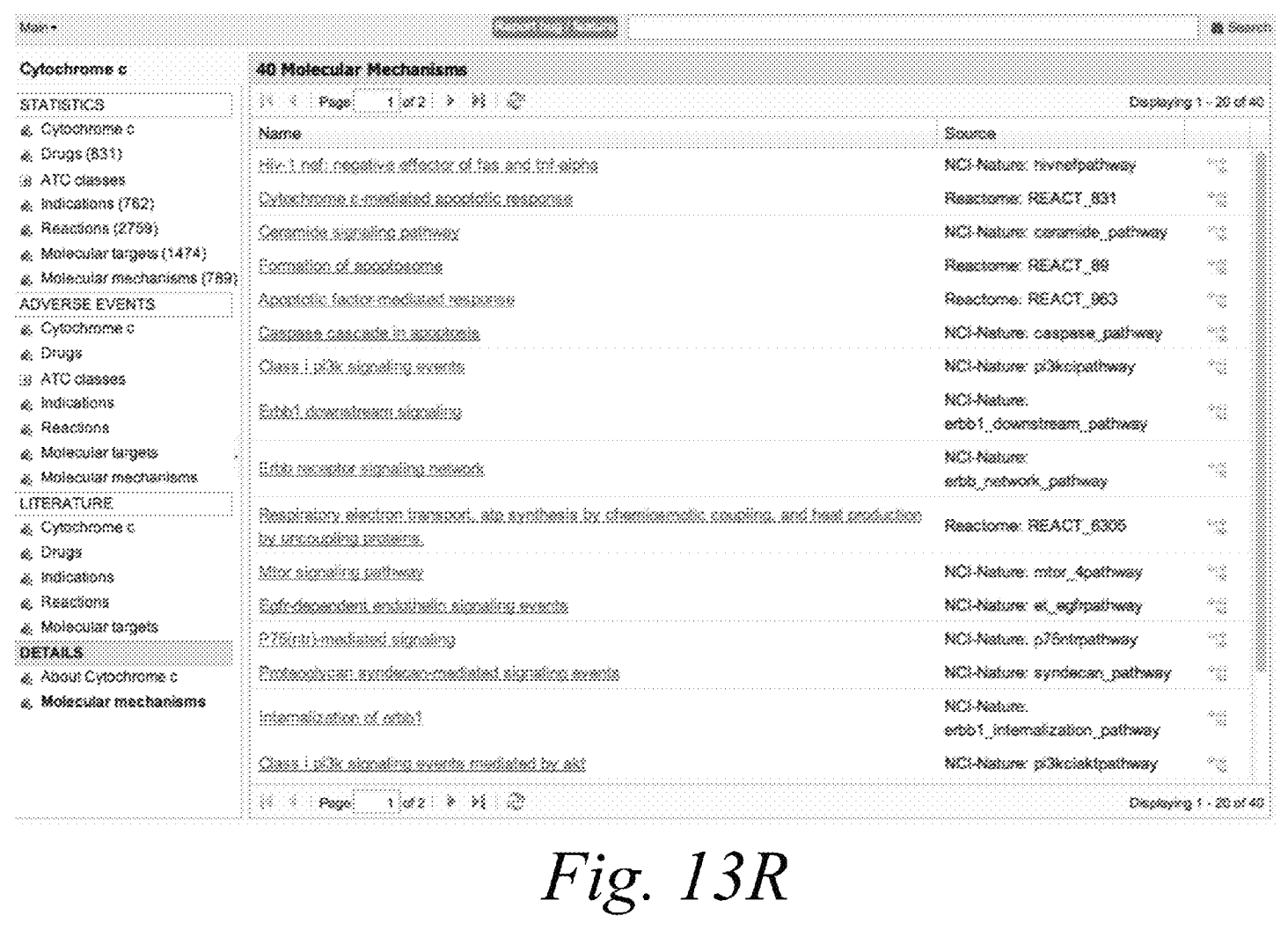
Figure 13S:
Figure 13T:
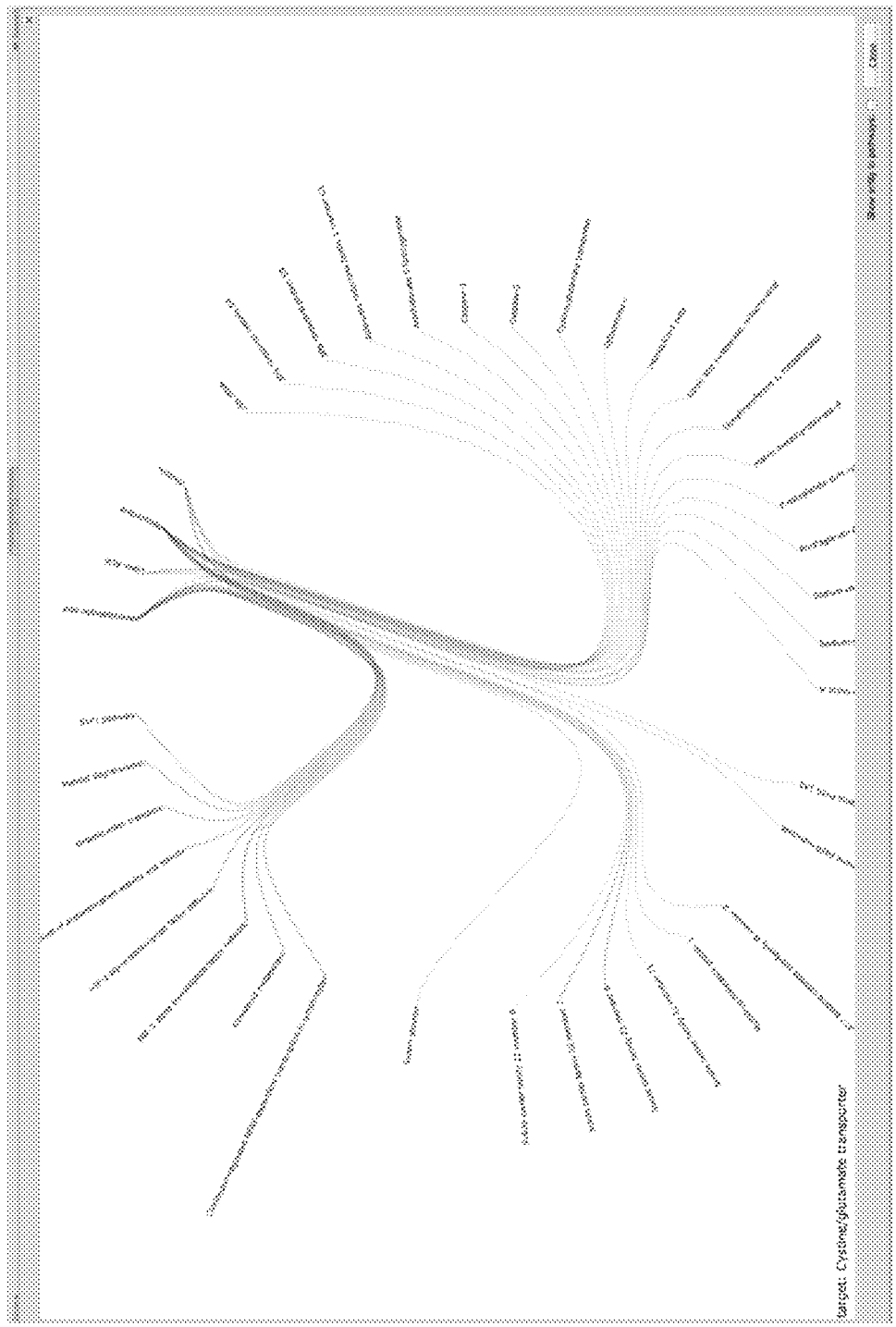
Figure 13U:
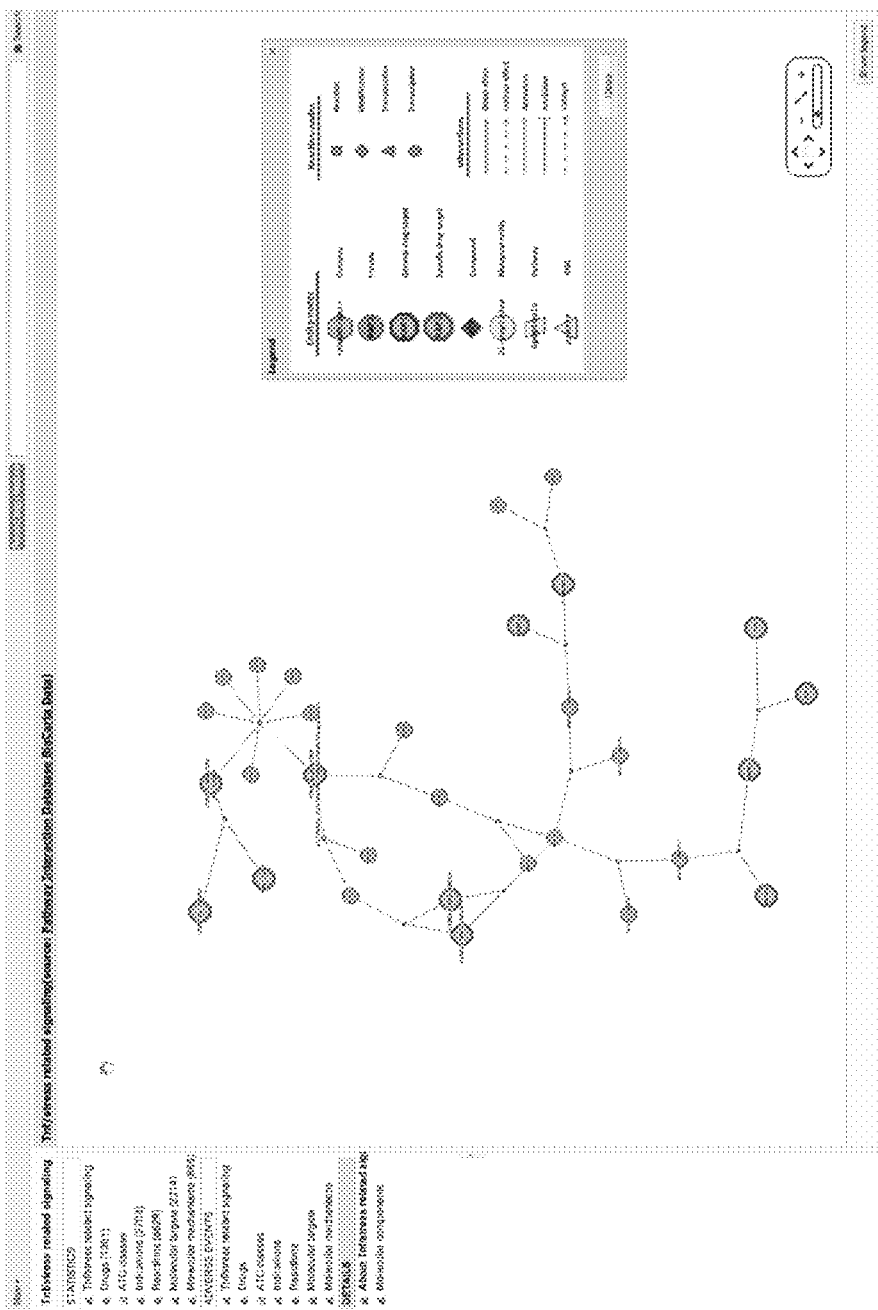
Figure 13V:
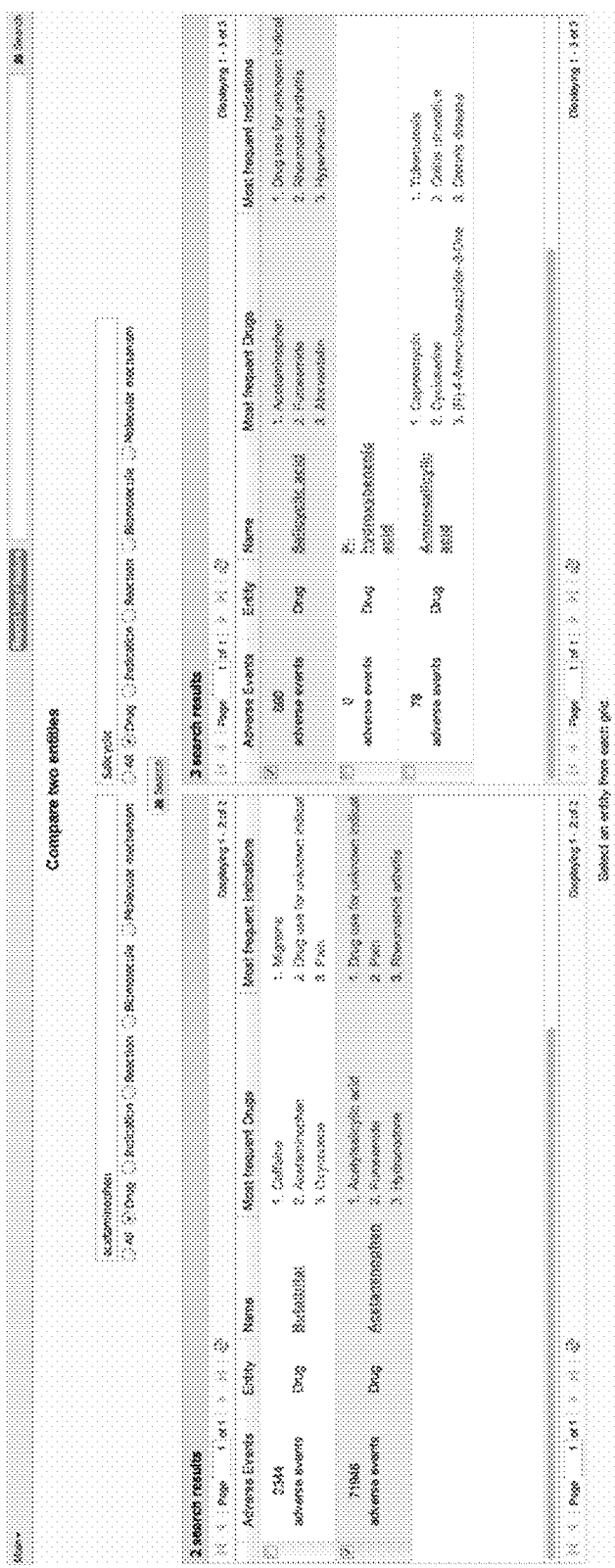
Figure 13W:
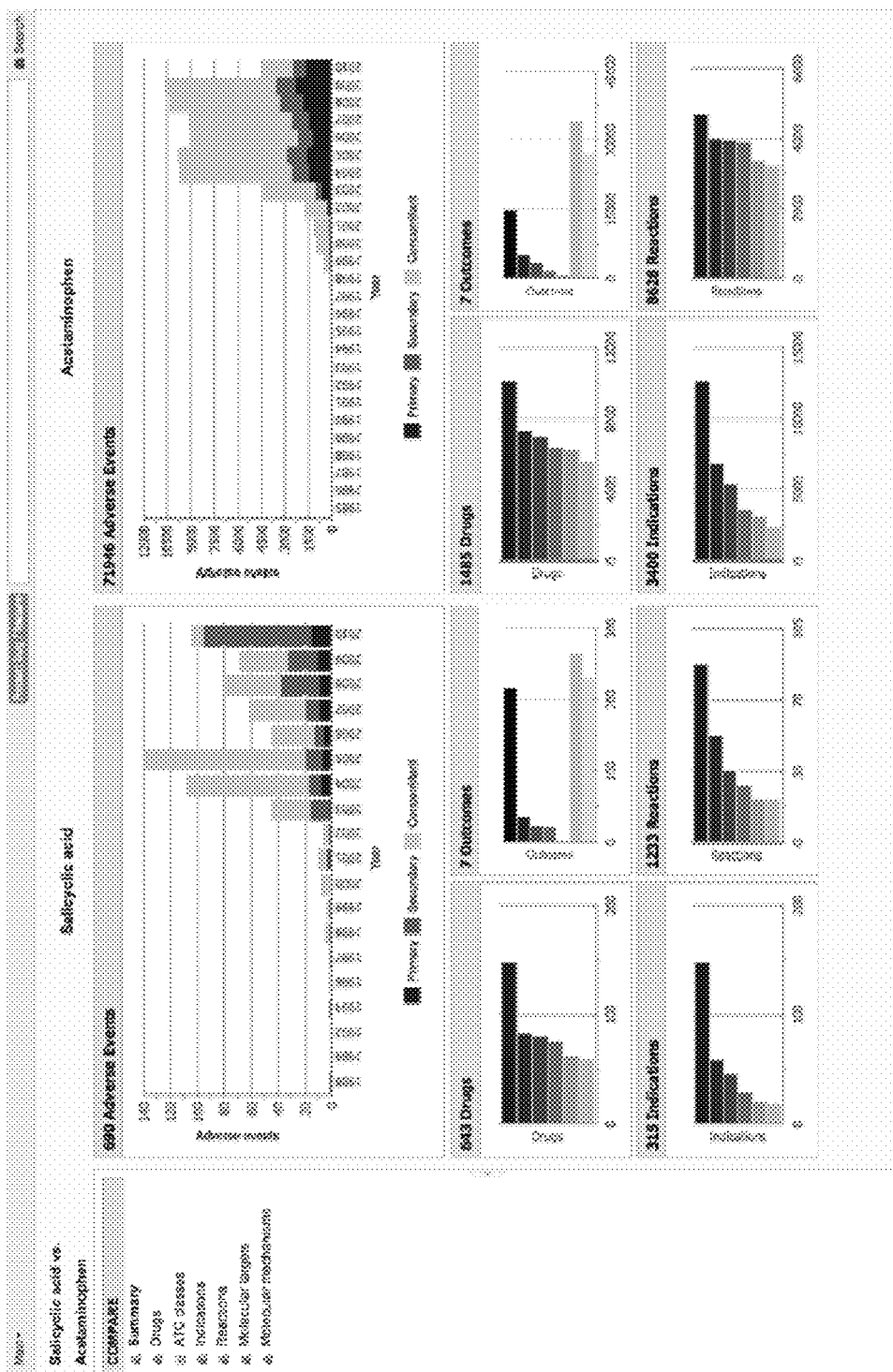
Figure 13X:
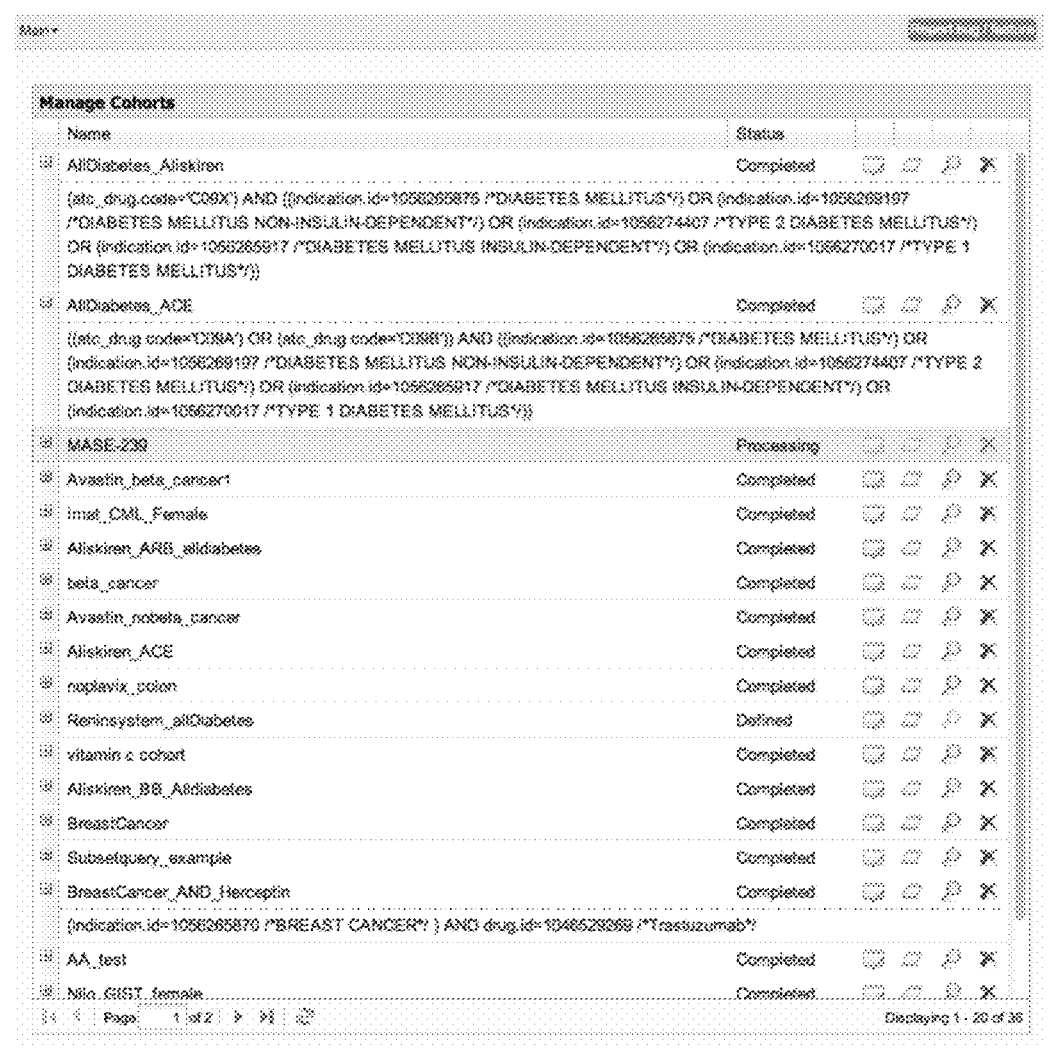
Figure 13Y:
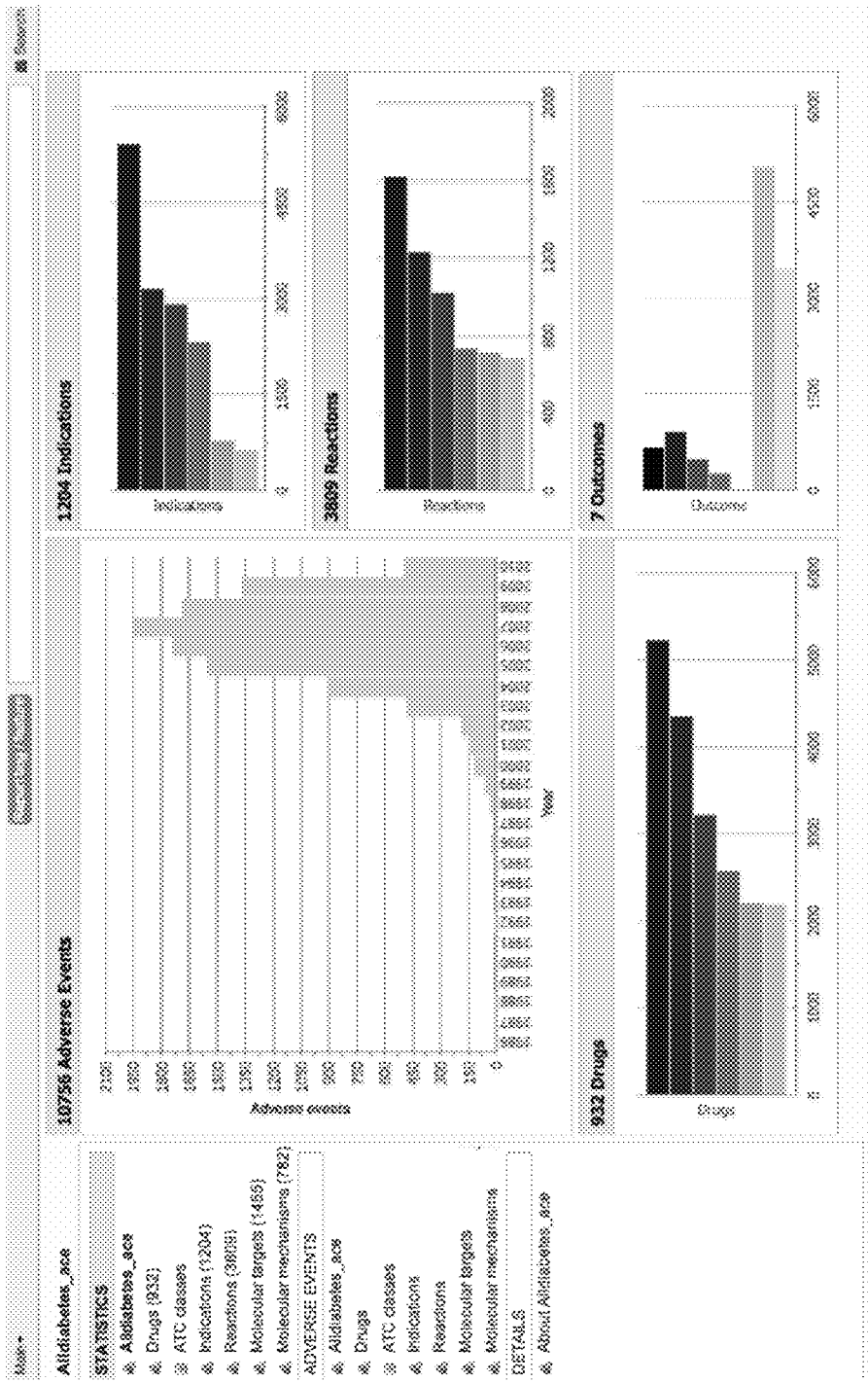

Referring first to FIGS. 13A-13Y, illustrated are screenshots of example embodiments of an interface for performing multivariate analysis of adverse event data. In some embodiments, the interface may be accessed through a web browser, while in other embodiments, the interface may be provided as part of an application. As shown in FIG. 13A, the interface may comprise a home page or screen with one or more search boxes or links. As shown in FIG. 13B, in response to a user entering a full or partial search term, the interface may display a list of results, comprising entity names matching the search, type of entity, number of adverse events in an adverse event database associated with the entity, most frequent drugs co-medicated with the entity, most frequent indications for which the entity is prescribed, and most frequent reactions associated with the entity in the adverse event database. Similarly, as shown in FIG. 13C, searches may be done for other entities or entity types.

Once an entity is selected from the search results, the interface may display a dashboard of statistical data as shown in the embodiment of FIG. 13D. Statistical data may include graphs of: numbers of adverse events associated with the entity by year; number of adverse events by indications; number of adverse events by reactions; number of adverse events by outcomes; and number of adverse events by drugs. In many embodiments, only the highest numbered indications, reactions, or drugs may be displayed on the dashboard, due to space limitations.

Navigation links in FIG. 13D provide access to further detailed information. For example, as shown in FIG. 13E, the interface may provide a list of drugs associated with the entity in adverse event data, along with statistical data regarding their frequency in the reports. Similarly, as shown in FIG. 13F, the interface may provide a list of Anatomical Therapeutic Chemical (ATC) classes, grouped by level, associated with the entity in adverse event data, along with statistical data regarding their frequency in the reports. In some embodiments, similar lists may be displayed by the interface, including indications (as shown in FIG. 13G); reactions (as shown in FIG. 13H); molecular targets (as shown in FIG. 13I); and molecular mechanisms (as shown in FIG. 13J).

In many embodiments, as shown in FIG. 13K, the interface may provide access to individual adverse event reports for the entity. In some embodiments, the interface may also provide identifications of numbers of adverse events for the entity associated with individual drugs (FIG. 13L); ATC classes (FIG. 13M); indications (FIG. 13N); reactions (FIG. 13O); molecular targets or molecular mechanisms (not shown for brevity). The interface may further provide access to literature associated with the entity in a medical literature server or accessible over a network, as shown in FIG. 13P. In some embodiments, as shown in FIG. 13Q, the interface may provide detailed information about the entity. Similarly, the interface may provide information about molecular mechanisms associated with the entity, as shown in FIG. 13R.

As discussed above in connection with FIG. 13K, the interface may provide access to individual adverse event reports for the entity, as shown in FIG. 13S. The adverse event reports may comprise demographic information for the patient who experienced the adverse event, and information regarding outcomes, consumed medications, reactions, and indications. As discussed above, in many embodiments, the interface may provide a radial dependency graph, specific to the adverse event report, as shown in FIG. 13T.

In some embodiments, the interface may provide information regarding pathways, such as a graph or portion of a global molecular entity graph showing functional relationships among entities associated with a pathway, as shown in FIG. 13U. As discussed above, in many embodiments, the interface may also provide such graphs as a result of analysis of a global molecular entity graph.

In many embodiments, the interface may provide functions for comparing two entities directly. For example, as shown in FIG. 13V, the interface may provide for side-by-side searching of entities, including different entity types, as well as side-by-side comparison of adverse event data, as shown in FIG. 13W.

In some embodiments, as discussed above, the interface may provide functions to generate cohorts for extraction of cohort-specific adverse event data. Boolean queries may be crafted defining the cohort and managed through a cohort interface, as shown in FIG. 13X. Upon processing and extraction, adverse event data specific to the cohort may be displayed and investigated, as shown in FIG. 13Y. In some embodiments, the interface may comprise a utility for building cohort definitions, as well as providing a preview of what records may be included in the defined cohort.

Figure 14A:
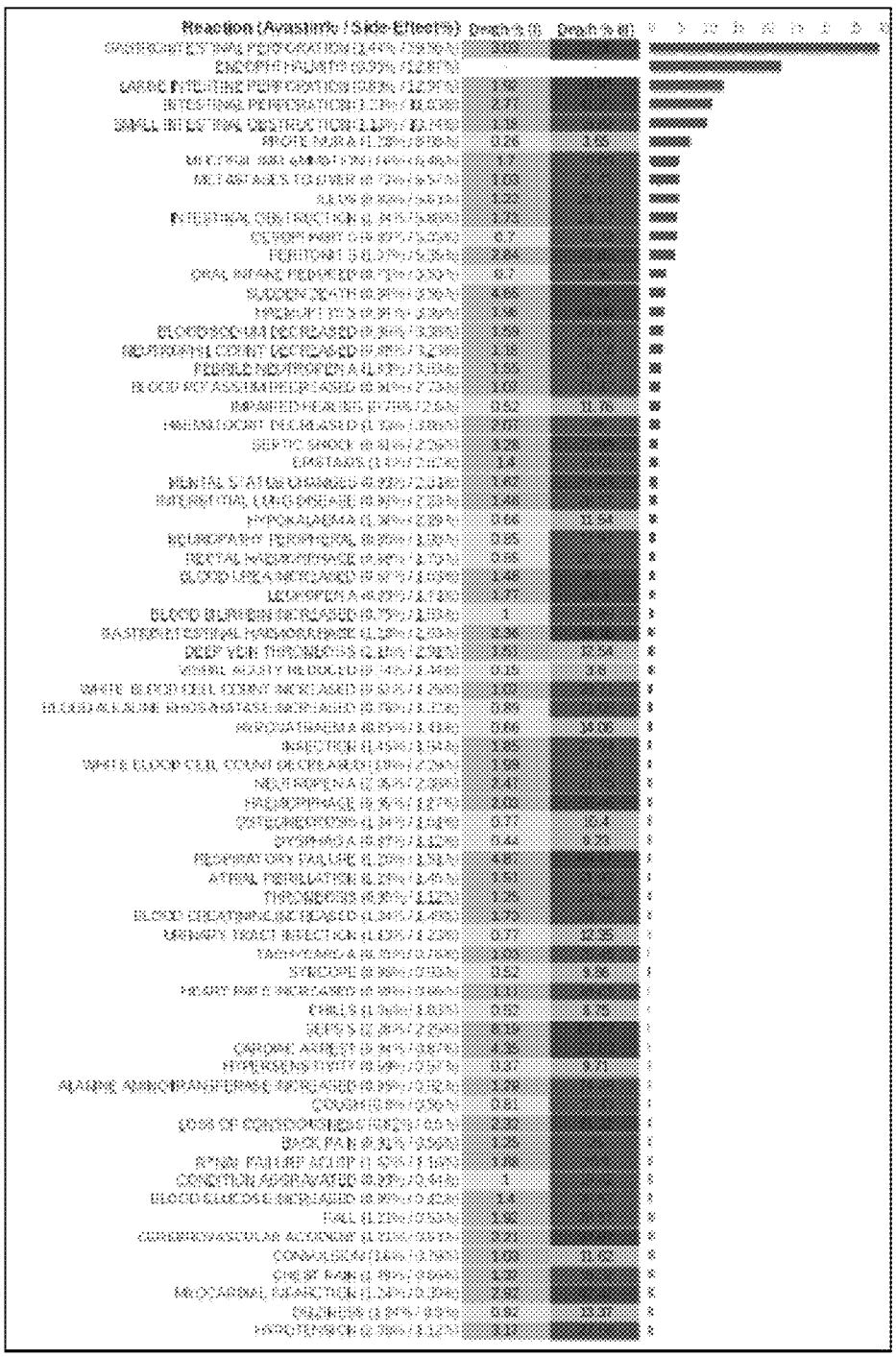
FIGS. 14A-14C are screenshots of an example embodiment of comparison of side effect profiles for molecular entities.
Figure 14B:
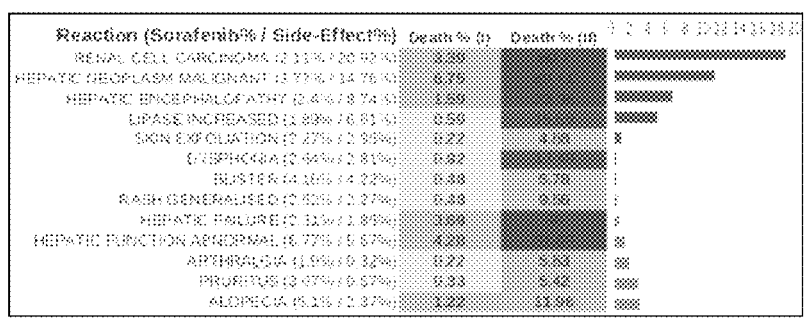
Figure 14C:
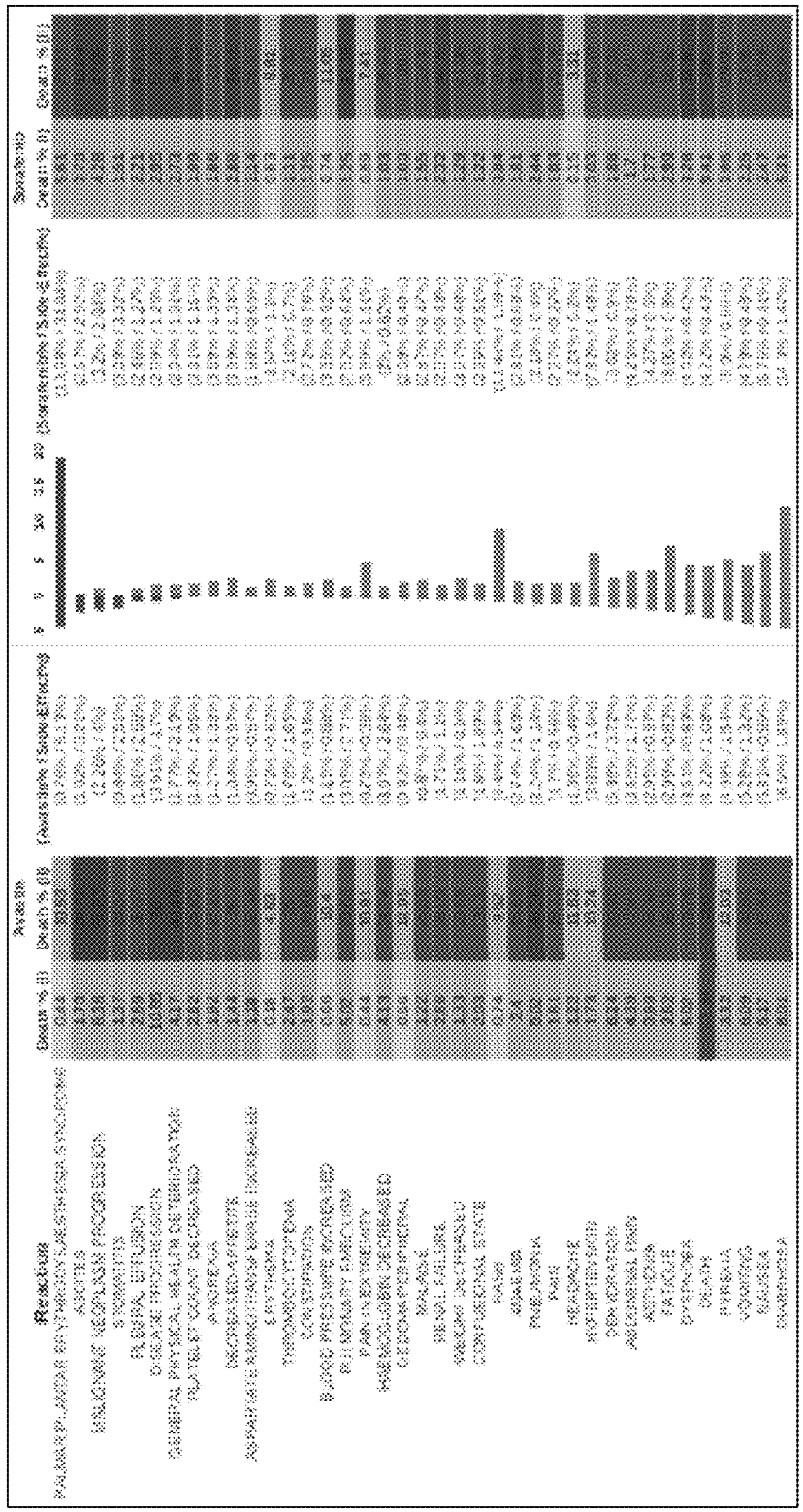

Referring briefly to FIGS. 14A-C, as discussed above, in some embodiments, a multivariate analyzer may compare side effect profiles to generate intersection or union profiles for investigation of combination therapies, prediction of side effects for novel targets, or other purposes. Referring first to FIG. 14A, illustrated is an example embodiment of a list of a side effect profile for a first medication. The list may be sorted based on frequency of reaction, for example, or based on frequency of a particular outcome, such as death. Similarly, in FIG. 14B, illustrated is an example embodiment of a list of a side effect profile for a second medication. As shown, lists may be of different length, for example, due to less data being available or due to a reduced variety of side effects for one medication. As shown in FIG. 14C, in some embodiments, side effect profiles may be directly compared and cross referenced, allowing determinations of differences in reactions between medications and generation of intersection or union profiles.

In summary, by permitting the direct assessment of relationships between the human proteome and drug-induced phenotypes, the systems and methods discussed herein provide efficient and intuitive approaches to the analysis and molecular dissection of adverse event data information. Patient specific clinico-molecular data may be integrated with the systems, providing advanced treatment decision support.

It should be understood that the systems described above may provide multiple ones of any or each of those components and these components may be provided on either a standalone machine or, in some embodiments, on multiple machines in a distributed system. The systems and methods described above may be implemented as a method, apparatus or article of manufacture using programming and/or engineering techniques to produce software, firmware, hardware, or any combination thereof. In addition, the systems and methods described above may be provided as one or more computer-readable programs embodied on or in one or more articles of manufacture. The term "article of manufacture" as used herein is intended to encompass code or logic accessible from and embedded in one or more computer-readable devices, firmware, programmable logic, memory devices (e.g., EEPROMs, ROMs, PROMs, RAMs, SRAMs, etc.), hardware (e.g., integrated circuit chip, Field Programmable Gate Array (FPGA), Application Specific Integrated Circuit (ASIC), etc.), electronic devices, a computer readable non-volatile storage unit (e.g., CD-ROM, floppy disk, hard disk drive, etc.). The article of manufacture may be accessible from a file server providing access to the computer-readable programs via a network transmission line, wireless transmission media, signals propagating through space, radio waves, infrared signals, etc. The article of manufacture may be a flash memory card or a magnetic tape. The article of manufacture includes hardware logic as well as software or programmable code embedded in a computer readable medium that is executed by a processor. In general, the computer-readable programs may be implemented in any programming language, such as LISP, PERL, C, C++, C#, PROLOG, or in any byte code language such as JAVA. The software programs may be stored on or in one or more articles of manufacture as object code.

Having described certain embodiments of methods and systems for providing systems and methods for molecular analysis of adverse event data, it will now become apparent to one of skill in the art that other embodiments incorporating the concepts of the invention may be used.

What is claimed:

1. A method for identifying unknown drug targets via adverse event data, comprising:
   receiving, by an analyzer module executed by a processor of a computing device from a user, an identification of a first drug having one or more unknown target proteins;
   identifying, by the analyzer module from a medication information database stored in a computer-readable storage medium, a second drug related to the first drug;
   retrieving, by the analyzer module from an adverse event database stored in the computer-readable storage medium, a first side effect profile associated with the first drug, and a second side effect profile associated with the second drug;
   generating, by the analyzer module, a third side effect profile comprising a subset of the first side effect profile not shared by the second side effect profile;
   identifying, by the analyzer module from the adverse event database, a third drug having a fourth side effect profile comprising the third side effect profile;
   retrieving, by the analyzer module from the medication information database, a list of one or more target proteins of the third drug not targeted by the second drug; and
   presenting, by the analyzer module via a display interface of the computing device to the user, the retrieved list of one or more target proteins as potential target proteins of the first drug.

2. The method of claim 1, wherein the second drug is in the same class as the first drug.

3. The method of claim 1, wherein the first drug and second drug are identified as binding to the same target protein.

4. The method of claim 1, wherein each of the first, second, and fourth side effect profiles comprise a statistical index of side effects experienced by consumers of the corresponding first, second, and third drugs.

5. The method of claim 1, wherein generating the third side effect profile comprises subtracting a frequency of occurrence of a side effect in the second side effect profile from a frequency of occurrence of the side effect in the first side effect profile.

6. The method of claim 1, wherein generating the third side effect profile comprises identifying a side effect with a first frequency of occurrence in the first side effect profile and a second frequency of occurrence in the second side effect profile.

7. The method of claim 6, further comprising excluding the identified side effect from the third side effect profile, responsive to the first frequency of occurrence being within a predetermined threshold from the second frequency of occurrence.

8. The method of claim 6, further comprising including the identified side effect in the third side effect profile, responsive the first frequency of occurrence being outside a predetermined threshold from the second frequency of occurrence.

9. The method of claim 1, wherein identifying a third drug having a fourth side effect profile comprises identifying a side effect with a first frequency of occurrence in the third side effect profile and a second frequency of occurrence in the fourth side effect profile, the first frequency of occurrence and second frequency of occurrence being within a predetermined threshold.

10. A system for identifying unknown drug targets via adverse event data, comprising:
    a computing device, in communication with a computer-readable storage medium comprising an adverse event database and a medication information database, comprising a display interface and a processor executing an analyzer module configured for:
    receiving, from a user, an identification of a first drug having one or more unknown target proteins;
    identifying, from the medication information database, a second drug related to the first drug;
    retrieving, from the adverse event database, a first side effect profile associated with the first drug, and a second side effect profile associated with the second drug;
    generating a third side effect profile comprising a subset of the first side effect profile not shared by the second side effect profile;
    identifying, from the adverse event database, a third drug having a fourth side effect profile comprising the third side effect profile;
    retrieving, from the medication information database, a list of one or more target proteins of the third drug not targeted by the second drug; and
    presenting, via the display interface to the user, the retrieved list of one or more target proteins as potential target proteins of the first drug.

11. The system of claim 10, wherein the second drug is in the same class as the first drug.

12. The system of claim 10, wherein the first drug and second drug are identified as binding to the same target protein.

13. The system of claim 10, wherein each of the first, second, and fourth side effect profiles comprise a statistical index of side effects experienced by consumers of the corresponding first, second, and third drugs.

14. The system of claim 10, wherein the analyzer module is further configured for subtracting a frequency of occurrence of a side effect in the second side effect profile from a frequency of occurrence of the side effect in the first side effect profile.

15. The system of claim 10, wherein the analyzer module is further configured for identifying a side effect with a first frequency of occurrence in the first side effect profile and a second frequency of occurrence in the second side effect profile.

16. The system of claim 15, wherein the analyzer module is further configured for excluding the identified side effect from the third side effect profile, responsive to the first frequency of occurrence being within a predetermined threshold from the second frequency of occurrence.

17. The system of claim 15, wherein the analyzer module is further configured for including the identified side effect in the third side effect profile, responsive the first frequency of occurrence being outside a predetermined threshold from the second frequency of occurrence.

18. The system of claim 10, wherein the analyzer module is further configured for identifying a side effect with a first frequency of occurrence in the third side effect profile and a second frequency of occurrence in the fourth side effect profile, the first frequency of occurrence and second frequency of occurrence being within a predetermined threshold.

* * * * *